US008709754B2

(12) United States Patent
Krumm et al.

(10) Patent No.: US 8,709,754 B2
(45) Date of Patent: Apr. 29, 2014

(54) RECOMBINANT VECTORS FOR USE IN POSITION-INDEPENDENT TRANSGENE EXPRESSION WITHIN CHROMATIN

(75) Inventors: Anton Krumm, Seattle, WA (US); Wendy Gombert, Belleuve, WA (US)

(73) Assignee: University of Washington, Seattle, WA (US)

( * ) Notice: Subject to any disclaimer, the term of this patent is extended or adjusted under 35 U.S.C. 154(b) by 1437 days.

(21) Appl. No.: 11/879,542

(22) Filed: Jul. 17, 2007

(65) Prior Publication Data
US 2008/0305541 A1   Dec. 11, 2008

Related U.S. Application Data

(60) Division of application No. 11/009,389, filed on Dec. 10, 2004, now abandoned, which is a continuation-in-part of application No. 10/853,581, filed on May 24, 2004, now abandoned.

(60) Provisional application No. 60/473,109, filed on May 23, 2003.

(51) Int. Cl.
| C12P 21/06 | (2006.01) |
| A01N 63/00 | (2006.01) |
| C12N 15/00 | (2006.01) |
| C12N 1/00 | (2006.01) |

(52) U.S. Cl.
USPC ...... 435/69.1; 424/93.2; 435/320.1; 435/243; 536/24.1

(58) Field of Classification Search
USPC ............ 435/69.1, 320.1, 70.1, 243; 424/93.2; 536/24.1
See application file for complete search history.

(56) References Cited

U.S. PATENT DOCUMENTS

| 6,365,151 B1 | 4/2002 | Halpern et al. |
| 2004/0023267 A1 | 2/2004 | Morris |
| 2004/0072264 A1 | 4/2004 | Morris et al. |

FOREIGN PATENT DOCUMENTS

| WO | 03/008583 | 1/2003 |
| WO | 03/016500 | 2/2003 |
| WO | 03/038129 | 5/2003 |
| WO | 03/039484 | 5/2003 |

OTHER PUBLICATIONS

West AG et al., Genes Dev. Feb. 1, 2002;16(3):271-88. Insulators: many functions, many mechanisms.*
Noma et al., Science Aug. 10, 2001: vol. 293. No. 5532, pp. 1150-1155 Transitions in Distinct Histone H3 Methylation Patterns at the Heterochromatin Domain Boundaries.*
Bell et al., Cell vol. 98, Issue 3, Aug. 6, 1999, pp. 387-396 The Protein CTCF Is Required for the Enhancer Blocking Activity of Vertebrate Insulators.*
Labrador et al., Cell vol. 111, Issue 2, Oct. 18, 2002, pp. 151-154 Setting the Boundaries of Chromatin Domains and Nuclear Organization.*
Voet et al.,, Biochemistry John Wiley and Sons, 1990, pp. 126-128.*
Kimchi-Sarfaty C et al., A "silent" polymorphism in the MDR1 gene changes substrate specificity.Science. Jan. 26, 2007;315(5811):525-8. Epub Dec. 21, 2006.*
Rudinger, J., "Characteristics of the amino acids as components of a peptide hormone sequence",in Peptide Hormones, University Park Press: Baltimore, MD, pp. 1-7, 1976.*
Ngo, J. et al., "Computational Complexity, Protein Structure Prediction, and the Levinthal Paradox", 1994, The Protein Folding Problem and Tertiary Structure Prediction, Merz et al. (eds.), Birkhauser Boston: Boston, MA, pp. 433 and 492-506.*
Gombert et al. The c-myc Insulator Element and Matrix Attachment Regions Define the c-myc Chromosomal Domain Molecular and Cellular Biology, Dec. 2003, p. 9338-9348, vol. 23, No. 24.*
Klenova, et al., Functional Phosphorylation Sites in the C-Terminal Region of the Multivalent Multifunctional Transcriptional Factor CTCF Mol Cell Biol. Mar. 2001; 21(6): 2221-2234.*
GeneBank Accession No. AF315312 (see STIC search titled us-11-009-389-1.rge, Result 1, References [1]-[3] pp. 1-3).
GeneBank Accession No. AC103819 (see STIC search titled us-11-009-389-1.rge, Result 2, References [1]-[4] pp. 3-6).
GeneBank Accession No. AC125515 (see STIC search titled us-11-009-389-1.rge, Result 3, References [1]-[3] pp. 6-7).
GeneBank Accession No. ABZ83530 (see STIC search titled us-11-009-389-1-mg, Result 1, pp. 1-2).
GeneBank Accession No. ADE85183 (see STIC search titled us-11-009-389-1.mg, Result 2, pp. 2-3).
GeneBank Accession No. ADB72233 (see STIC search titled us-11-009-389-9.mg, Result 2, pp. 3-4).
GeneBank Accession No. ADE95743 (see STIC search titled us-11-009-389-9.rng, Result 4, pp. 5-6).
GeneBank Accession No. AC134611 (see STIC search titled us-11-009-389-9.rge, Result 3, Reference 2, pp. 4-6).

(Continued)

*Primary Examiner* — Maria Leavitt
(74) *Attorney, Agent, or Firm* — Mark J. FitzGerald; Nixon Peabody, LLP

(57) ABSTRACT

The embodiments of the present invention are directed to discrete, cis-acting regulatory elements that include a barrier element, an insulating element, a silencing element, and matrix attachment regions ("MARs"). Additional embodiments of the present invention are directed to nucleic acid molecules that are useful for facilitating stable transgene expression within a chromatin environment. Additional embodiments of the present invention are directed to recombinant expression vectors including nucleic acid molecules of the present invention that can be incorporated into artificial chromosomes, eukaryotic cell-lines, non-human transgenic animals, and transgenic plants, to improve recombinant protein production in a broad range of eukaryotic hosts, and pharmaceutical compositions including nucleic acid molecules of the present invention that are also useful for gene therapy in the treatment of various genetic diseases.

15 Claims, 9 Drawing Sheets

(56) References Cited

OTHER PUBLICATIONS

GeneBank Accession No. HSA315134 (see STIC search titled us-11-009-389-1.rge, Result 5, References [1]-[2] pp. 9-10).
GeneBank Accession No. AF176208 (see STIC search titled us-11-009-389-1.rge, Result 6, References [1]-[2] pp. 10-11).
GeneBank Accession No. AAQ37740 (see STIC search titled us-11-009-389-1.rng, Result 3, p. 3).
GeneBank Accession No. AF339023 (see STIC search titled us-11-009-389-9.rge, Result 4, Reference 2, pp. 6-7).
SEQ ID No. 19 US-394-948-19 (see STIC search titled us-11-009-389-9.rnpbm, Result 1, pp. 1-2).

* cited by examiner

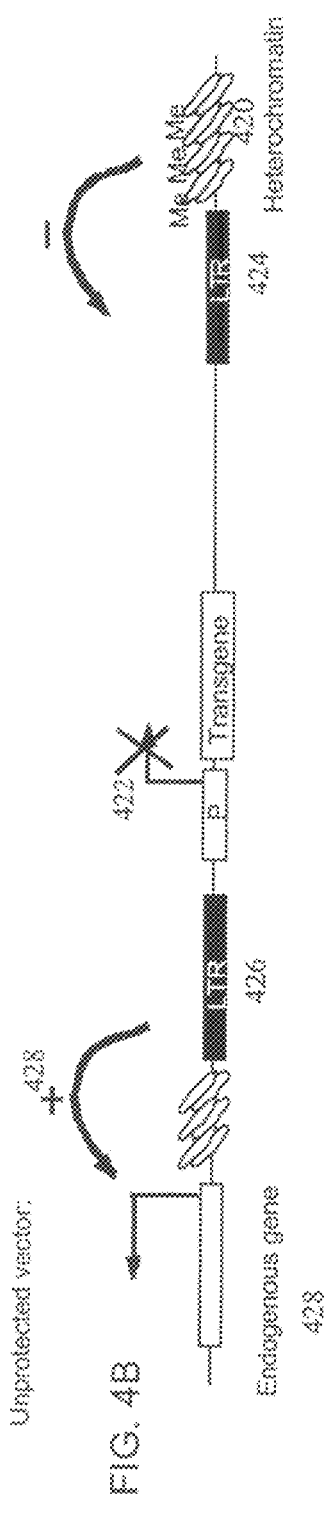
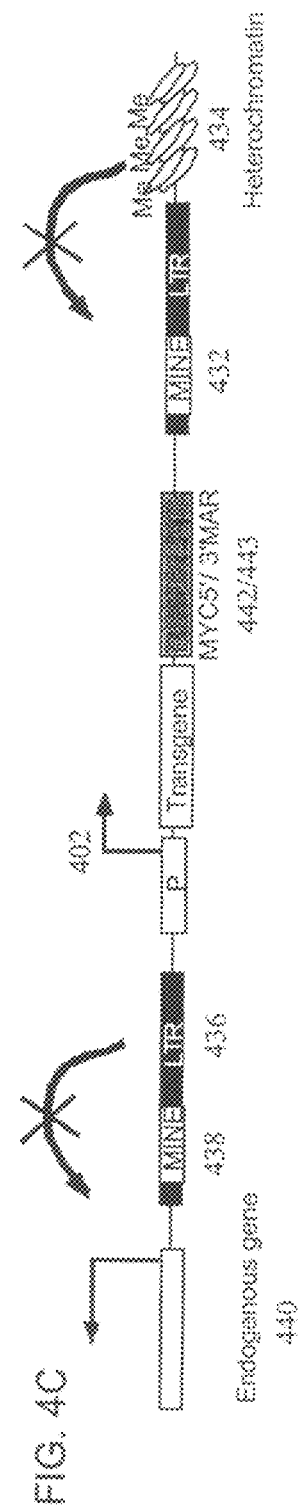
FIG. 4A
FIG. 4B
FIG. 4C

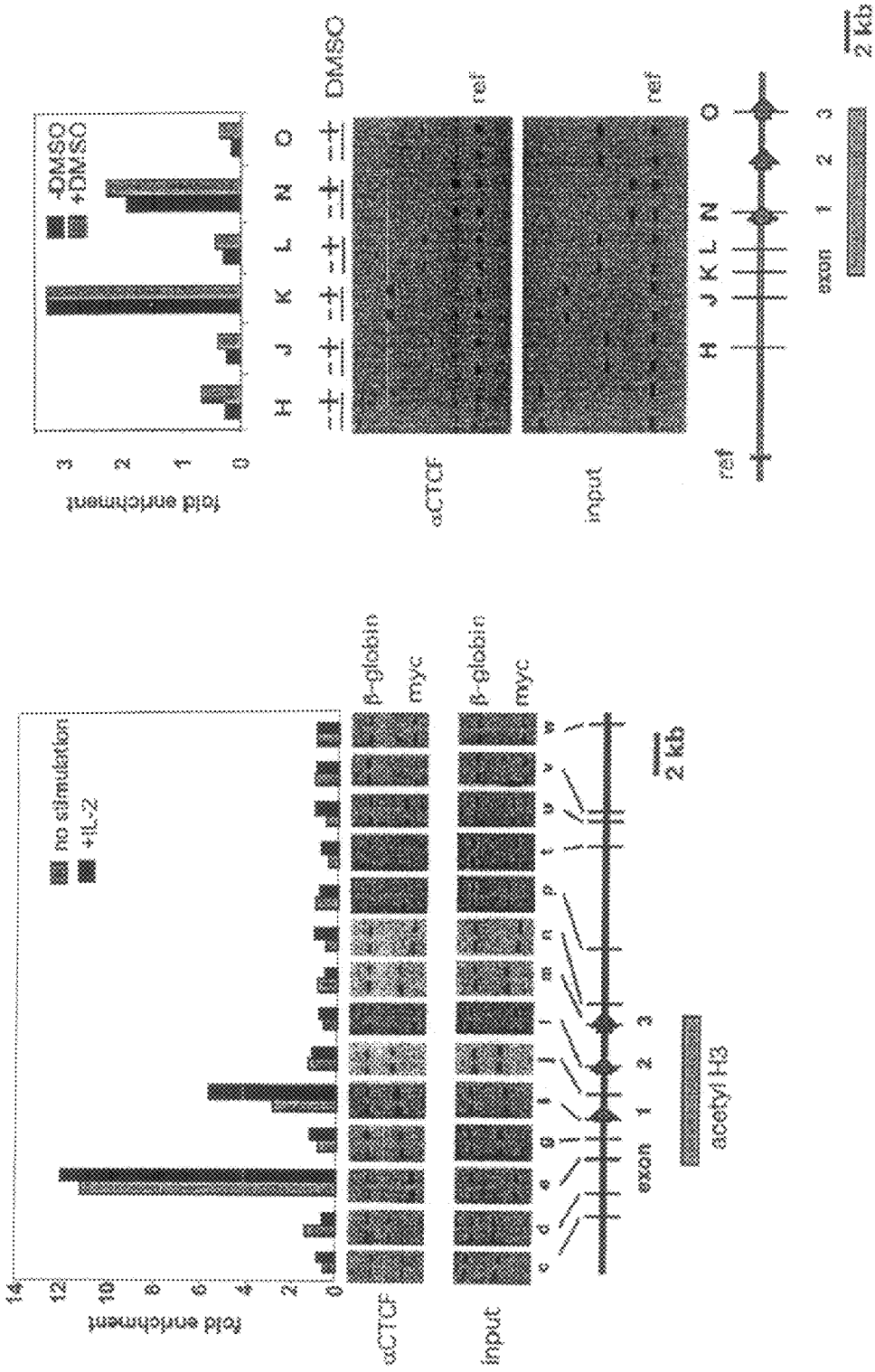

RECOMBINANT VECTORS FOR USE IN POSITION-INDEPENDENT TRANSGENE EXPRESSION WITHIN CHROMATIN

CROSS-REFERENCE TO RELATED APPLICATION

This application is a divisional of now abandoned patent application Ser. No. 11/009,389, filed Dec. 10, 2004 now abandoned, which is a continuation-in-part of now abandoned patent application Ser. No. 10/853,581, filed May 24, 2004, which claims the benefit of provisional Application No. 60/473,109, filed May, 23, 2003.

SEQUENCE PROGRAM LISTING APPENDIX

Two identical CDs identified as "Copy 1 of 2" and "Copy 2 of 2," containing the sequence listing for the present invention, is included as a sequence listing appendix.

TECHNICAL FIELD

This present invention relates to recombinant DNA technology involving compositions containing DNA elements identified within the mammalian c-myc loci that enables more efficient transgene expression. Methods for the application of the compositions to develop various expression vectors that are useful for enhancing transgene expression in eukaryotic hosts are also provided.

BACKGROUND OF THE INVENTION

Eukaryotic gene expression is governed at multiple levels, involving local modes of regulation with short-range effects and global modes of regulation effective over extended distances. Within the transcriptional unit of a gene, cis-acting regulatory elements, such as promoters and enhancers, are positioned locally to efficiently recruit the transcriptional machinery to the DNA template to enable the transcription of the gene to an RNA product. Eukaryotic genes may be arranged in a linear sequence within chromosomes that are structurally and functionally subdivided into either transcriptionally active or transcriptionally inactive states. Heterochromatin comprises transcriptionally inactive domains consisting of highly condensed DNA/Histone complexes that are insensitive to DNase I treatment. Euchromatin comprises transcriptionally active domains with complexes of DNA/Histones less densely packed than in heterochromatin that are sensitive DNase I treatment.

Transcriptionally active and inactive regions of the genome are structurally distinguishable due to differential post-translational states that result from various modifications of DNA-associated histones by acetylation, methylation, phosphorylation, and ubiquitinylation. These modifications can be essential for tissue-specific regulation of gene expression, especially during differentiation processes. Euchromatin has been shown to correlate with the hyperacetylation of associated histones. In particular, the acetylation of several lysine residues and the methylation of lysine 4 in histone H3 are characteristic features of transcriptionally active genes. Transcriptionally inactive regions, by contrast, are organized into heterochromatic structures that are characterized by deacetylation of H3 and H4, and lysine 9 methylation of H3. The existence of eukaryotic genes within dynamic chromatin states contributes significantly to the phenomenon of position-effect variegation that frequently precludes stable, long-term heterologous gene expression upon random integration of exogenous DNA into a host chromosome. Because a substantial portion of the eukaryotic genome exists in the transcriptionally inactive heterochromatin state, random integration of exogenous genes into a heterochromatin environment likely results in transgene silencing. For example, gene therapy has only been partially successful, because of position-effect variegation that results from random insertion of transgenes into heterochromatin regions, leading to transgene suppression [G. H. Karpin, Curr. Opin. Genet. Dev. 4: 281-291 (1994)].

Unpredictable and low yields in recombinant protein production, which significantly reduces the rate at which therapeutic proteins are brought to the market, have also been attributed to position-effect variegation. Production yields from cultivated mammalian cells, and from transgenic plants and animals, are still not sufficient to meet growing demands. It is estimated that tons of human serum albumin are needed annually, which are currently produced by processing 50,000 liters of human plasma. Several hundred kilograms of proteins, such as collagen, thrombin, and recombinant therapeutic antibodies, are in demand on a global scale, but the demand has not been fulfilled [Florian M. Wurm, Nature Biotechnology 21: p34-35 (2003)]. There is a continuing need for improvements in recombinant technologies, in particular, improvements in vector designs for enabling more robust expression of heterologous genes within a chromatin environment, such as stably integrated exogenous genes within a host chromosome. Expression vectors that can improve the predictability, yield, and stability of protein expression are of significant value to the biotechnology industry and the biomedical community.

SUMMARY OF THE INVENTION

In various embodiments of the present invention, compositions and methods for using DNA sequences identified from human and murine c-myc loci are provided. Nucleic acid molecules with these DNA sequences are useful for facilitating stable expression a transgene. Various embodiments of the present invention are directed to recombinant expression vectors that include the present-nucleic-acid-molecule compositions of the present invention, and that can be incorporated into eukaryotic cell-lines, artificial chromosomes, transgenic animals, and transgenic plants to improve the production of recombinant proteins in a broad range of eukaryotic hosts. Pharmaceutical compositions that include the nucleic-acid-molecule compositions of the present invention within expression vectors are also useful for gene therapy in the treatment of various genetic diseases.

In one embodiment, the nucleic-acid-molecule compositions of the present invention can function as barrier elements that preclude silencing of transgenes by stabilizing host heterochromatin, and that enhance transgene expression levels when incorporated into expression vectors that further include a transgene, a promoter, and/or an enhancer. Expression vectors including the nucleic-acid-molecule compositions of the present invention can be inserted into an artificial chromosome or a chromosome of a host cell to improve transcriptional efficiency.

In another embodiment, the nucleic-acid-molecule compositions of the present invention can function as insulating elements that facilitate transcriptional efficiency by blocking enhancer-promoter interactions, and that preclude the effect of neighboring regulatory sequences when incorporated into expression vectors that further include a transgene, a promoter, and/or an enhancer.

In another embodiment, the nucleic-acid-molecule compositions of the present invention can mediate the attachment of chromatin to a nuclear matrix, and can facilitate the regulation of transcription when incorporated into an expression vector that further includes a transgene, a promoter, and/or an enhancer. The compositions of the present invention are directed to several, discrete, cis-acting regulatory elements, that include a barrier element, an insulating element, a silencing element, and matrix-attachment regions ("MAR"), which have not been previously characterized. Each nucleic-acid-molecule compositions of the present invention can be used individually, can be combined together in various combinations, and can be used with heterologous insulators and MARs in various combinations within a broad vector-design scheme for which stable transgene expression in a chromatin environment is desired.

BRIEF DESCRIPTION OF DRAWINGS

FIG. 4 illustrates a hypothetical example of a retroviral vector that includes MINE, MYC-5'MAR, and MYC-3'MAR.

FIG. 6A shows mapping of two CTCF-binding sites within the 5'boundary of murine c-myc, as described in Example 2.

FIG. 6B shows in vivo mapping of two CTCF-binding sites within the 5'boundary of human c-myc, as discussed in Example 2.

DETAILED DESCRIPTION OF THE INVENTION

Figure 1:
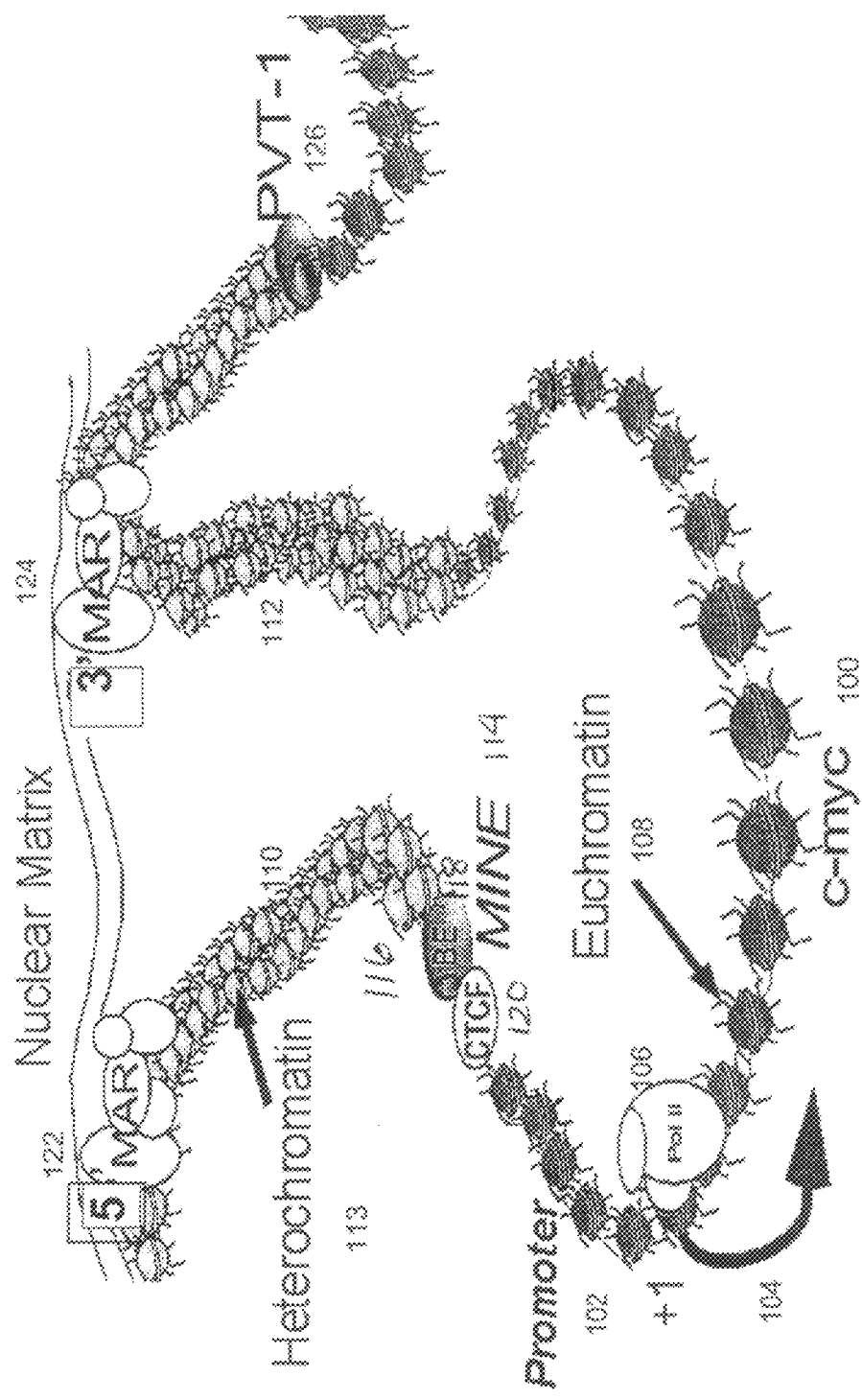
FIG. 1 illustrates various cis-regulatory elements of the present invention isolated from human and murine c-myc locus.

Embodiments of the present invention are directed to several, discrete nucleic acid molecules, referred to below as "the present nucleic acid molecules," isolated from conserved regions at the 5' and 3' boundaries of both murine and human c-myc gene loci. By incorporating the present nucleic acid molecules into an expression vector, the present nucleic acid molecules are useful for facilitating the stable expression of any prokaryotic or eukaryotic exogenous gene, or transgene, of interest. Various embodiments are directed to recombinant expression vectors including the present nucleic acid molecules, that can be incorporated into artificial chromosomes within cultured eukaryotic cell-lines, and into chromosomes of eukaryotic cell-lines, non-human transgenic animals, and non-transgenic and transgenic plants, in order to improve recombinant protein production in a broad range of eukaryotic hosts. In other embodiments, pharmaceutical compositions including the present nucleic acid molecules within expression vectors are useful for gene therapy applications such as stem-cell therapy and tissue-engineering/tissue grafts for the treatment of various genetic diseases.

Various isolated nucleic acid molecules of the present invention confer various functions, including (1) barrier activity that inhibits the progression of heterochromatin into transcriptionally active gene loci, (2) insulating activity that blocks enhancer-promoter interactions, and (3) nuclear-matrix binding activity that regulates transcriptional efficiency. The incorporation of various nucleic acid molecules into transgene expression vectors can improve transgene expression levels, and is particularly suitable for transgenes that are randomly integrated into a host chromatin. Expression vectors comprising the present nucleic acid molecules can be inserted into an artificial chromosome or a genome of a host cell to improve transcriptional efficiency.

The present nucleic acid molecules provide many advantages. For example, because the c-myc gene is constitutively and ubiquitously expressed in most tissues of a eukaryotic organism, the activities of the present nucleic acid molecules derived from the c-myc gene are predisposed to supporting transcriptional activity in many cell types in a non-tissue-specific manner. Expression vectors including the present nucleic acid molecules, such as a c-myc Insulator Element ("MINE") and matrix attachment regions derived from the 5' and 3' region of a c-myc loci ("MYC-MARs"), can be expressed in a broad range of host cells. In contrast, expression vectors comprising the chicken HS4 element, which is derived within the erythroid specific b-globin locus, is not as universally applicable, since b-globin gene expression is specific to erythroid cells. The chicken HS4 element has been shown to be functional in only a limited number of cells [Walters et al, Mol. Cell Biol. May 19 (5):3714-26 (1999). Transgene expression mediated by the chicken HS4 has not shown long-term stability in tissues that are not of the erythroid lineage. However, the present MINE variants can be utilized in divergent cells types, and expression vectors comprising MINE variants can be used for a broad range of gene therapy application which are further described in Section III D.

FIG. 1 illustrates various cis-regulatory elements of the present invention isolated from human and murine c-myc locus. In FIG. 1, "c-myc" refers to the transcribed region of the c-myc gene (100), which is positioned downstream from an endogenous promoter (102). Arrow (104) marks an initiation site of transcription, which is shown occupied by RNA polymerase II transcriptional machinery (106). Transcribed regions within the transcriptional unit of c-myc consist of less-densely packed euchromatin (108). Regions that extend upstream (110) and downstream (112) from the transcribed region (100) and the promoter (102) are represented as a condensed form of heterochromatin (113).

Various embodiments of the present invention are directed to a c-myc insulator element ("MINE") (114), located at the 5'-boundary (116), which is positioned within a transitional region between euchromatin and heterochromatin at the 5' end of the c-myc gene locus. The MINE comprises four sub-elements, including two main sub-fragments referred to as "BE" (118) and "CTCF" (120). The BE sub-fragment (118) represents the region of MINE that confers barrier activity. The CTCF sub-fragment (120) contains the 5'CTCF-binding site located within the 5'-boundary region.

Other elements, embodied in the compositions, relate to the identification and isolation of MYC-5'MAR (122) and MYC-3'MAR (124), which are distinct, nuclear matrix-associated regions located within two discrete regions of the heterochromatin domains flanking the transcribed sequences, i.e., c-myc gene (100). The MYC-5'MAR (122) is located approximately 76 kb upstream, and the MYC-3'MAR (124) is located approximately 32 kb downstream, from the c-myc locus. The MYC-5'MAR is positioned between the euchromatin domain of c-myc and the nearest neighboring gene (NCBI, accession number XM_299806) located 85 kb upstream of c-myc. The MYC-3'MAR is positioned between the euchromatin domain of c-myc and the PVT-1 gene (126), located 60 kb downstream of c-myc gene.

The embodiments of the present disclosure are discussed in the following order. Section I provides definitions. Section II provides functional characterizations for the cis-regulatory elements that includes a MINE, a BE, a 5'CTCF-binding site, and 5' and 3'-MYC-MARs. Section III provides advantages and various embodiments of the present invention that include variants of MINE and MYC-MARs, various expression vector constructs, and practical applications for these variants. The references listed are incorporated herein by reference.

I. Definitions

The term "heterochromatin" refers to transcriptionally inactive regions of a chromosome consisting of highly condensed DNA/Histone complexes that are insensitive to DNAse I treatment. Heterochromatin can be characterized by detecting the deacetylation states of Histone 3 and Histone 4 and the methylation state of Histone 3 at lysine 9.

The term "position-effect variegation" refers to a phenomenon that occurs when a transgene becomes transcriptionally silenced, or transcriptionally inactivated, upon random integration within the heterochromatin of a host.

The term "operably linked" refers to the joining of distinct DNA molecules, or DNA sequences, to produce a functional transcriptional unit.

The terms "gene," "gene of interest," and "transgene" are used interchangeably in the present disclosure. Generally, the terms refer to a deoxyribonucleotide (DNA) molecule, or a DNA sequence, that contains a coding sequence for a particular polypeptide. For example, a "transgene" may refer to the coding sequence for a recombinant protein of interest such as a therapeutic antibody. A transgene may contain heterologous sequences to encode a fusion protein. A "gene," "gene of interest," and "transgene" are not intended to include polyadenylation sites, promoters, enhancers, insulators, and MARs.

The term "upstream" refers to a relative direction or position with respect to a reference point along a linear nucleic acid molecule, or a nucleic acid sequence, towards the 5' end of a nucleotide sequence. "Upstream" may be used interchangeably with "5'".

The term "downstream" refers to a relative direction or position with respect to a reference point along a linear nucleic acid molecule, or a nucleic acid sequence, towards the 3' end of a nucleotide sequence. "Downstream" may be used interchangeably with "3'".

The term "promoter" refers to a nucleic acid molecule, or a nucleic acid sequence, that is typically positioned upstream of a gene and that recruits transcriptional machinery, such as the RNA polymerase and associated factors, that, in turn, initiates transcription of the gene.

The term "enhancer" refers to a nucleotide molecule, or a nucleic acid sequence, that can recruit transcriptional regulatory proteins, such as transcriptional activators, to enhance the transcriptional activation of a gene. Enhancer elements from heterologous sources can be used as a component within expression vectors that represent embodiments of the present invention. Some enhancers can operate in any orientation with respect to a particular heterologous transgene, and enhancers may be positioned upstream or downstream of a gene.

The term "orientation" refers to a particular order in the placement of a nucleic acid molecule, or a nucleic acid sequence, in the context of a DNA sequence. A linear DNA sequence can have, at a given point in time, one of two possible orientations: a 5'-to-3' orientation or a 3'-to-5' orientation. Generally, relative to a horizontal reference molecule/sequence, the orientation of a second horizontal nucleic acid molecule/sequence may be the same, or may be reverse or inverted.

The terms "expression vector," or "vector," refer to a nucleic acid vehicle that contains a combination of recombinant DNA sequence components for enabling transgene expression. An expression vector enables transport of a combined DNA sequence as an entity. Expression vectors embodied by the present invention include: episomes that are capable of extra-chromosomal replication, such as a circular, double-stranded DNA plasmid; a linearized double-stranded DNA plasmid; and other expression vectors that can serve equivalent functions.

Figure 2:
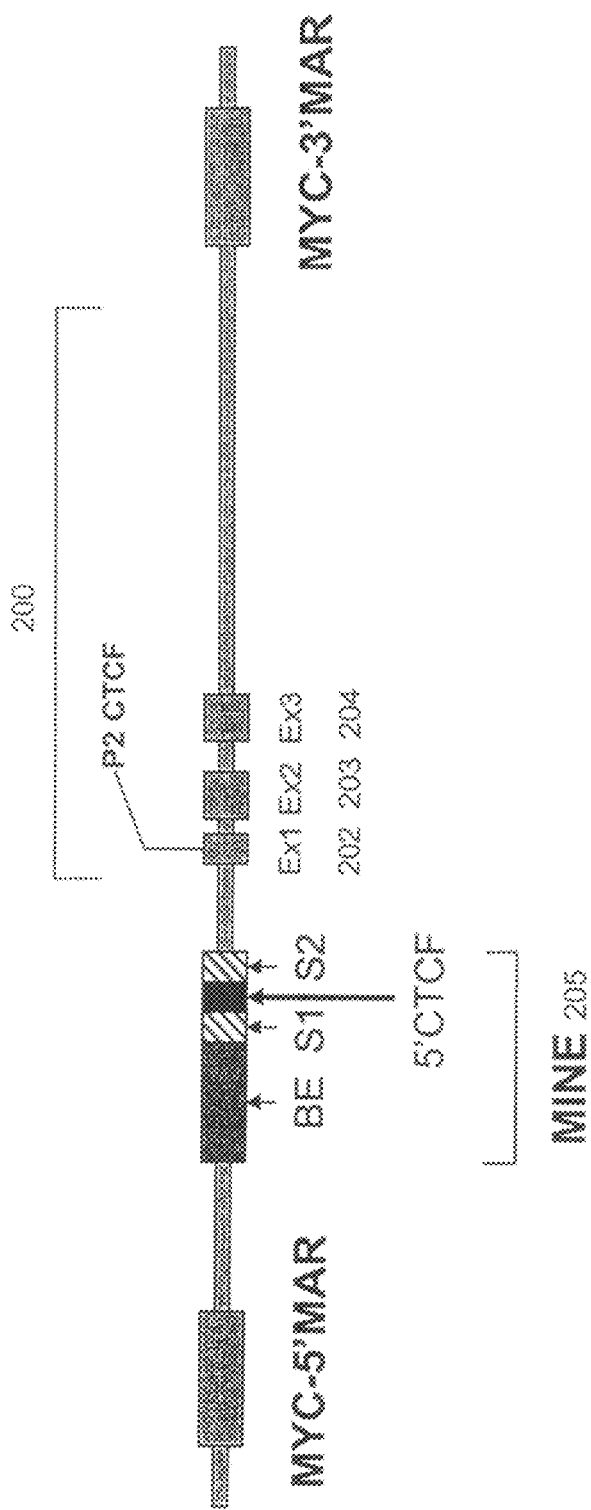
FIG. 2 provides a linear schematic of c-Myc Insulator Element ("MINE"), MYC-5'MAR, and MYC-3'MAR. Subfragments BE, S1, 5'CTCF, and S2 within MINE are also illustrated.

The term "flanking" refers a relative position of one nucleic acid sequence with respect to another nucleic acid sequence. A flanking sequence proceeds or follows a flanked sequence but need not be contiguous with, or immediately adjacent to the flanked sequence. For example, in the context of a transcription unit comprising a promoter and a transgene, a MINE may be placed within an upstream flanking region of the transcription unit. A MYC-3'MAR may be placed within a downstream flanking region of the transcription unit. FIG. 2 illustrates an exemplary placement of these components.

The terms "homology," "identity," and "similarity" refer to the degree of sequence similarity between two polypeptides or between two nucleic acid molecules being compared by sequence alignment. The degree of homology between two discrete nucleic acid sequences being compared is a function of the number of identical, or matching, nucleotides at comparable positions. The degree of homology between two discrete amino acid sequences being compared is a function of the number of identical, or matching, amino acids at comparable positions.

II. Identification of Cis-Regulatory Elements at the c-Myc Gene Loci

Figures 5A, 5C:
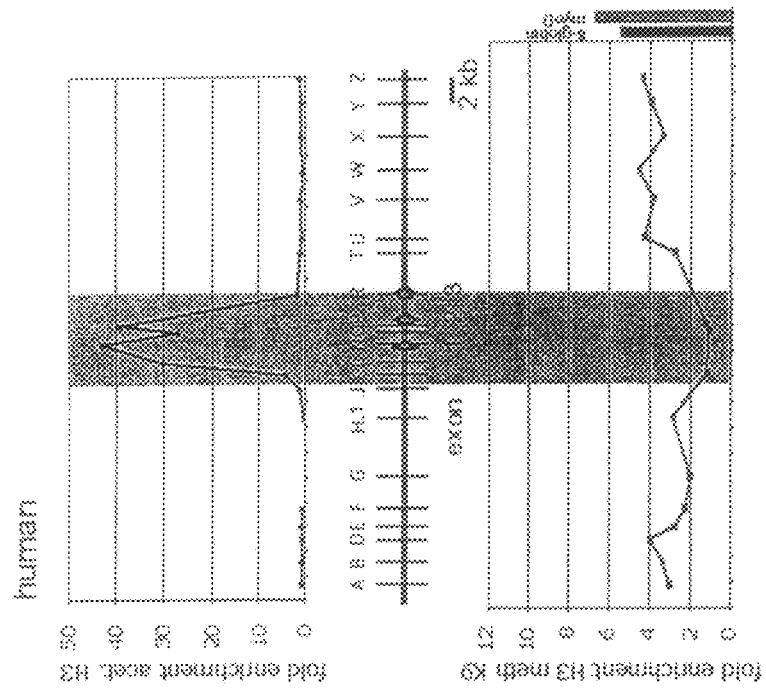
FIG. 5A shows mapping of histone acetylation patterns at the murine c-myc gene loci, as described in Example 1.
FIG. 5C shows mapping of histone acetylation patterns at the human c-myc gene loci, as described in Example 1.
Figures 5B, 5D:
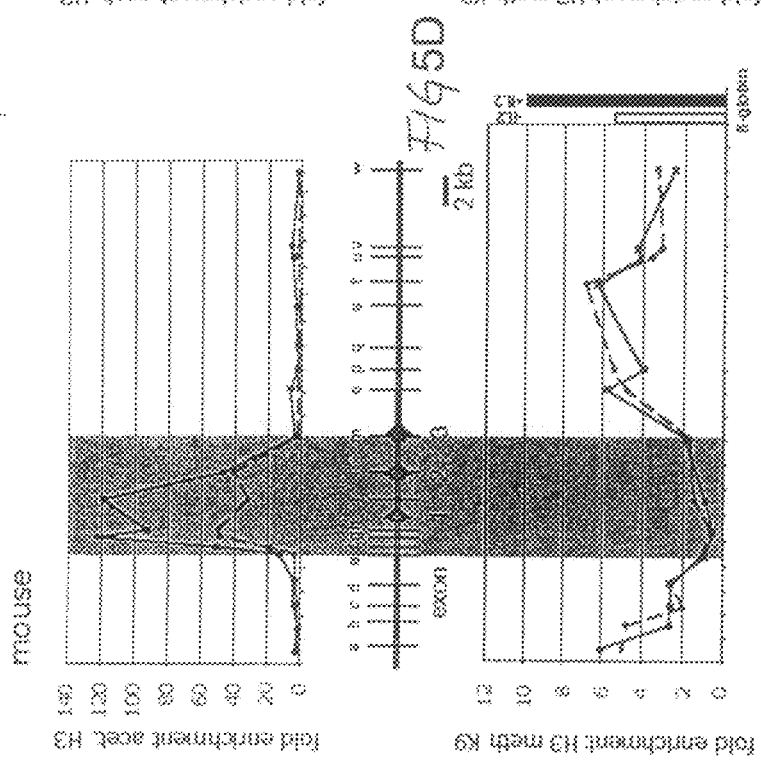
FIG. 5B shows independent mapping of histone methylation patterns at the murine c-myc gene loci, as described in Example 1.
FIG. 5D shows independent mapping of histone methylation patterns at the human c-myc gene loci, as described in Example 1.

The present inventors have isolated cis-regulatory elements, discussed below at the human and mouse c-myc loci, and have characterized the respective functions of each element [Wendy M Gombert, Stephen D. Farris, Eric D. Rubio, Kristin M. Morey-Rosler, William H. Schubach, and Anton Krumm, "The c-myc-Insulator Element and Matrix Attachment Regions Define the c-myc Chromosomal Domain," Molecular and Cellular Biology, Vol. 23, No. 24, p. 9338-9348 (2003), which is incorporated by reference]. Methods used to establish boundaries between euchromatic and heterochromatic domains at the human and mouse c-myc locus are provided in Example 1. FIG. 5A shows the mapping of histone acetylation and methylation patterns at the murine c-myc gene loci, as described in Example 1. FIG. 5B shows the independent mapping of histone acetylation and methylation patterns at the human c-myc gene loci, as described in Example 1. The following provides a brief description of each nucleic acid molecule claimed, and various functions conferred by each molecule. The referenced Example sub-sections provide a more complete description.

A. Isolation and Characterization of c-Myc Insulator Elements ("MINE")

DNA sequences, referred to as "insulators," have evolved as a complementary mechanism for structurally and functionally distinguishing regions of euchromatin from heterochromatin. In their native context, insulator elements are peripherally positioned with respect to a given transcriptional unit. Insulators function by establishing boundaries between neighboring transcriptional units to prevent encroachment by neighboring regions of heterochromatin. Insulators also serve as efficient gatekeepers in permitting or preventing access to a transcription unit by transcriptional regulatory proteins. Insulating elements are thought to serve at least two functions: (1) to provide a protective shield against deleterious effects of neighboring enhancer regions on the transcriptional activity of a gene, and (2) to facilitate or to amplify the activity of distantly positioned, multi-element enhancer complexes within a transcriptional unit, such as the Locus Control Regions of the β-globin gene.

Insulators, originally identified in *Drosophila* and subsequently found in yeast and vertebrate cells, protect transcriptionally active regions from the silencing effects of inert chromatin. In fission yeast, the deletion of boundary elements that are positioned at the borders of silenced domains and that separates euchromatin from heterochromatin results in the spreading of K9-methylated H3, a characteristic of heterochromatin, into neighboring euchromatin sequences. When insulator elements isolated from flies, such the scs/scs' and gypsy elements, are placed between an enhancer and a promoter, these insulator elements can associate with DNaseI-hypersensitive sites, block enhancer-promoter interactions, and provide position-independent expression of exogenous genes, or transgenes. Insulator elements, identified within yeast telomeres and within rDNA and HMR loci, also confer protective properties against negative influences from surrounding heterochromatin. Within the chicken β-globin locus, a barrier function is conferred by the insulator HS4 element ("cHS4"), which includes a binding site for CTCF, a 11-zinc-finger protein. The barrier activity of cHS4 associates with a peak in histone acetylation over the insulator element, which is independent of the expression status of the transcribed gene [Recillas-Targa et al., Proc. Natl. Acad. Sci. U.S.A. 99: 6883-88 (2002)].

1. Characterization of Enhancer-Blocking and Barrier Activities of c-Myc INsulator Element (MINE)

FIG. 2 provides a linear schematic of c-myc insulator element ("MINE"), MYC-5'MAR, and MYC-3'MAR. In FIG. 2, coding regions are shown within the transcriptional unit of the c-myc gene (200) that include several exons: exon 1 (202), exon 2 (203), and exon 3 (204). The MINE (205) was originally identified within a 1.9 kb region (SEQ ID NO: 1), flanked by SpeI and Csp6I sites. The MINE was subsequently mapped to a smaller 1.6 kb region within a hyperacetylated region, approximately 2 kb upstream of c-myc exon 1, near the transition site from lysine 9-methylated histones to hyperacetylated histones (see Example 3).

Figure 7:
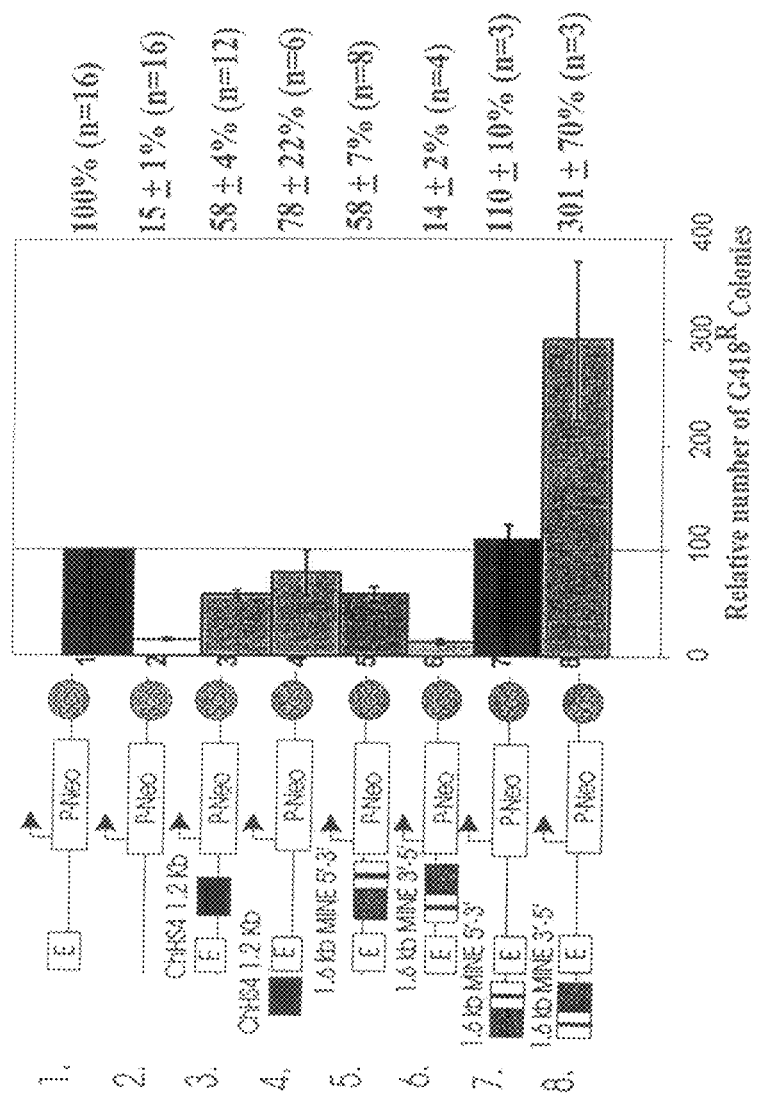
FIG. 7 shows in vivo mapping of the enhancer-blocking and barrier activities of MINE, as described in Example 3.

To determine the functional activity of the 1.6 kb MINE (SEQ ID NO:2) isolated from the 5' boundary of human c-myc gene, the MINE was placed at variable positions relative to an exogenous enhancer and promoter that are contained within several transcription-specific, reporter expression cassettes with a selectable marker as an exemplary transgene (see Example 3). Random integrations of an expression vector comprising a 1.6 kb region of MINE into the chromatin of an eukaryotic host demonstrated that the MINE confers at least three functional activities: (1) an enhancer-blocking activity; (2) a heterochromatin barrier activity; and (3) a transcriptional silencing activity. FIG. 7 shows the mapping of the enhancer-blocking and barrier activities of MINE, as described in Example 3. Based on sequence homology to the human MINE, a comparable MINE sequence was identified at the 5'boundary of mouse c-myc (SEQ ID NO:9).

FIG. 7 also shows the positional effect of MINE on the transcriptional activation of a selectable marker reporter gene, measured after stable, random integration of an expression cassette obtained by introducing a MINE into host chromatin. When the 1.6 kb MINE fragment, derived from the c-myc 5'boundary (−1.7 kb to −3.3 kb relative to exon 1) is placed between a tissue-specific TCRδ-enhancer and a Vδ-promoter within the expression cassette, the enhancer activity is inhibited. In contrast, when MINE was positioned upstream of the enhancer, the enhancer-inhibition activity was not observed. The enhancer-blocking activity of MINE is analogous to that of the 1.2 kb chicken β-globin HS4 insulator element (SEQ ID NO: 13), which in this study and previous reports demonstrated a similar enhancer-blocking activity [Bell et al., Cell, Vol. 98, p. 387-396].

The orientation specificity of MINE was tested by inserting the 1.6 kb fragment between the enhancer and promoter elements in s reverse orientation to reporter constructs. Unexpectedly, MINE blocked enhancer-promoter interaction more efficiently in the 3'to-5' orientation compared to the alternative, 5'-to-3' orientation. Thus, these experiments show that MINE provides at least two functional activities, an enhancer-blocking activity and a barrier activity, both of which are integral to the proper functioning of the 5'boundary of c-myc (see FIG. 7, Example 3).

Thus, when an expression vector comprising a MINE sequence is integrated into an eukaryotic host chromatin, the barrier activity of MINE can be used to protect against position-effect variegation that often results in transgene silencing, or that precludes robust transgene expression. The enhancer-blocking activity of MINE enables MINE-containing expression vectors to shield against the deleterious activity of neighboring enhancers that may have long-range, over-reaching effects on neighboring transcriptional units. Various embodiments are directed to compositions comprising a MINE (human, SEQ ID NO:1; mouse, SEQ ID NO: 9), which are further described in Section III.

2. Characterization of Activities of MINE Sub-Fragments Comprising a Barrier Element (BE), 5'CTCF-binding Site, and Silencing Elements S1 and S2

In FIG. 2, the 1.9 kb MINE (205) comprises two sub-regions: a barrier element "BE" (206) and a CTCF fragment (214). The CTCF fragment (214) is defined by HindIII and Csp6I sites (a 640 bp fragment, spanning nucleotides 1254 to 1893 of human SEQ ID NO: 1), and includes the silencing elements "S1" (208) and "S2" (210), and 5'CTCF-binding site "5'CTCF" (212). FIG. 2 provides a detailed map of the 1.9 kb MINE (SEQ ID NO:1) comprising BE, S1, 5'CTCF-binding site, and S2. The strength of MINE as a boundary element is attributed to at least three discrete activities that have been identified within these sub-regions of MINE: a silencing activity, an enhancer-blocking activity, and a barrier activity.

FIGS. 8A-C show the sub-mapping of multiple functional activities within MINE, particularly the activities conferred individually by the 5'CTCF-binding element and the BE, as described in Examples 4 and 5.

(a) Barrier Activity of BE

The BE is defined within a 1.0 kb fragment flanked by SpeI and HindIII restriction sites, and is designated as SEQ ID NO:3, which is a sub-fragment of SEQ ID NO:1 (1-1256). To determine BE function, the 1 kb BE fragment (FIG. 8A, Construct 7) was inserted into a parent reporter construct E-P-neo-scs' (described in Example 3). Expression cassettes comprising a BE (SEQ ID NO:3) placed upstream of an enhancer can enhance the expression level of a transgene, when randomly integrated into host chromatin. However, expression cassettes comprising a BE placed between an enhancer and a promoter do not affect the transgene expression level, when randomly integrated into host chromatin. Thus, the barrier activity observed in MINE is attributed to BE. Various embodiments are directed to compositions comprising a BE (human SEQ ID NO: 3; mouse SEQ ID NO:10), which are further described in Section III.

(b) In Vivo CTCF-binding Activity at the 5'boundary of c-myc

The CTCF fragment is a 640 bp fragment ((214), FIG. 2) containing one 5'CTCF-binding site that is located −2.0 kb upstream (in human) or −1.9 kb upstream (in mouse) from Exon 1 (202) close to a DNAse hypersensitive region I. FIG. 6A shows the in vivo mapping of two CTCF-binding sites within the 5' region murine c-myc (see Example 2). FIG. 6B shows the in vivo mapping of two discrete CTCF-binding sites within the 5'region of human c-myc (see Example 2). The 5' region of both human and mouse c-myc are able to bind CTCF in vivo, which is mediated by two CTCF-binding sites (Table 2, Example 2): (1) the 5'CTCF-binding site within the 640 bp CTCF fragment (human SEQ ID NO:15; mouse SEQ ID NO:16); and (2) the CTCF-binding site within site A promoter 2 region ("P2") (human SEQ ID NO: 20; mouse SEQ ID NO:21). Both are constitutively bound in vivo by the CTCF protein, a transcriptional activator. The present inventors are the first to characterize the in vivo binding activity of the 5'CTCF-binding site (human SEQ ID NO: 15; mouse SEQ ID NO: 16) in human and mouse, and are first to determine the contribution of the 5'CTCF-binding activity to the insulating function of the MINE. Note that human 5'CTCF-binding site represents nucleic acids 1604 to 1643 within SEQ ID NO:1. Note that mouse 5'CTCF-binding site represents nucleic acids 1659 to 1693 within SEQ ID NO:9.

FIG. 8A illustrates expression vectors comprising various sub-fragments of the CTCF fragment containing either a wildtype CTCF-binding site or a mutant CTCF-binding site (see Example 2, Table 2). Expression vectors comprising the 5'CTCF-binding site (human SEQ ID NO:15; mouse SEQ ID NO:16) derived from MINE placed between an enhancer and a promoter, exhibit enhancer-blocking properties, when randomly integrated into host chromatin, as described in Example 4. Various embodiments are directed to compositions comprising the human 5'CTCF-binding site sequence (human SEQ ID NO: 15; mouse SEQ ID NO: 16), which are further described in Section III, below.

(c) Silencing Activity of "S1" and "S2"

Also within the 640 bp CTCF fragment ((214), FIG. 2), two sub-regions "S1" and "S2" within the flanking regions of the 5'-CTCF binding site (human SEQ ID NO:15; mouse SEQ ID NO:16) have been characterized. The human S1 is designated as SEQ ID NO:4, and is a sub-fragment of SEQ ID NO:1. The human S2 is designated as SEQ ID NO:5, and is a sub-fragment of SEQ ID NO:1.

Figure 8:
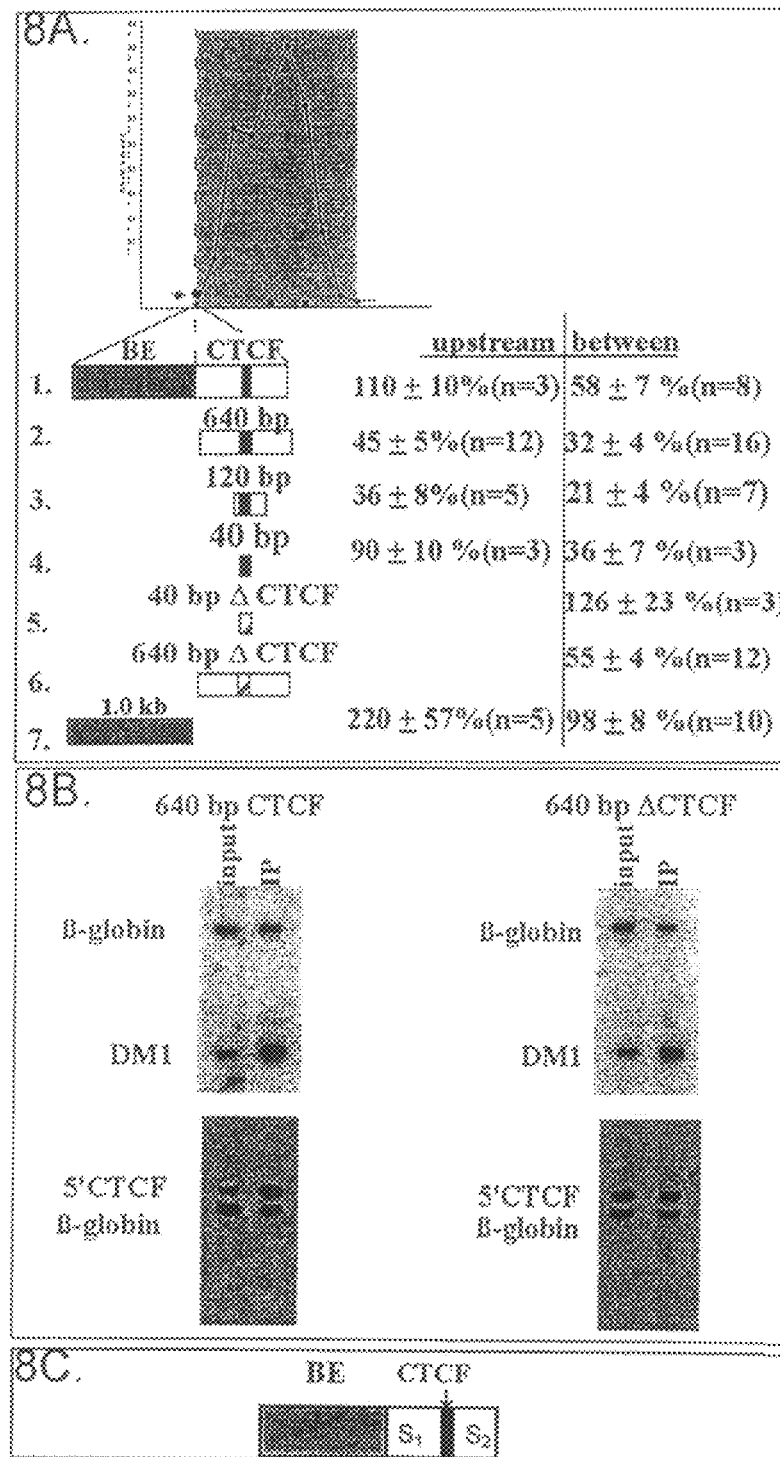
FIGS. 8A-C show sub-mapping of multiple functional activities within MINE, particularly the activities conferred individually by the 5'boundary CTCF-binding element and the BE fragment, as described in Examples 4 and 5.

S1 and S2 confer the silencing properties of MINE when positioned upstream of enhancers, as described in Example 4 and FIG. 8. Various embodiments are directed to compositions comprising S1 sequences (human SEQ ID NO:4) and S2 sequences (human SEQ ID NO:5), which are further described in Section III, below. Various embodiments of the present invention are directed to compositions comprising comparable sequences that have been identified in murine S1 (SEQ ID NO:207) and murine S2 (SEQ ID NO:208), which are further described in Section III.

B. Nuclear-Matrix-Attachment Activity of 3' and 5' MYC-MARs

Matrix attachment regions ("MARs"), or scaffold attachment regions ("SARs"), affect gene regulation by mediating the anchoring of chromatin fibers to the nuclear matrix through AT-rich DNA sequences. Proteins bound to these elements recognize structural features such as narrow minor grooves, DNA bends and kinks, and topoisomerase II cleavage sites. The association of the MARs with some enhancers [Scheuermann and Garrard., Crit. Rev. Eukaryot. Gene Expr. 9: 295-310 (1999)] suggests that they participate in long-range control of gene expression by facilitating the activity of enhancers. However, MARs of the chicken lysozyme gene and the human apolipoprotein B ("apo B") gene are not associated with enhancer sequences [Kalos and Fournier., Mol. Cell. Biol. 15: 198-207 (1995); Wang et al., J. Lipid Res. 37: 2117-14 (1996)].

Figure 9:
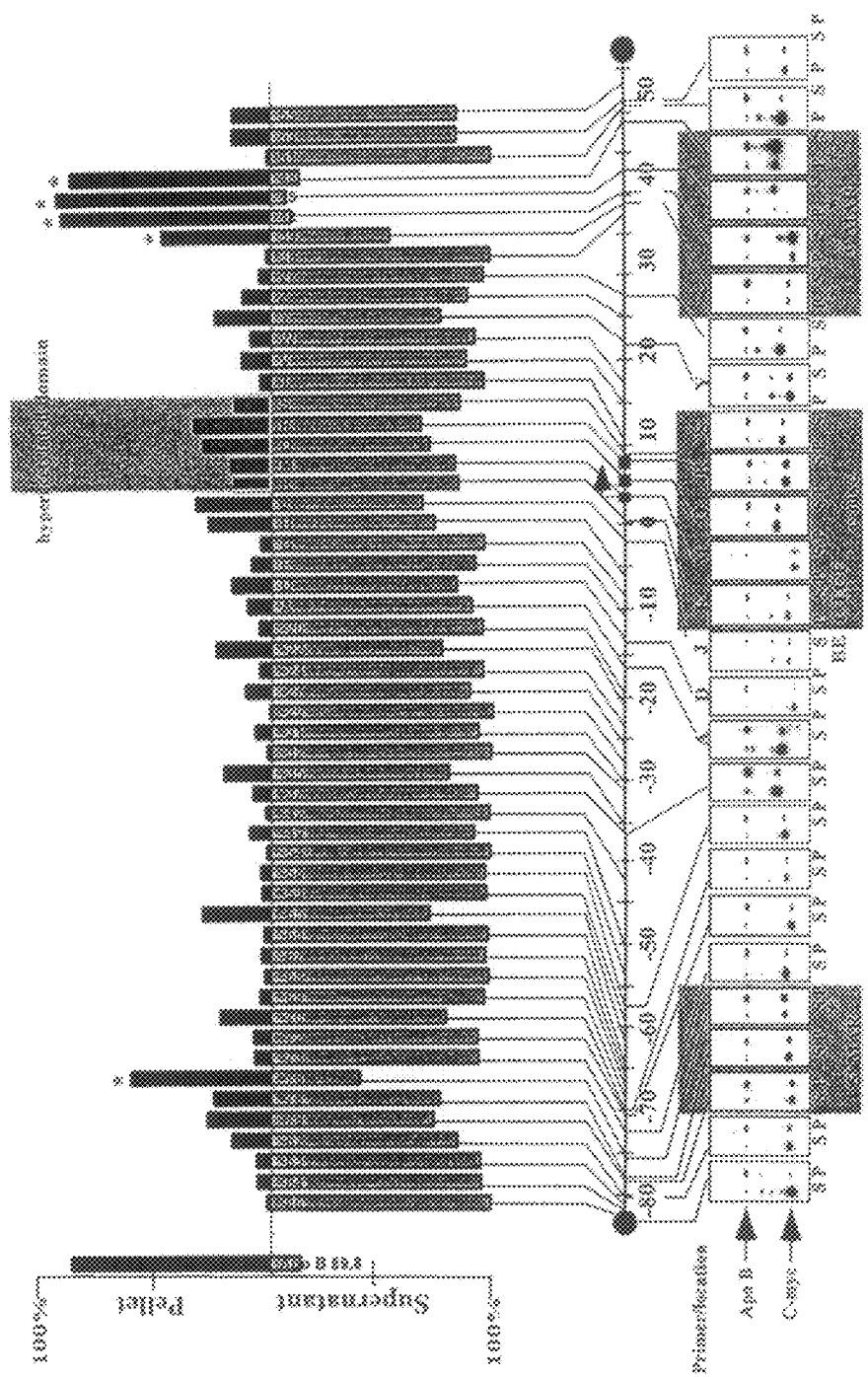
FIG. 9 shows mapping of two discrete matrix attachment regions at the 5'end and 3'end of c-myc locus, as described in Example 6.

FIG. 9 shows the mapping of two discrete matrix attachment regions at the 5'end and the 3'end of the c-myc locus, as described in Example 6. Both MYC-MARs associate strongly with the nuclear matrix. The MYC-MARs comprise a greater-than-160-kb domain in which the transition between euchromatin and heterochromatin regions is maintained by insulator elements such as MINE.

The human MYC-5'MAR (SEQ ID NO:6) was identified within a 3.4 kb region flanked by XbaI and EcoRI restriction sites. The MYC-5'MAR is positioned 76 kb upstream of the 5'-end of c-myc gene. The nuclear-matrix binding activity of the mouse MYC-5'MAR (SEQ ID NO:11) was independently identified by the present inventors within a comparable region flanked by XbaI and EcoRI restriction sites.

The human MYC-3'MAR is designated as SEQ ID NO:7, and comprises a sub-region (SEQ ID NO:8) that appears to be unique to the 3' boundary of human c-myc. The MYC-3'MAR is located 32 kb downstream of the 3'end of the c-myc. Various embodiments are directed to compositions comprising mouse MYC-5'MAR (SEQ ID NO:11), and mouse MYC-3'MAR (SEQ ID NO:12), which are further described in the following Section III, below.

A functionally comparable region also exists within the 5' boundary of murine c-myc loci (mouse MYC-5'MAR designated as SEQ ID NO: 11), and a conserved region (80% identity relative to human) within the 3' boundary of murine c-myc loci (mouse MYC-3'MAR designated as SEQ ID NO: 12). Various embodiments of the present invention, are directed to comparable mouse MYC-5'MAR, and mouse MYC-3'MAR identified at the boundary of mouse c-myc loci, which are further described in the following Section III, below.

III. Advantages of the Present Invention and Related Embodiments

The cis-regulatory elements that have been isolated and characterized by the present invention are positioned endogenously within the 5' and 3' regions of mammalian c-myc loci. The present inventors have shown that these nucleic acid elements may be removed from their native context and incorporated into various expression vectors. The present nucleic acid sequences that include a barrier element, an insulating element, a silencing element, and MYC-MARs, may be incorporated into a broad vector-design scheme in order to enhance the predictability and stability of recombinant protein production. Examples of various transgenes, promoters, and enhancers that may be incorporated within expression vectors that represent embodiments of the present invention are first provided. Examples of MINE and MYC-MAR variants that may be interchanged are provided. Examples of various heterologous insulators, barrier elements, and MARs that may be interchanged with MINE and MYC-MAR variants within expression vectors are provided. Examples of host cells that may be transfected or infected with various mechanisms of gene delivery are provided. Examples of various uses for expression vectors are provided.

A. Operable Transgenes, Promoters, and Enhancers

1. Trangenes

In general, an expression vector embodied by the present invention comprises a transcription unit that includes the coding region of a transgene of interest operably linked to a transcriptional regulatory element. A transgene of interest is any exogenous gene that encodes a polypeptide, the recombinant production of which is desired by a practitioner. A transgene may be a prokaryotic gene that encodes a prokaryotic polypeptide, or a eukaryotic gene that encodes a eukaryotic polypeptide. A transgene can be a chimeric molecule, comprising two or more distinct polynucleotide sequences that encode a fusion protein. The coding region of any gene may be used, for example, the cDNA of a transgene or the cDNA fragment of a transgene. Examples of suitable transgenes include structural proteins, enzymes, antibodies, membrane receptors, neurotransmitters, hormones, regulatory proteins, cytokines, antigens, and clotting factors. Stable and reproducible production of such therapeutic proteins over an extended period of time is highly desirable.

More than one transgene may be operably positioned under the transcriptional control of a promoter and/or an enhancer within a transcriptional unit by a person skilled in the art of molecular biology. More than one transcriptional unit may be included within an expression vector. The techniques for combining any DNA sequence of the present invention can be found in various sources, such as a standard laboratory molecular biology treatises [Sambrook et al., Molecular Cloning: A Laboratory Manual, 3d ed., 2001, Cold Spring Harbor, which is incorporated in its entirety]. Conventional techniques that are practiced in the art for recombinant engineering include the use of restriction enzyme digestion, nucleic acid ligation, and polymerase chain reaction (PCR).

2. Promoter and Enhancers

A transcriptional regulatory element of a transcriptional unit may include one or more promoters and enhancers. Generally, a promoter is positioned upstream of a transgene. In contrast, an enhancer can be placed upstream, downstream, or both upstream and down stream of a transgene. With respect to the transgene of interest, promoter and enhancer elements may be derived from a homologous source, for example, derived from the native gene locus of the transgene (i.e., the endogenous promoter of gene A may be operably linked to gene A within the vector). Alternatively, promoter and enhancer elements may be derived from a heterologous source such as from the same gene locus of a different species of an organism, from a different gene locus of the same species, or from a different gene locus of a different species of organism. A suitable promoter can be constitutive (i.e., transcriptionally activated at steady-state) or can be inducible (i.e., transcriptionally activated upon proper stimulus). Constitutive and inducible promoters are generally known by persons skilled in the art. Examples of constitutive promoters include various promoters derived from infectious viruses, such as retroviruses, herpes virus, lentivirus, adenovirus and adenovirus variants, mumps and poliovirus. Promoter and enhancer selection is generally independent of the particular transgene of interest, but is dependent on the presence or absence of host-specific factors, such as tissue-specific regulatory factors that are present within the nuclear compartment of a host cell. Promoter and enhancer selection can vary depending on the type of eukaryotic host cell in which the present expression vectors need to be operable, so that a given transgene can be expressed pursuant to host-chromatin integration. Examples of suitable host cells are provided below, and include eukaryotic animal and plant cells. Thus, operable promoters of the present invention include a broad range of constitutive, inducible, tissue-specific, non-tissue-specific, and developmentally-specific promoters that can be derived from animals, plants, and viruses, which can be activated, or recognized, by nuclear regulatory factors present within a eukaryotic host. Various promoters and methods for operably linking promoters to transgenes are known by persons skilled in the art of recombinant technology.

3. Additional Regulatory Elements

An expression vector can include one or more additional sequences necessary for transgene expression. For example, the expression vectors that represent embodiments of the present invention ("present expression vectors") can include a 3' untranslated sequence ("UTS"), such as a polyadenylation site that can be derived from the 3' end of most eukaryotic genes. Various polyadenylation sites can be positioned downstream of the transgene, including a 3' UTS derived from the native gene locus of the transgene of interest (i.e., homologous polyadenylation site), and heterologous sites. In addition, a 5' UTS element can be positioned upstream of a transgene of interest to enhance long-term transgene expression. With respect to the transgene, homologous 5' UTS derived from the endogenous transgene locus, or various heterologous 5' UTS can be used including, for example, a gamma-actin 5' UTS, an aldolase 5' UTS, an EF1-alpha 5' UTS, or a beta-actin 5' UTS. The length of a suitable 5' UTS sequence can extend up to 500 base pairs, but preferably between 25 to 150 base pairs. Alternatively, a heterologous U1 intron sequence can be positioned adjacently to the 5' UTS sequence, or fused to a 5' UTS region [Korb & Johnson, Nucleic Acids Res. 21(25):5901-8, (1993)] Examples of U1 introns include a EF1-alpha U1 intron, a GAPDH U1 intron, and a beta-actin U1 intron. Suitable 5' UTS sequences for the various genes are known by persons skilled in the art and can be readily identified by searching a reputable database, such as the GenBank database.

4. Selectable Marker Gene

An expression construct can also include the coding sequence for a selectable marker used to confer a selectable phenotype upon introduction into various mammalian cells. The selectable phenotype is used to identify and to isolate recipient primary or secondary cells. For example, a selectable marker which confers a selectable phenotype, such as drug resistance, nutritional auxotrophy, resistance to a cytotoxic agent, or expression of a surface protein, can be used. Examples of suitable selectable markers include genes that confer resistance to neomycin, puromycin, hygromycin, and histidine D. A selectable marker can be introduced into primary or secondary cells by incorporating the selectable marker gene within expression constructs comprising a transgene and the present nucleic acid sequences, or by incorporating the marker gene into a distinct vector than can be co-transfected for example, with the present expression constructs.

B. Use of MINE, MYC-MARs, and Variants of MINE and MYC-MARs within Expression Vectors 1. Expression Vectors Comprising c-Myc Insulator Element (a) Variants of MINE The various expression vectors described in the previous sub-section A can be embellished, or further incorporated, with the present nucleic acid sequences comprising MINE, sub-fragments of MINE, and homologous variants of MINE and sub-fragments. In one embodiment, the present expression vector comprises a MINE sequence, or a functionally equivalent sequence that includes sub-fragments of MINE, and are derived from the c-myc gene of any mammal. Examples of mammals include human, mouse, rat, monkey, horse, cat, dog, pig, cow, sheep, goat, and varying marsupials. MINE sequence variants exhibit activities that include: an enhancer-blocking activity, an insulating activity, a silencing activity, and a barrier activity. The homology between human MINE and murine MINE is approximately 90%, for example. The present embodiments are directed to variant sequences of MINE that have one or more activities associated with MINE, and that have at least 50%, 55%, 60%, 65%, 70%, 75%, 80%, 85%, 90%, and 95% identities.

In the described embodiments, a MINE, sub-fragments of MINE, and MINE sequence variants are positioned in a 5'-to-3' direction in the following order: a MINE, a enhancer, a promoter, and a transgene of interest. In addition, a MINE, sub-fragments of MINE, and MINE sequence variants can be positioned with respect to the enhancer, the promoter, and the transgene, in an orientation that is either 5'-to-3' direction, or 3'-to-5' direction. Furthermore, one or more molecules of MINE, sub-fragments of MINE, and MINE sequence variants may be used within an expression vector molecule.

In another embodiment, the present expression vectors comprise a human MINE sequence, including SEQ ID NO: 1, and sequences that have at least 50% identity with respect to SEQ ID NO: 1. In another embodiment, the present expression vector comprises a murine MINE sequence, including SEQ ID NO:9, and sequences that have at least 50% identity with respect to SEQ ID NO:9.

(b) Variants of BE

In another embodiment, the present expression vectors comprise a barrier element (BE), which is a sub-fragment of MINE, derived from the c-myc gene of any mammal. In a related embodiment, the present expression vectors comprise a human BE sequence, including SEQ ID NO:3, and sequences that have at least 50% identity with respect to SEQ ID NO:3. In a related embodiment, the present expression vectors comprise a murine BE sequence, including SEQ ID NO:10, and sequences that have at least 50% identity with respect to SEQ ID NO: 10.

(c) Variants of 5'CTCF-Binding Site

In another embodiment, the present expression vectors comprise a CTCF-binding site, which is a sub-fragment of MINE, derived from the c-myc gene of any mammal. In a related embodiment, the present expression vectors comprise a human CTCF-binding site, including SEQ ID NO: 15, and sequences that have at least 50% identity with respect to SEQ ID NO:15. In a related embodiment, the present expression vectors comprise a murine CTCF-binding site, including SEQ ID NO: 16, and sequences that have at least 50% identity with respect to SEQ ID NO: 16.

(d) Variants of S1 and S2

In another embodiment, the present expression vectors comprise two silencing elements, which are sub-fragments of MINE, derived from the c-myc gene of any mammal. In a related embodiment, the present expression vectors comprise a first human silencing element (S1), including SEQ ID NO:4, and sequences that have at least 50% identity with respect to SEQ ID NO:4. In a related embodiment, the present expression vectors comprise a second human silencing element (S1), including SEQ ID NO:5, and sequences that have at least 50% identity with respect to SEQ ID NO:5. In a related embodiment, the present expression vectors comprise a first mouse silencing element (S2), including SEQ ID NO:207, and sequences that have at least 50% identity with respect to SEQ ID NO:207. In a related embodiment, the present expression vectors comprise a second mouse silencing element (S2), including SEQ ID NO:208, and sequences that have at least 50% identity with respect to SEQ ID NO:208.

(d) Combination Variants of MINE

In one embodiment, the present expression vectors comprise any combination of mammalian MINE sub-fragments. In another embodiment, the present expression vectors comprise any combination of human and murine MINE sub-fragments. In another embodiment, the present expression vectors comprise one or more of any combination of the following sequences: SEQ ID NO:1; SEQ ID NO:2; SEQ ID NO:3; SEQ ID NO:4; SEQ ID NO:5; SEQ ID NO:9; SEQ ID NO:10, and sequences that have at least 50% identity with respect to SEQ ID NOS:1-5, 9, and 10.

2. Expression Vectors Comprising MYC-MARs ("MYC-5'MAR and MYC-3'MAR")

The various expression vectors described in the previous sub-sections A and B(1) can be embellished, or further incorporated, with the present nucleic acid sequences comprising MYC-5'MAR, MYC-3'MAR, sub-fragments of MYC-5'MAR and MYC-3'MAR, and homologous variants of MYC-5'MAR and MYC-3'MAR. In one embodiment, the present expression vector comprises a MAR sequence, or a functionally equivalent sequence that includes sub-fragments of MYC-5'MAR and MYC-3'MAR, that is derived from a c-myc locus of a mammal, and functions as a nuclear-matrix attachment region ("MAR") when inserted into a host chromosome. Exemplary mammalian sources for MINE also apply to MYC-MARs (Sub-section B (1)). In the described embodiments, MYC-5'MAR variants can be positioned 5' (upstream) from a transgene, and the MYC-3'MAR variants can be positioned 3' (downstream) from a transgene. Alternatively, MYC-5'MAR variants can be positioned 3' (downstream) from a transgene, and the MYC-3'MAR variants can be positioned 5' (upstream) from a transgene.

By incorporating MYC-MAR sequences into a vector design, a practitioner may regulate the nuclear organization of host cells by permitting more efficient interaction among trans-acting regulatory proteins present within the nuclear compartment of a host cell and cis-regulatory DNA elements, such as promoters and enhancers. Structural re-organization of the nuclear sub-compartments may be achieved by sub-regions of MYC-5'MAR and MYC-3'MAR sequences.

(a) Variants of Human MYC-MARs

In one embodiment, the present expression vectors comprise a human MYC-5'MAR sequence that includes SEQ ID NO:6, sequences that have at least 50% identity with respect to SEQ ID NO:6 within any given 1000 base pairs of alignment, and preferably sequences that have at least 70% identity with respect to SEQ ID NO:6 within any given 500 base pairs of alignment.

In another embodiment, the present expression vectors comprise a human MYC-3'MAR sequence that include SEQ ID NO:7, sequences that have at least 50% identity with respect to SEQ ID NO:7 within any given 1000 base pairs of alignment, and preferably sequences that have at least 70% identity with respect to SEQ ID NO:7 within any given 500 base pairs of alignment. In another embodiment, the present expression vectors comprise a sub-region of MYC-3'MAR that contain the sequence of SEQ ID NO:8, or that has at least 50% identity to SEQ ID NO:8. Various embodiments are directed to variant sequences of SEQ ID NO:8, which appears to be unique to human MYC-3'MAR, and have at least 50%, 55%, 60%, 65%, 70%, 75%, 80%, 85%, 90%, and 95% identities.

In another embodiment, the present expression vectors comprise both a human MYC-5'MAR and a human MYC-3'MAR. Such human MYC-5'MAR includes SEQ ID NO:6, sequences that have at least 50% identity with respect to SEQ ID NO:6 within any given 1000 base pairs of alignment, and preferably sequences that have at least 70% identity with respect to SEQ ID NO:6 within any given 500 base pairs of alignment. Such human MYC-3'MAR sequence includes SEQ ID NO:7, sequences that have at least 50% identity with respect to SEQ ID NO:7 within any given 1000 base pairs of alignment, and preferably sequences that have at least 70% identity with respect to SEQ ID NO:7 within any given 500 base pairs of alignment.

(b) Variants of Murine MYC-MARs

In another embodiment, the present expression vectors comprise a murine MYC-5'MAR sequence that includes SEQ ID NO: 11, sequences that have at least 50% identity with respect to SEQ ID NO: 11 within any given 1000 base pairs of alignment, and preferably sequences that have at least 70% identity with respect to SEQ ID NO:11 within any given 500 base pairs of alignment.

In another embodiment, the present expression vectors comprise a murine MYC-3'MAR sequence that includes SEQ ID NO:12 and variants of SEQ ID NO: 12. With respect to the human MYC-3'MAR, a comparable sequence is reasonably identifiable within the 3' region of murine c-myc locus. A sequence containing a sub-fragment of the murine MYC-3'MAR (SEQ ID NO:12) was identified within an approximately 10 kb, 3' region of c-myc. The murine MYC-3'MAR (SEQ ID NO:12) shares approximately 80% sequence identity with a sub-region of human MYC-3'MAR (SEQ ID NO:7). The present embodiments are directed to variant sequences of MYC-3'MAR (SEQ ID NO:12) that can attach to the nuclear matrix, and that have at least 50%, 55%, 60%, 65%, 70%, 75%, 80%, 85%, 90%, and 95% identities with respect to MYC-3'MAR (SEQ ID NO:12).

(c) Variants of Human/Murine MYC-MARs

Various embodiments are directed to expression vectors comprising any combination of the following: a human MYC-5'MAR, a human MYC-3'MAR, a murine MYC-5'MAR, and a murine MYC-3'MAR. Such embodiments include the combination of any of the following sequences: SEQ ID NO:6, sequences that have at least 50% identity with respect to SEQ ID NO:6 within any given 1000 base pairs of alignment, sequences that have at least 70% identity with respect to SEQ ID NO:6 within any given 500 base pairs of alignment; SEQ ID NO:7, sequences that have at least 50% identity with respect to SEQ ID NO:7 within any given 1000 base pairs of alignment, and preferably sequences that have at least 70% identity with respect to SEQ ID NO:7 within any given 500 base pairs of alignment; SEQ ID NO:11, sequences that have at least 50% identity with respect to SEQ ID NO: 11 within any given 1000 base pairs of alignment, and preferably sequences that have at least 70% identity with respect to SEQ ID NO: 11 within any given 500 base pairs of alignment; and SEQ ID NO:12 and sequences that can attach to the nuclear matrix, and that have at least 50%, 55%, 60%, 65%, 70%, 75%, 80%, 85%, 90%, and 95% identities with respect to MYC-3'MAR (SEQ ID NO:12).

(d) The Combined Effect of MINE and MYC-MARs on Transgene Expression

In one embodiment, an expression vectors comprise a MINE that is operably linked to a MYC-5'MAR in an arrangement which is functionally equivalent to the endogenous, intact 5'boundary region of c-myc. The MINE and the MYC-5'MAR are operably linked to a transcriptional unit within an expression vector so that the insulating (i.e., enhancer-blocking) and barrier activities of MINE, and the nuclear-matrix attachment activity of MYC-5'MAR can operate synergistically to enhance trangene expression level. An example of an optimal arrangement includes positioning a MYC-5'MAR upstream of a MINE, which is positioned upstream of a enhancer/promoter element, which is positioned upstream of a transgene. In these embodiments, a MINE can be positioned in any orientation.

In another embodiment, expression vectors comprise a MINE that is operably linked to a transcriptional unit of a transgene, which is operably linked to a MYC-3'MAR. In these embodiments, a MINE can be positioned in any orientation. In another embodiment, an expression vector comprises a MINE, a MYC-5'MAR, and a MYC-3'MAR, that are operably linked to a transcriptional unit of a transgene. An example of an optimal arrangement includes positioning a MYC-5'MAR upstream of a MINE, which is positioned upstream of the enhancer/promoter element, which is positioned upstream of a transgene, which is positioned upstream of a MYC-3'MAR.

C. Use of MINE with Heterologous MARs and the Use of MYC-MARs with Heterologous Insulators within Expression Vectors 1. Protective Effect of Insulators on Transgene Expression The incorporation of insulators into an expression vector including a transgene of interest can provide: (1) an effective insulating shield against negative influences from external enhancers, i.e., preventing background promoter-enhancer interactions; and (2) an effective barrier against the encroachment by host heterochromatin after random integration. Expression vectors comprising insulator elements with barrier activity, such as MINE, can inhibit heterochromatin progression at sites of integration, and therefore, substantially improve transcriptional efficiency by overcoming the problem of heterochromatin-induced silencing of transgenes.

It has been shown by the present inventors that the barrier activity of MINE is separable from the nuclear-matrix anchoring activity of MYC-5'MAR. The separability of insulators from endogenous nuclear-matrix-attachment regions appears to be a general phenomenon. In various embodiments, a MINE, sub-fragments of MINE, and MINE sequence variants may be operably linked with a heterologous MAR sequence, derived from a gene locus other than c-myc. Examples of heterologous MARs include: Human IFN-α MAR, Human interferon-beta 1, Apo-B MAR, Serpin MARs, Human β-globin MARS, and Human IgH MARs.

In various embodiments, variants of MYC-MARs, including variants of human MYC-5'MAR, human MYC-3'MAR, murine MYC-5'MAR, and murine MYC-3'MAR, can be operably linked with heterologous insulators, derived from a gene locus other than c-myc. Examples of heterologous insulators include: Chicken β-globin HS4, Human β-globin 3' HS1/5' HS5, Human Bead-1 (TCR α/β locus), Human Dad-1 (TCR α/β locus), *Drosophila* scs and scs' (Hsp70), *Drosophila* Gypsy (retrotransposon), *Drosophila* Fab-7 (Bithorax complex), *Drosophila* Mcp (bithorax complex), *Drosophila* eve-promoter (even-skipped gene), and *Xenopus* Repeat Organizer (RO) (Ribosomal RNA genes).

D. Gene Delivery Methods and Host Cells

1. Gene Delivery Vectors and Related Methods

The present expression vectors may be introduced into a host cell by receptor-mediated gene delivery, by microinjection, and by conventional methods of transfection such as liposome fusion, electroporation, and calcium-phosphate precipitation. To produce recombinant proteins using various mammalian cell lines, transfection and receptor-mediated gene delivery (i.e., virus infection) methods may be preferred. For protein production using insect cell-lines such as Hi-fives and Sf-9 cells, viral infection is a preferred method for gene delivery. Vectors designed to target insect tissues for making therapeutic and biopharmaceutical proteins are contemplated [Florian W. Wurm, Nature Biotechnology 21: 34-35 (2003)]. Primary or secondary cells can also be transfected by any transfection method listed.

Various gene delivery vectors that are practiced by persons skilled in the art can be used to introduce the present expression vectors. Examples of viral vectors that may be used to infect host cells include: improved adenoviral vectors that can target pulmonary tissues [Reynold et al., Nature Biotechnology 19: 838-842 (2001)]; gene-deleted adenovirus-transposon vectors that can stably maintain virus-encoded transgenes in vivo through integration into host chromosomes [Yant et al., Nature Biotechnology 20: 999-1005 (2002)]; recombinant adenoviruses that can target rat brain neurons [Bilang-Bleuel et al., Proc. Natl. Acad. Sci. U.S.A. 94: 8818-8823 (1997)]; Moloney-murine-leukemia-virus ("Mo-MuLV") based retroviral vectors that can target CD4+ and CD+8 Tcells and monocyte-macrophages [Auten et al., Human Gene Therapy 10: 1389-99 (2003)]; and poliovirus-replicon-based vectors that can target tissues of the central nervous tissue [Bledsoe et al., Nature Biotechnology 18: 964-969 (2000)]. Examples of other suitable viral vectors include: herpes virus, mumps virus, Sindbis virus, and vaccinia virus, such as the canary pox virus. The usage of viral vectors is well known by persons skilled in the art, and for gene therapy uses, viral infection is preferred generally [Robbins and Ghizzani, Mol. Med. Today 1:410-417, (1995)].

FIG. 4 illustrates a hypothetical example of a retroviral vector that includes a MINE, a MYC-5'MAR, and a MYC-3'MAR. In FIG. 4A, the retroviral vector is designed so that a transgene of interest (402) is inserted downstream of a given promoter (404), both of which are flanked upstream by a 5' LTR (406) enhancer and downstream by a 3' LTR (408) enhancer in a conventional arrangement. In one example (a), a MINE (409) is positioned upstream of the 3'LTR, and a MYC-5'MAR (410) is positioned downstream of a transgene (402) and upstream of a MINE (409). In another example (b), a MINE (409) is positioned upstream of a 3'LTR, and a MYC-3'MAR (412) is positioned downstream of a transgene (402) and upstream of a MINE (409). In another example (c), a MINE (409) is positioned upstream of a 3'LTR, and both MYC-5'MAR (410) and MYC-3'MAR (412) are positioned downstream of a transgene (402) and upstream of a MINE (409). FIG. 4B shows that in the absence of MINE and/or MYC-MARs, the integration of an expression vector within a heterochromatin site (420) may result in transcriptional silencing (422) due to the inactivation of a 3'LTR (424). In the absence of barrier elements, such as a MINE, an exogenous enhancer such as 5'LTR (426) may inadvertently activate neighboring transgene (428). In FIG. 4C, strategic placement of a first MINE (432) within a protected vector can preclude spreading of the heterochromatin (434), and placement of a second MINE (438) can provide a barrier against the leakiness of a 5'LTR (436) enhancer activity to a neighboring endogenous gene (440). The strategic placement of MYC-MARs (442/443) within a vector can facilitate the recruitment of host factors, such as acetyltransferases, which are involved in maintaining an open chromatin architecture of euchromatin.

2. Host Cells (a) Eukaryotic Cell-lines for Recombinant Protein Production

In various embodiments, suitable host cells for recombinant protein production include cell-lines that can be maintained and propagated in culture. Examples of transformed or immortalized cells include: a Bowes Melanoma cell (ATCC Accession No. CRL 9607); a Daudi cell (ATCC Accession No. CCL 213); a HeLa cell and a derivative of a HeLa cell (ATCC Accession Nos. CCL 2, CCL2.1, and CCL 2.2); a HL-60 cell (ATCC Accession No. CCL 240); a HT-1080 cell (ATCC Accession No. CCL 121); a Jurkat cell (ATCC Accession No. TIB 152); a KB carcinoma cell (ATCC Accession No. CCL 17); a K-562 leukemia cell (ATCC Accession No. CCL 243); a MCF-7 breast cancer cell (ATCC Accession No. BTH 22); a MOLT-4 cell (ATCC Accession No. 1582); a Namalwa cell (ATCC Accession No. CRL 1432); a Raji cell (ATCC Accession No. CCL 86); a RPMI 8226 cell (ATCC Accession No. CCL 155); a U-937 cell (ATCC Accession No. CRL 1593); WI-38VA13 sub line 2R4 cells (ATCC Accession No. CLL 75.1); a CCRF-CEM cell (ATCC Accession No. CCL 119); a 2780AD ovarian carcinoma cell (Van Der Blick et al., Cancer Res. 48: 5927-5932, 1988); and heterohybridoma cells produced by the fusion of human cells and cells of another species. In another embodiment, the immortalized cell line can be a non-human cell-line, such as a CHO cell-line or a COS cell-line.

(b) Primary and Secondary Cells for Ex Vivo Gene Therapy

In one embodiment, primary and secondary cells may be transfected or infected with expression constructs, that represent embodiments of the present invention ("present expression constructs"), to enable stable, long term transgene expression within the tissues of a diseased patient. Primary and secondary cells may be removed from a diseased animal or a cancerous animal host prior to ex vivo transfection or infection. Examples of suitable host cells for use in gene therapy include various primary and secondary cells derived from mammalian tissues. Primary and secondary cells that can be transfected or infected ex vivo include fibroblasts, keratinocytes, epithelial cells, endothelial cells, glial cells, neural cells, lymphocytes, bone marrow cells, muscle cells, and precursors of these somatic cell types. The use of MINE, MYC-MARs, and any combination of MINE and MYC-MARs with other insulators and other MARs within the expression vectors may substantially enable the stable, long term expression of transgenes. Preparation of mammalian tissues for ex vivo adaptation are known to persons skilled in the art.

In another related embodiment, the present expression vectors may be used to genetically engineer tissues under ex vivo culture systems. For example, healthy stem cells may be removed from a donor so that the cells can be induced to differentiate into a desired tissue type. Stem cells and other embryonic tissues can be induced by known differentiation factors in a controlled microenvironment established within a tissue-growing laboratory. Such cells can be further manipulated by introducing the present expression vectors comprising the transgene of interest. The use of MINE, MYC-MARs, and any combination of MINE and MYC-MARs with other insulators and other MARs within the expression vectors may substantially enable the stable, long term expression of transgenes.

(c) Delivery of Pharmaceutical Compositions for In Vivo Gene Therapy

In one embodiment, the present expression vectors can be supplemented with sequences derived from recombinant viral vectors to enable stable, long term transgene expression within specific tissues of a diseased patient. Specific examples of viral vectors are described above in Subsection III D (1). A pharmaceutical composition comprising the present expression vectors can be administered to a diseased mammal. The use of MINE, MYC-MARs, and any combination of MINE and MYC-MARs with other insulators and other MARs within the expression vectors may substantially enable the stable, long term expression of transgenes. These expression vectors may be used to produce proteins with substantial therapeutic value.

Because c-myc is widely expressed in mammalian systems, many diseases have been attributed to aberrant regulation of c-myc. Many types of cancers have been associated with the overexpression of a c-myc gene, including 80% of breast cancers, 70% of colon cancer, 90% of gynecological cancers, 50% of hepatocellular carcinomas, and hematological tumors. N-myc amplifications associated with neuroblastoma and chromosomal translocations affecting c-myc in Burkitt's lymphoma are noted examples. Furthermore, cancers that are associated with Epstein-Bar Virus (EBV) have been associated with c-myc overexpression [Cutrona et al, "Transfection of the c-myc oncogene into normal Epstein-Barr virus-harboring B cells results in new phenotypic and functional features resembling those of Burkitt lymphoma cells and normal centroblasts," J. of Experimental Medicine, Vol. 181, p. 699-711 (1995)]. Such diseases may be targeted by pharmaceutical agents or drugs that are able to interact with MYC-MAR sequences in vivo, either directly or indirectly.

E. Artificial Chromosomes Comprising MINE and MYC-MARs

Figure 3:
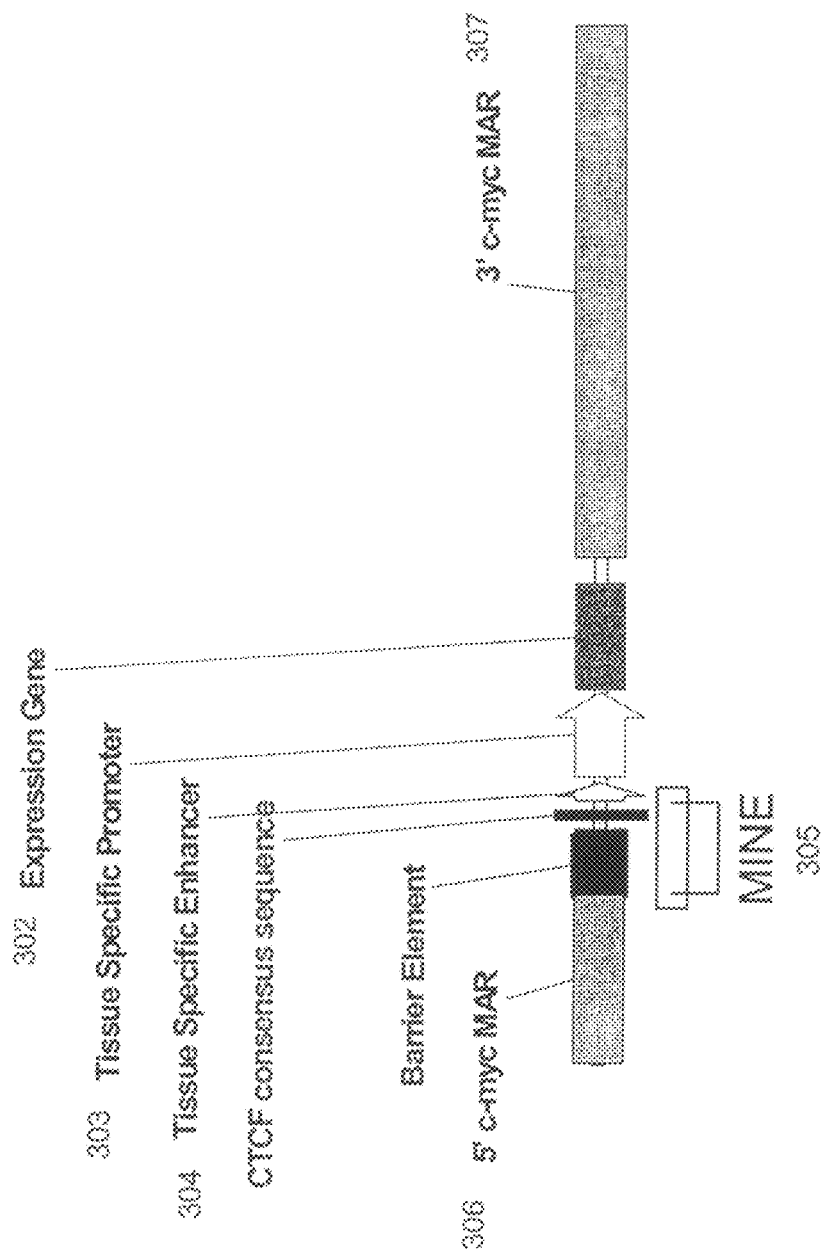
FIG. 3 illustrates a hypothetical example of an artificial chromosome that includes the MINE, MYC-5'MAR, and MYC-3'MAR.

As another embodiment, the present expression vectors may be used to genetically engineer artificial chromosomes for the production of recombinant protein. FIG. 3 illustrates a hypothetical example of an artificial chromosome that includes the MINE, MYC-5'MAR, and MYC-3'MAR. For example, a transgene (302) can be positioned and operably linked downstream from a tissue-specific promoter (303) and enhancer (304) elements. Such a transcriptional unit (302-304) can be operably linked by one or more MINE (305), which can be operably linked to an upstream MYC-5'MAR (306). The transcriptional unit (302-304) can be operably linked to a downstream MYC-3'MAR (307). Within artificial chromosomes that are mini-chromosomal structures, multiple copies of the present nucleic acid sequences can be arranged in an optimal configuration that may substantially enhance the rate of recombinant protein production. Methods for constructing artificial chromosomes are known by persons skilled in the art.

F. Transgenic Plants and Animals Comprising MINE and MYC-MARs

In another embodiment, the present expression vectors may be used to engineer non-human transgenic animals for the production of recombinant protein products. Various vectors systems that can target animal tissues of vertebrates, which are known and practiced by persons skilled in the art, are contemplated. Examples of suitable vectors and suitable cells were provided in Subsection III.D (1) and. (2). Methods for making transgenic animals are known by persons skilled in the art [Taube et al., Transgenic Res. 11(4): p397-410].

In another embodiment, the present expression vectors may be used to engineer transgenic plants for the production of recombinant protein. Examples of suitable host that may be transformed by standard transformation techniques include: *Nicotiana bethamiana*, *Arabidopsis thaliana*, tomato, banana, turnip, black-eyed bean, oilseed rape, Ethiopian mustard, potato, rice, wheat, and maize [Giddings et al., Nature Biotechnology 18: 1151-1155 (2000) is hereby incorporated by reference]. In addition, non-transgenic plants may be infected with recombinant viruses, such as the tobacco mosaic virus (TMV) and the cowpea mosaic virus (CPMV), that can be engineered to contain the present compositions to express transgenes during their replication cycles. The present compositions may be operably linked to plant virus or plant promoters such as the CaMV 35S promoter, glutelin Gt3 promoter, and the legume B4 promoter [Giddings et al., Nature Biotechnology 18: 1151-1155 (2000)]. Higher production levels of vaccines, antibodies, and biopharmaceuticals may be achievable using the present compositions within vectors that are known and practiced by persons skilled in the art.

EXAMPLES

The following examples are offered as illustrations of certain embodiments of the present invention. In Example 1, regions of the c-myc locus that associate with either acetylated or methylated histones were defined in order to identify the boundaries between euchromatin and heterochromatin. In Example 2, at least two CTCF-binding elements that are functionally occupied with CTCF in vivo were defined within the 5'boundary of c-myc. In Example 3, the enhancer-blocking activity and barrier activity of MINE were defined. In Example 4, enhancer-blocking activity and silencing activity within the subregions of MINE were functionally distinguished. In Example 5, the barrier activity within a subregion of MINE was defined. In Example 6, the 5' and 3' matrix attachment regions (MARs) at the c-myc locus were identified.

Example 1

Boundary Definitions of Euchromatic and Heterochromatic Domains at the c-myc Locus Transitions in the histone modification patterns mark the boundaries between euchromatic and heterochromatic domains at a gene locus [Litt et al., Embo J. 20: 2224-35 (2001)]. A high resolution map of histone acetylation and methylation patterns was generated within a 25 kb region of c-myc loci in both human and mouse (FIG. 5) by using a chromatin immunoprecipitation (ChIP) assay described below. CTLL2 cells, representing a murine T cell line, were exposed with interleukin 2 (IL-2) to induce c-myc transcription. HL60 cells of the human promyelocytic leukemia cell line were exposed with DMSO to induce differentiation, which correlates with c-myc expression downregulation. Chromatin immunoprecipitation assay (ChIP) was performed, involving the immunoprecipitation of formaldehyde-crosslinked chromatin from cell extracts using antibodies that specifically recognize modified forms of histone H3: (1) acetylated lysines 9 (K9) and 14 (K14), and (2) methylated lysine 9 (K9). Cross-linked chromatin was isolated from resting (FIGS. 5A and 5B, broken line) and IL2-induced (FIGS. 5A and 5B, solid line) mouse CTLL2 cells, and from proliferating human HL60 cells (FIGS. 5C and 5D).

The enrichment of c-myc specific histone modifications was measured by duplex PCR, by isolating the DNA from immunoprecipitated chromatin from the mouse (FIG. 5A) or human (FIG. 5B) c-myc locus, and subjecting them to PCR amplification using pairs of primers corresponding to their relative positions as indicated by vertical bars [FIGS. 5A and 5B, (a through w) or FIGS. 5C and 5D (A through Z)]. For normalization of acetylation levels, primers specific for mouse β-globin gene promoter or for human region G corresponding to sequences 10 kb upstream of human c-myc exon 1 were included in the PCR reactions as internal standards. Enrichment of lys 9 methylated histone H3 was measured relative to c-myc exon 1 (human) or c-myc exon 2 (mouse) sequences. The degree of enrichment was calculated relative to the ratio obtained in the input DNA fraction. Primer sequences specific for human and mouse c-myc are provided below.

RESULTS: Patterns of histone acetylation and methylation detected over a 25 kb region of human and mouse c-myc loci are highly conserved. FIGS. 5A and 5C show that hyperacetylation of H3 correlated with the 7.0 kb region (shaded area from −2.5 kb to +4.5 kb relative to exon 1) that constitutes the c-myc promoter and transcribed regions. In particular, the extensive acetylation of H3 associated with DNA representing the transcription initiation site of the P1, and P2 promoters, which extends to exon 2/intron 2 sequences. With increasing distance from the transcription initiation site, H3 acetylation decreases progressively, barely detectable within exon 3 and regions 2.3 kb upstream of exon 1. Primer sets that are specific for sequences further upstream of −2.3 kb and downstream of exon 3 failed to detect enrichment in acetylation relative to the internal standard primer sets.

The distribution of K9-methylated histones along the 25 kb region of the human and murine (FIGS. 5B and 5D) c-myc gene loci is inversely related to the distribution of acetylation (FIGS. 5A and 5C). Hyperacetylated regions are flanked by heterochromatin enriched in K9-methylated histone H3 as shown in FIGS. 5B and 5D. In mice, FIG. 5B indicates that the promoter region and the adjoining transcribed sequences of exon 2 are not methylated within the region spanning e through m. FIG. 5A demonstrates that hypoacetylated regions upstream of 2.3 kb (a through e) and downstream (m through w) of exon 3 is associated with K9-methylated histone H3. The level of enrichment relative to c-myc transcribed sequences ranges from 3 to 6-fold, which is a magnitude similar to that obtained for the β-globin or myoD loci. Both loci are transcriptionally silent in human HL60 cells and mouse CTLL2 cells.

Data indicate that the mammalian c-myc gene resides within a large hyperacetylated domain flanked by chromatin with heterochromatin characteristics. The patterns of methylation and acetylation in mouse and human are basically similar by the fact that in both systems, hyperacetylated domain extends approximately 2 kb upstream of the c-myc exon 1 sequences, and is flanked by transcriptionally inert chromatin containing K9-methylated, hypo-acetylated histone H3. The degree of hypermethylation is similar to that of the transcriptionally inactive murine β-globin gene in CTLL2 cells (see bars to the right of FIG. 5B) and to the human myoD and β-globin gene in HL60 cells (see bars to the right of FIG. 5D).

CELL CULTURE: The human HL60 and Jurkat cell lines were cultured in RPMI 1640 medium supplemented with 10% fetal calf serum, 2 mM L-glutamine, and antibiotics penicillin (50 U/ml) and streptomycin. HL60 cells were induced to differentiate with 1.5% DMSO for 2 h. The IL2-dependent murine CD8$^+$ T-cell line CTLL2 was maintained in RPMI 1640 supplemented with 1 mM sodium pyruvate, 10% fetal bovine serum, 2 mM L-glutamine media, antibiotics and 50 u/ml rIL2 (Chiron, Emeryville, Calif.). To inhibit proliferation and to generate a resting T-cell population, CTLL2 cells were placed into media lacking IL2 for 8 h. For mitogenic induction, 100 U/ml rIL2 was added.

CHROMATIN IMMUNOPRECIPITATION ASSAY: ChIP assays were performed according to Shang et al. [Cell 103: 843-52 (2000)]. Chromatin was cross-linked in the presence of 1% formaldehyde for 5 min. at room temperature. After the addition of glycine to a 0.125 M concentration, the cells were washed in ice-cold PBS containing protease inhibitors (Roche Molecular Biochemicals). Cells were pelleted, resuspended in SDS lysis buffer (1% SDS, 10 mM EDTA, 50 mM Tris-HCl pH 8.1, 1× protease inhibitor cocktail and 10 mM butyrate), and sonicated 6 times 20 seconds each at setting 6.5 in a Branson sonicator with microtip. The length of the DNA fragments ranged from 200 bp to 800 bp. After centrifugation to remove cell debris, the whole-cell extract was diluted 10-fold with ChIP dilution buffer (1% Triton X-100, 2 mM EDTA, 20 mM Tris-HCl pH 8.1, 150 mM NaCl, 1× protease inhibitor cocktail and 10 mM butyrate). Before immunoprecipitation, the chromatin solution was pre-cleared with protein A agarose slurry and normal rabbit serum to reduce non-specific background. Anti-acetylated histone H3, anti-methylated K9 or anti-CTCF antibody (Upstate Biotechnology) was added and incubated overnight at 4° C. with agitation. A no-antibody control was also performed for each ChIP assay. Immune complexes were collected by addition of 25 μl of protein A agarose slurry that had been preincubated with bovine serum albumin and salmon sperm DNA. After incubation at 4° C. for 2 h the beads were washed several times according to Orlando et al. [Methods 11: 205-14 (1997)]. The DNA contained within the immune complexes was recovered by the addition of proteinase K and SDS (0.1%) for 1 hour at 55° C. followed by incubation at 65° C. for at least 4 h to reverse the cross-links. The DNA was then purified by phenol/chloroform extraction and precipitated with ethanol precipitation.

DUPLEX PCR: DNA recovered from immunoprecipitations was analyzed by duplex PCR using c-myc specific primers and reference primers (β-globin, MyoD), the sequences of which are provided below. The reactions were performed with the Failsafe™ Taq polymerase in 1× buffer F (Epicenter), 10 pmol of each c-myc primer in the presence of a $^{32}$P-dCTP. After electrophoresis on a native 6% acrylamide gel, the signals were quantified with the Cyclone™ phospho-imager. The fold enrichment in each immunoprecipitation was determined by calculating the ratio of the signal obtained with c-myc primers to that of the reference primers.

C-MYC SPECIFIC PRIMERS: The primer sets for each sub-region of the c-myc loci from A to Z (human primer sequences) and a to w (mouse primer sequences) are provided below in Table 1, also represented in FIG. 5. Forward primers are designated with subscript "f" and reverse primers are designated with subscript "r":

TABLE 1

| | | | |
|---|---|---|---|
| Af | 5'GAGCCTGGCAAGTTCAAGAC3' (SEQ ID NO: 23) | Ar | 5'AGAATGGCCACAAAGTCCAC3' (SEQ ID NO: 68) |
| Bf | 5'CAGAGGTGAGGGAGGTCTTG3' (SEQ ID NO: 24) | Br | 5'CCTGGTGCAGAAGACACAGA3' (SEQ ID NO: 69) |
| Cf | 5'CAACAGGGCTGTGAGAAAGA3' (SEQ ID NO: 25) | Cr | 5'TACAGGCATGAACCAACCACA3' (SEQ ID NO: 70) |
| Df | 5'GGGCAAGATGGTGAAACACT3' (SEQ ID NO: 26) | Dr | 5'tCACTGCAGCCTTGAACTTG3' (SEQ ID NO: 71) |
| Ef | 5'AGCTCAGGATTCCAAGACCA3' (SEQ ID NO: 27) | Er | 5'AGCAGTCCTCCCACCTCAG3' (SEQ ID NO: 72) |
| Ff | 5'AACCTGTCATCCAAGCCAAC3' (SEQ ID NO: 28) | Fr | 5'GGGGTAAAGTGGGTTTAGGC3' (SEQ ID NO: 73) |
| Gf | 5'ATCGTCCAAGTGCAGACACA3' (SEQ ID NO: 29) | Gr | 5'GGGCTGGCACAGAAAATATC3' (SEQ ID NO: 74) |
| H.1f | 5'CTAAAAGCCAGGAGGGGAAG3' (SEQ ID NO: 30) | H.1r | 5'CACAGGAAAGCTCTTCAGCA3' (SEQ ID NO: 75) |
| Jf | 5'TTAACCTGGCTGAGGTCTGG3' (SEQ ID NO: 31) | Jr | 5'TGCCTGTGGGTTCAGAACTT3' (SEQ ID NO: 76) |
| Kf | 5'GCCATTACCGGTTCTCCATA3' (SEQ ID NO: 32) | Kr | 5'CAGGCGGTTCCTTAAAACAA3' (SEQ ID NO: 77) |
| Lf | 5'GTCCGGGGAGGAAAGAGTTA3' (SEQ ID NO: 33) | Lr | 5'CAAAGGTGCTAGACGGGAGA3' (SEQ ID NO: 78) |
| Mf | 5'TAGTAATTCCAGCGAGAGGC3' (SEQ ID NO: 34) | Mr | 5'AGCGCAGCTCTGCTCGCC3' (SEQ ID NO: 79) |
| Nf | 5'GAGGCTATTCTGCCCATTTG3' (SEQ ID NO: 35) | Nr | 5'GCATTCGACTCATCTCAGCA3' (SEQ ID NO: 80) |
| Of | 5'GCAGTTGCATCTCCGTATTG3' (SEQ ID NO: 36) | Or | 5'CCCGTCCAACACTCCTTTT3' (SEQ ID NO: 81) |
| Pf | 5'TTTATTCCCCCACCAAGACC3' (SEQ ID NO: 37) | Pr | 5'CGGGAGGCAGTCTTGAGTTA3' (SEQ ID NO: 82) |
| Rf | 5'AAGGCCCCCAAGGTAGTTA3' (SEQ ID NO: 38) | Rr | 5'ACGCACAAGAGTTCCGTAGC3' (SEQ ID NO: 83) |
| Tf | 5'CAGTAGGATGGGAGCAAGGA3' (SEQ ID NO: 39) | Tr | 5'AAAACACCCAGAAATGCTGG3' (SEQ ID NO: 84) |
| Uf | 5'GGATAAGGTCCTGGTGCTGA3' (SEQ ID NO: 40) | Ur | 5'CAGGATTACTGGGAGGCTGA3' (SEQ ID NO: 85) |
| Vf | 5'TTGGGCAATTGTGTTGCTAA3' (SEQ ID NO: 41) | Vr | 5'TCCTAGGCGTCACTCTCTGAA3' (SEQ ID NO: 86) |
| Wf | 5'TGCCCAGAGGAGTTTGTACC3' (SEQ ID NO: 42) | Wr | 5'CAGCCAAAAGCCAGTAGAGG3' (SEQ ID NO: 87) |
| Xf | 5'GCGGACAGAAACCACATC3' (SEQ ID NO: 43) | Xr | 5'GGAATGACAGCCTGGTTTGT3' (SEQ ID NO: 88) |
| Yf | 5'GGGAAAGGGGCAGTTGTAAA3' (SEQ ID NO: 44) | Yr | 5'GCACCACTGAGTCATTTCCA3' (SEQ ID NO: 89) |
| Zf | 5'CTCCTCCCCTGCATGTATGT3' (SEQ ID NO: 45) | Zr | 5'CACGTGAGAATTTCGCTTGA3' (SEQ ID NO: 90) |
| af | 5'CAACCCCCACCACCTATAAC3' (SEQ ID NO: 46) | ar | 5'TGGGAAAGCTTCTGGAAATG3' (SEQ ID NO: 91) |
| bf | 5'TCCTGCTTCTCTCCCGAGTA3' (SEQ ID NO: 47) | br | 5'TCCCCCAATGTTCTTGAATC3' (SEQ ID NO: 92) |
| cf | 5'CCTTCCCATAACAGCCCT3' (SEQ ID NO: 48) | cr | 5'CCCGATGGCAGAGAGTACAT3' (SEQ ID NO: 93) |
| df | 5'TGTTGGTGCTGTCCTGTGTT3' (SEQ ID NO: 49) | dr | 5'ATCTGAGCAACAGGCAAGGT3' (SEQ ID NO: 94) |

TABLE 1-continued

| | forward | | reverse |
|---|---|---|---|
| ef | 5'CAAGGAAGCATCTTCCCAGA3' (SEQ ID NO: 50) | er | 5'GTTGTGGCTCTCGGATTTGT3' (SEQ ID NO: 95) |
| ff | 5'CGAGGAGTCCGGAATAAGAA3' (SEQ ID NO: 51) | fr | 5'TCTTTTGCTCTGTGCATTGG3' (SEQ ID NO: 96) |
| gf | 5'CAATTCACTCCTCCCCCTTT3' (SEQ ID NO: 52) | gr | 5'AATCCTCTTTGCCCCTGTG3' (SEQ ID NO: 97) |
| hf | 5'ACATGGCGTATTGTGTGGAG3' (SEQ ID NO: 53) | hr | 5'CCGACCATTTTCTCTTGCTC3' (SEQ ID NO: 98) |
| if | 5'AGGGATCCTGAGTCGCAGT3' (SEQ ID NO: 54) | ir | 5'TCCAGAGCTGCCTTCTTAGG3' (SEQ ID NO: 99) |
| jf | 5'GCACATGGACTTGATGTTGG3' (SEQ ID NO: 55) | jr | 5'CTCACCGCAGTCTTCCTAGC3' (SEQ ID NO: 100) |
| kf | 5'CTAGTCCGACGAGCGTCACT3' (SEQ ID NO: 56) | kr | 5'CTGAACCACTCCCCTTTCAG3' (SEQ ID NO: 101) |
| lf | 5'AGAAGCTGGCCTCCTACCAG3' (SEQ ID NO: 57) | lr | 5'ACTGAGGGGTCAATGCACTC3' (SEQ ID NO: 102) |
| mf | 5'CAACGTCTTGGAACGTCAGA3' (SEQ ID NO: 58) | mr | 5'TCGTCTGCTTGAATGGACAG3' (SEQ ID NO: 103) |
| nf | 5'TTGCTCCCAGGTGATAGTCC3' (SEQ ID NO: 59) | nr | 5'AAGCTCTGCAACCCTCTGAA3' (SEQ ID NO: 104) |
| of | 5'CAGTCTTCACCCGACCATCT3' (SEQ ID NO: 60) | or | 5'TCCAGCTGAGTTGTTTGTGG3' (SEQ ID NO: 105) |
| pf | 5'CTGAAGCCATTCTCCACTCC3' (SEQ ID NO: 61) | pr | 5'TTCCATTCTTCAAGGGGTTG3' (SEQ ID NO: 106) |
| qf | 5'TGGACCGGTAGGTAGCTTTG3' (SEQ ID NO: 62) | qr | 5'AGAACAGCTTGGCCAGTGAC3' (SEQ ID NO: 107) |
| sf | 5'GCCCAGCTAAACCTCTTCCT3' (SEQ ID NO: 63) | sr | 5'CACAGGGTTCCAACTTTTGC3' (SEQ ID NO: 108) |
| tf | 5'GAGGCCTAGGGAATGGACTC3' (SEQ ID NO: 64) | tr | 5'CCCAGTTCTCTGGACCTTTG3' (SEQ ID NO: 109) |
| uf | 5'GCGCTGGGGATATGATTAAG3' (SEQ ID NO: 65) | ur | 5'CCAGGAAAGCAAGAGAAGGA3' (SEQ ID NO: 110) |
| vf | 5'CAATATCTTGAGGCGCTGCT3' (SEQ ID NO: 66) | vr | 5'GTCACCGGGTATTGGATCAC3' (SEQ ID NO: 111) |
| wf | 5'CTGAGGACATGCTGCAAAAC3' (SEQ ID NO: 67) | wr | 5'TGAGAGAGCAGCAGCTTCAA3' (SEQ ID NO: 112) |

Example 2

In vivo Identification of Two CTCF-Binding Elements within 5'boundary of c-myc

To determine the existence of functional binding sites for CTCF at the 5'boundary of the human and murine c-myc gene loci, in vivo associations between CTCF and regions of the 5'boundary were assayed by ChIP using a CTCF-specific antibody. Several potential CTCF-binding sites within the c-myc locus are listed in Table 2. The consensus sequence 5'-CCRNNAGRGG-3' (SEQ ID NO:18) was previously characterized by Bell et al. [Cell 98: 387-96 (1999)]. Sites A ("P2") (human SEQ ID NO: 20; mouse SEQ ID NO: 21) and B ("P1") (SEQ ID NO: 19) were identified by in vitro binding studies [Fillipova et al., Nat. Genet. 28: 335-43 (2001)]. Alignment of CTCF sites positioned near the 5'boundary (human SEQ ID NO: 15; mouse SEQ ID NO: 16) located upstream of exon 1, and at the P2 promoter (human SEQ ID NO: 20; mouse SEQ ID NO: 21) located downstream of the beginning of exon 1, suggested a high level of conservation between the human and mouse c-myc genes, which coincidentally occur near DNase I hypersensitivity sites [Siebenlist et al., Cell 37: 381-91 (1984)].

TABLE 2

| Site | Sequence | Location Relative to Exon I | Detected by ChIP |
|---|---|---|---|
| I) | 5'-TACTAAAAGCCAGGA-5.7 kb-GGGGAAGGGACAACACTAAGC (SEQ ID NO: 14) | −5.7 kb | − |
| II) human 5' boundary | 5'-TCTCTGCTGCCAGTA-2.0 kb+GAGGGCACACTTACTTTACT (SEQ ID NO: 15) | −2.0 kb | + |

TABLE 2-continued

| Site | Sequence | Location Relative to Exon I | Detected by ChIP |
|---|---|---|---|
| Murine 5'boundary | 5'-TCTCTGTGGCCAGTA GAGGGCACACTTACTTTA CT (SEQ ID NO: 16) | -1.9 kb | + |
| III) rev. orientation | 5'-TTTGGGAACCCGGGA GGGGCGCTTATGG (SEQ ID NO: 17) | +0.02 kb | - |
| Consensus | 5'-CCRNNAGRGC (SEQ ID NO: 18) | | |
| IV) human site B (P1) | 5'-GAGCTGTGCTGCTCG CGGCCGCCACCGCCGGGC CCC (SEQ ID NO: 19) | +0.03 kb | - |
| V) human site A (P2) | 5'-ATTCCAGCGAGAGGC AGAGGGAGCGAGCGGGCG GCC (SEQ ID NO: 20) | +0.23 kb | + |
| murine site A (P2) | 5'-ATTCCAGCGAGAGAC AGAGGGAGTGAGCGGACG GTT (SEQ ID NO: 21) | +0.18 kb | + |
| Mutant 5' boundary | 5'-TCTCTGCTGCCAATA TATGGAACACTTACTTTA CT (SEQ ID NO: 22) | | - |

In FIG. 6A, CTCF/formaldehyde-crosslinked chromatin complexes were isolated from resting and mitogen-induced mouse CTLL2 cells using the ChIP assay, and were subjected to Duplex PCR analysis. In FIG. 6B, CTCF-binding activities from both proliferating and differentiating human HL60 cells were determined by ChIP and Duplex analysis. Differentiation was induced by DMSO treatment, which down regulates transcription of the c-myc gene. Reference primers that hybridized to boundary elements at the β-globin and myoD genes containing binding sites for CTCF were used. Signals obtained with the murine c-myc primer sets (c to w) were normalized to the signal obtained using the murine β-globin primer set. The degree of enrichment is calculated relative to the ratio obtained in the input DNA fraction. Results using human c-myc primer sets were normalized to signals obtained using the human β-globin or myoD primer sets (FIG. 6B, "ref"). Methods for ChIP and duplex PCR, and primer sequences are provided in Example 1.

RESULTS: Of the potential CTCF-binding sites tested, only two highly conserved CTCF sites within human and mouse c-myc gene exhibited CTCF-binding activity. FIG. 6A shows that the CTCF bound only to sites within regions corresponding to the 5'boundary (region e) (SEQ ID NO:16) and the P2 promoter region (region i) (SEQ ID NO:21), in both resting and IL-2 stimulated murine CTLL2 cells. Furthermore, the binding of CTCF to the 5'boundary and the promoter-proximal region was not influenced by the IL2-mediated mitogenic induction of CTLL2 cells that were shown to up-regulate the murine c-myc at least ten-fold [Moon and Nelson., J. Immunol. 167: 2714-23 (2001)]. Similarly FIG. 6B shows that CTCF bound to homologous regions of human c-myc gene, at the 5'CTCF site (SEQ ID NO:15) (2 kb upstream of exon 1 and the DNase hypersensitive region I) corresponding to region K, and the P2 promoter (site A) (SEQ ID NO:20), corresponding to region N. The binding of the CTCF was constitutive, and not affected by the DMSO-induced inhibition of transcriptional elongation. No CTCF-binding to the 3'boundary region of c-myc gene, corresponding to hyperacetylated c-myc, was detected using the primer sets that annealed to regions defined by grey bars at the bottom of FIGS. 6A and 6B. The fact that CTCF bound constitutively to the murine and human c-myc loci is not compatible with its purported role as a transcriptional repressor at the c-myc gene.

Example 3

Functional Analysis of 1.6 kb c-Myc INsulator Element (MINE)

To determine the functional activity of the 1.6 kb MINE (SEQ ID NO:2) constituting the 5'boundary sequences of the human c-myc gene, it was placed at variable positions relative to enhancer and promoter elements within expression cassettes. FIG. 7 shows the positional effect of MINE in repressing or stimulating the transcription of a selectable marker reporter gene (neomycin), which was measured after its stable integration into genomic sites [Kellum and Schedl, Mol. Cell. Biol. 12: 2424-31 (1992)]. 5'boundary elements were placed either between the enhancer and promoter, or upstream of the enhancer. The number of colonies growing under G418 selection was determined after a period of six weeks, by soft agar colony forming assay (method provided below), with the colony number being indicative of the number of cells that can express the neomycin selectable marker gene stably integrated into genomic sites. Jurkat cells were transfected (method provided below) with these expression plasmids (method of plasmid construction provided below). The activity of the parent construct E-P-neo-scs' (Construct 1) was set to 100% as a reference. Results are shown with standard errors, and (n) represents the number of individual experiments.

The following constructs were tested. All constructs contained the element scs' to inhibit transcriptional interference originating from the integration site at the 3'end. Construct 1 representing E-P-neo-scs' consists of: the TCRδ-enhancer, the Vδ-promoter, the neomycin resistance gene, and the Drosophila hsp70 scs' boundary element, respectively. Construct 2 represents the P-neo-scs' lacking the Eδ enhancer. Constructs 4, 7, and 8 have the 1.6 kb MINE fragment (SEQ ID NO:2) or the 1.2 kb chicken β-globin insulator cHS4 (SEQ ID NO: 13) positioned upstream of the enhancer. Constructs 3, 5, and 6 have the 1.6 kb MINE fragment or the chicken β-globin insulator cHS4 positioned between the enhancer and promoter. The MINE fragment consists of the 1.0 kb BE-fragment and the 640 bp CTCF-fragment (method of construction described below).

RESULTS: At least two functional activities, the enhancer-blocking activity and the barrier activity, are conferred by MINE. FIG. 7 provides the relative number of G418 resistant colonies observed with respect to the expression cassettes tested. Absence of the Eδ enhancer (comparing Construct 2 and 1) resulted in a seven-fold reduction in the number of G418 resistant colonies (15% vs. 100%) due to reduced neomycin expression. As positive control, the 1.2 kb chicken β-globin HS4 insulator element was placed either upstream of the Eδ enhancer, or downstream of the Eδ enhancer (between Eδ and Vδ). Consistent with previous reports, the insertion of one copy of the chicken β-globin HS4 insulator between the Eδ enhancer and Vδ promoter reduced the number of G418 resistant colonies by approximately two-fold (comparing Constructs 3 and 1). In contrast, the insertion of the cHS4 element upstream of the Eδ enhancer had a nominal effect (comparing Constructs 4 and 1).

When the 1.6 kb MINE fragment derived from the c-myc 5'boundary (−1.7 kb to −3.3 kb relative to exon 1) was tested under parallel conditions, its ability to modulate the transcription of the reporter gene was analogous to the activity of the HS4 insulator element. When placed between Eδ and V δ (comparing Constructs 5 and 1), MINE inhibited the enhancer activity by two-fold. When positioned upstream from Eδ (Constructs 7 and 1), no effect was observed.

The orientation specificity of MINE was tested by inserting it between the enhancer and promoter elements in the reverse orientation, into the E-P-neo-scs' construct (Construct 6). Unexpectedly, MINE blocked enhancer-promoter interaction more efficiently in the 3' to 5' orientation (comparing Constructs 6 and 5) than it does in the alternative, 5' to 3' orientation, resulting in seven-fold reduction of G418 resistant colonies, equivalent to the number of colonies obtained after the deletion of the enhancer (comparing Constructs 6 and 2). In contrast, MINE increased the number of G418 resistant colonies by three-fold when positioned in the reversed orientation upstream of the enhancer, suggesting that it provides protection against position-effect variegation (comparing Constructs 8 and 7). Thus, these set of experiments show that MINE provides at least two functional activities such as the enhancer-blocking activity and the barrier activity, both of which are integral to the proper functioning of the 5'boundary of c-myc.

DNA CONSTRUCTS: E-P-neo-scs' was supplied by M. Krangel [Zhong and Krangel, Proc. Natl. Acad. Sci. USA 94: 5219-24 (1997)]. The "E", "P", "neo", and "scs" elements represent the TCRδ-enhancer, the Vδ-promoter, the neomycin resistance gene, and the *Drosophila* hsp70 scs' boundary element, respectively. The P-neo-scs' construct lacking the Eδ enhancer was generated by Xba1/Cla1digestion, treatment with T4 polymerase, and re-ligation. All boundary and control fragments were introduced into the NotI and/or XbaI sites upstream of Eδ, or the ClaI and/or SalI sites between Eδ and the Vδ promoter. The derivative construct E-MINE-P-neo-scs' was generated by triple ligation of PCR-generated 1.0 kb ClaI/HindIII BE-fragment (as provided below) and the 640 bp HindIII/SalI CTCF into ClaI-SalI sites between Eδ and the Vδ1 promoter. The 1.0 kb BE fragment from the c-myc locus was generated by PCR amplification of cosmid DNA using forward primer (5'-3'; CTATGAGATCGATGTGGACC) (SEQ ID NO:113) and reverse primer (5'-3'; GCTAATGAAAGTCGAACTATGG) (SEQ ID NO:114). The 640 bp CTCF was generated by PCR amplification of cosmid DNA using forward primer (5'-GAGTTTCATCGATGTGGGGG-3') (SEQ ID NO: 1.15) and reverse primer (5'-GGGGTGCGTCGACAGCATGT-3') (SEQ ID NO:116). All constructs were verified by sequencing.

THE SOFT AGAR COLONY-FORMING ASSAY: Jurkat cells ($10^7$ cells) were electroporated with 1.5 µmol (~5.0-10.0 µg) of linearized plasmid using a BTX-Electroporator (Hercules, Calif.) at 250 V, 1700° F., RF 72 (time constant ~40 msec). After the electroporation, cells were placed on ice for 20-30 min. The cell suspension was then transferred into 10 ml of RPMI 1640/10% fetal bovine serum and cultured at 37° C. After 48 h, $5 \times 10^5$ cells were resuspended in a 7 ml RPMI plating medium (11% FBS, 31% Jurkat-conditioned medium, 50 µl Penicillin/Streptomycin (78 µg/ml), 100 µl L-glutamine (78 U/ml) and 750 µg/ml active G418 (Life Technologies, Gaithersburg, Md.) in RPMI. After addition of 3 ml of soft agar plating medium [1:1 volumes of 0.2% agar (Difco) and 2×RPMI 1640 medium], cells were plated and incubated for three to four weeks. Transfections of Jurkat cells with each construct were performed in triplicate.

Example 4

Identification of Enhancer-blocking Activity and Silencing Activity within MINE

To functionally define the components of MINE within the 1.6 kb fragment, subfragments of MINE were individually tested using the colony assay (Example 3). In FIG. 8, distinct fragments of MINE (40 bp, 120 bp, and 640 bp) embodying the CTCF core consensus sequence were inserted either between the enhancer and the promoter, or upstream of the enhancer within the E-P-neo-scs' construct (Example 3). Fragments containing point mutations within the CTCF site (Constructs 5 and 6) were also tested. Jurkat cells were transfected with expression constructs by standard procedure, also provided in Example 3.

RESULTS: The enhancer-blocking activity of MINE (demonstrated by Example 3) is attributed to a 40 bp fragment containing the constitutive 5'CTCF-binding site (SEQ ID NO: 15) derived from sequences 2 kb upstream of the c-myc gene. FIG. 8A shows that when this 40 bp CTCF minimal element (Construct 4) is placed between the enhancer and promoter elements, it reduces the number of G418 resistant colonies two-fold, similar to the level obtained with the complete 1.6 kb MINE fragment (Construct 1) (SEQ ID NO:2). Mutation of four base pairs within the CTCF consensus sequence (SEQ ID NO:22) (provided in Table 2) removes this enhancer-blocking activity (comparing Constructs 4 and 5). Consistent with its function as an enhancer-blocking element rather than a silencing element, the 5'CTCF-binding site (SEQ ID NO: 15) of MINE does not affect neomycin gene expression when positioned upstream of the enhancer (Construct 4; 90%).

Sequences within the 1.6 kb MINE flanking the 40 bp CTCF element confer barrier and silencing activities. The fact that the 120 bp (FIG. 8, Construct 3) and 640 bp (FIG. 8, Construct 2) fragments, containing the 5'CTCF-binding site (SEQ ID NO: 15) and additional sequences, can suppress transcriptional activation more effectively than the minimal 40 bp fragment suggests the existence of silencing elements within the flanking regions of the 5'CTCF-binding site (SEQ ID NO:15). However, the negative effect of these sequences on transcription was masked in the context of the whole 1.6 kb MINE. Both the 120 bp (Construct 3; 21%) and the 640 bp (Construct 2; 32%) fragments efficiently inhibited the enhancer-promoter interaction when positioned between the enhancer and the promoter. These elements still retained their inhibitory activity when inserted upstream of the enhancer [Construct 3 (36%) and Construct 2 (45%), respectively]. In addition, the mutation of the 640 bp fragment at nucleotides that were found to eliminate CTCF function in the context of the 40 bp fragment, only partially abrogated its inhibitory function on the reporter construct (two-fold, comparing Constructs 2 and 6). In summary, the silencing and enhancer-blocking activities within MINE conferred by the 640 bp region at the human and mouse c-myc boundary contribute to the establishment of an efficient boundary. The boundary sequences further upstream show a high level of sequence conservation despite the absence of histone hyperacetylation or lys 9-methylation (FIG. 5). Thus, two sub-regions "S1" (spanning nucleotides 1256-1611 of SEQ ID NO: 1) and "S2" (spanning 1644-1885 of SEQ ID NO:1) within the flanking regions of the 5'-CTCF binding site (human SEQ ID NO: 15;

mouse SEQ ID NO: 16) have been characterized. S1 and S2 confer the silencing properties of MINE.

To confirm the loss of CTCF-binding in the mutated 640 bp fragment, chromatin derived from Jurkat cells that were transfected with constructs containing the 640 bp fragment or the 640 bp ΔCTCF fragment were immunoprecipitated using anti-CTCF antibody. Primers specific for the DM1 locus [Filippova et al., Nat. Genet. 28: 335-43 (2001)] were used as a positive control. Primers specific for 5'CTCF-binding site within the stably integrated transgene do not detect sequences of the endogenous c-myc gene. FIG. 8B shows that the reduced reporter activation observed from the placement of the mutated 640 bp fragment between the enhancer and promoter (FIG. 8A, Construct 6) is not mediated by a cryptic CTCF site that may exist in the flanking region. The enrichment of DM1 sequences relative to the j-globin demonstrates that the DNA that was cross-linked to the CTCF was efficiently recovered in both samples. The PCR amplification with primers specific for the 640 bp fragment contained in the transgene eliminates the possibility that CTCF can bind to the 640 bp fragment having mutations at the CTCF consensus sequence.

Example 5

Identification of Barrier Activity Mediated by BE within MINE

To determine the function of BE (SEQ ID NO:3) located upstream from the CTCF fragment (640 bp) positioned at the 5' boundary of the c-myc locus, the 1 kb BE fragment (FIG. 8A, Construct 7) containing the 5'CTCF-binding site (SEQ ID NO: 15) was inserted into the parent reporter construct E-P-neo-scs' (described in Example 3). The BE fragment, in contrast to the CTCF-containing elements, did not affect the number of G418 resistant colonies when positioned between the enhancer and promoter (FIG. 8A, Construct 7; 98±8%). However, when BE was positioned upstream of the enhancer, a greater than two-fold increase in the number of colonies was observed (FIG. 8A, Construct 7; 220±57%). In the absence of the enhancer, the BE was not able to enhance promoter activity. The increase in the number of G418 resistant colonies suggests that BE increases the likelihood of transgene expression in various genomic sites.

In summary, the data in FIGS. 7 and 8 demonstrate that the 1.6 kb MINE (SEQ ID NO:2) and the larger 1.9 kb MINE (SEQ ID NO:1) contain at least three distinguishable activities: silencing, enhancer-blocking, and barrier activities, all of which contribute to the 5' boundary function. FIG. 8C provides a schematic of the distinct functional elements within MINE: (1) the "CTCF" representing the 5'CTCF-binding element (shaded in black) (SEQ ID NO:15), (2) the "BE" representing the barrier element (shaded in gray) (SEQ ID NO:3), and (3) the "S$_1$" (SEQ ID NO:4) and "S$_2$" (SEQ ID NO:5), representing the silencing elements (shaded in white).

Example 6

Matrix Attachment by 5' and 3' MYC-MARs

To identify regions of the c-myc locus that associate in vivo with the nuclear matrix, sub-regions of DNA spanning a stretch of approximately 200 kb across c-myc were assayed by duplex PCR as described below. Jurkat cell nuclei were subjected to high-salt extraction procedures to remove non-scaffolding proteins (i.e., proteins not associated with the nuclear matrix), and were subjected to digestions with specific restriction enzymes. The DNA contained in the supernatant fraction representing fragments that did not associate with the matrix were separated from the non-soluble DNA (matrix-bound) in the pellet (P) by centrifugation, and their distribution was quantitatively determined by duplex PCR as described below. As positive control, a primer set specific for a known matrix attached region previously characterized at the apo B gene was used. Specific primer sets (provided below) were used to perform this analysis on a total of 68 genomic DNA fragments generated by the digestion with restriction enzymes HindIII/XbaI/EcoR1/ClaI (FIG. 2B).

RESULTS: FIG. 9 shows that two matrix attachment regions (MARs) that strongly attach to the nuclear matrix were identified at the c-myc locus: (1) the human 5'MAR (SEQ ID NO:6) corresponding to a region 76 kb upstream of the 5' end of c-myc gene, and (2) the human 3'MAR (SEQ ID NO: 7) corresponding to a region 32 kb downstream of the 3' end of c-myc. The human 3'MAR (SEQ ID NO: 7) was identified within a 10.7 kb fragment, flanked by HindIII and EcoR1 sites. The 5' and 3' MARs of human c-myc separate the c-myc gene from neighboring gene loci. The pvt1 gene is located 60 kb downstream of the c-myc gene, and a predicted and conserved gene locus (NCBI, accession number XM_299806) with unknown function resides 85 kb upstream of c-myc gene. Thus, the MARs define a >160 kb domain in which the transition of euchromatic and heterochromatic regions is maintained by insulator elements.

FIG. 9 demonstrates that the apo B MAR associate with the nuclear matrix in vivo by the fact that its MAR-specific sequences were enriched predominantly in the pellet fraction (83%±7) and less in the supernatant (7%±3) under every test condition. Similarly, five regions at c-myc predominantly associated with the nuclear matrix with a strength similar to the apoB MAR: (1) a 76 kb upstream region [FIG. 9, (P) 60%], and (2) a cluster of four fragments within a 10 kb downstream region [FIG. 9, at +42 kb (P) 90%, +39 kb (P) 47%, +45 kb (P) 93%, and +48 kb (P) 87%]. In contrast, the MINE sequences were identified in the supernatant fraction (primer set J, (P) 33%, (S) 67%) suggesting that its insulator function is not mediated through an attachment to the nuclear matrix. Similar to the MINE, the majority of the tested restriction fragments were enriched in the supernatant.

IN VIVO MAR AND DUPLEX PCR ASSAYS: Nuclei from Jurkat and HL60 cells was isolated according to Izaurralde et al., J. Mol. Biol. 200: 111-25 (1988) with some modification, and were kept at −20° C. in storage buffer (5 mM Tris.Cl pH 7.5, 20 mM KCl, 125 µM Spermidine, 50 µM Spermine, 500 µM EDTA, 1% v/v Thioglycol, 50% v/v glycerol) at a density of $10^8$ nuclei/ml. Matrices were stably stored in 50% glycerol at −20° C. for at least six months. To isolate matrix-bound (P, pellet) or soluble DNA (S, supernatant), nuclei from Jurkat T cells were subjected to a lithium 3,5-diiodosalicylate (LIS) extraction protocol. Nuclei of 107 matrices (1 $OD_{260}$ unit) were used per assay. Non-scaffold proteins were extracted by the addition of 1.0 ml 10 mM LIS (Sigma D-3635) extraction buffer, the salt-extracted nuclei were collected and subjected to restriction enzyme digestion with EcoRI, HindIII, Xba I and Cla I (~500-1000 U/sample) and/or with the addition of Eco1CR1 (Promega). After proteinase K treatment, DNA samples were then subjected to phenol/chloroform extraction and ethanol precipitation.

To quantify the relative distribution of specific DNA sequences in the P and S fractions, duplex PCR assay was performed. Two nanograms of each P and S fractions were used as templates for amplification with primer pairs corresponding to each restriction fragment (generated by Hind III, Xba I, Cla I, Eco RI and Eco1 CR1) across ~200 kb of the c-myc locus. The PCR reactions contained a primer set specific for the MAR at the apo B gene as a positive control (forward primer: 5'-GGGTGAATGAATGCCCTATG-3' (SEQ ID NO:117); reverse primer: 5'-TACTCCATGCGAG-GTCCACT-3') (SEQ ID NO:118). Results were expressed as a percentage of the signal from the matrix bound portion (T) or the supernatant portion (S), divided by the signal from the supernatant and pellet together, $I_P/I_T(100)$ and $I_S/I_T(100)$.

PRIMERS FOR APO B: Forward primer was 5'-GGGT-GAATGATGCCCTATG-3' (SEQ ID NO:119) and reverse primer was 5'-TACTCCATGCGAGGTCCACT-3' (SEQ ID NO: 120). PRIMERS USED TO DEFINE MYC-5'MAR: Primers sets are provided in Table 3.

TABLE 3

| Primer Set | Forward Primer 5' to 3' | Reverse Primer 5' to 3' |
|---|---|---|
| myc -78095/R-77923 | AGGTAGCAGGATCTCCTGAG SEQ ID NO: 121 | GTGTAGCGGCATCTCACTGT SEQ ID NO: 146 |
| myc -76248/R-76064 | AAAACCAACCCAATGTCTGG SEQ ID NO: 122 | CTCTGCTGGGTCTCATGTCC SEQ ID NO: 147 |
| myc -73082lR-72911 | CTGTGCCCTTTTCCTTCAAA SEQ ID NO: 123 | CCACTGGTCTGTCTGGGATT SEQ ID NO: 148 |
| myc -72448/R-72276 | TCCAAAACGTCCTGACACAC SEQ ID NO: 124 | GTTGAGGCATGAGTCCTGGT SEQ ID NO: 149 |
| myc -70480/R-70309 | CCCACAACACTGAAAGCAGA SEQ ID NO: 125 | GGATGTCCCCTAGCAAGGAT SEQ ID NO: 150 |
| myc -69648lR-69466 | AACACACCAGCCTGATAGGG SEQ ID NO: 126 | AGCCAGCCTTTCTGTTTTGA SEQ ID NO: 151 |
| myc -68013/R-67863 | GAGGCAAATTAACGCTGGTG SEQ ID NO: 127 | GGGCTCATAGCTGAATCTGG SEQ ID NO: 152 |
| myc -66982lR-66830 | ATATCCCAGCACTTGCCATC SEQ ID NO: 128 | AGAATCCACAAGGCAACCTG SEQ ID NO: 153 |
| myc -66023/R-65843 | GCCCAATATGCTGTTCCAAT SEQ ID NO: 129 | TGCATTCACAAGCATCACAA SEQ ID NO: 154 |
| myc -64605/R-64419 | AACCTTGGCAGGGAGGTAGT SEQ ID NO: 130 | GATGGCTAGAAGGCTGTTGC SEQ ID NO: 155 |
| myc -58774/R-58611 | AAGCTGCAGTGAGCCGTAAT SEQ ID NO: 131 | CCCTCCTGGTGTTCACACTT SEQ ID NO: 156 |
| myc -57513/R-57321 | ATCAAGTCCAGGGCAAACAG SEQ ID NO: 132 | GCGATTGTAAGCAACTGCAA SEQ ID NO: 157 |
| myc -53615/R-53423 | GTGGCATGGACATCATCAAG SEQ ID NO: 133 | TTGAATCCTGGTTGGTTTGC SEQ ID NO: 158 |
| myc -49449lR-49265 | TTACAGAAGGGACCGGTTTG SEQ ID NO: 134 | GGCACAGAGCCTCTTGTAGG SEQ ID NO: 159 |
| myc -42367lR-42209 | GACAGAAGGTTCTGGGGATG SEQ ID NO: 135 | ATGTTCTGGAAGTGGCAGGT SEQ ID NO: 160 |
| myc -37536/R-37371 | ATGGAAGGCAGTGAGAAGGA SEQ ID NO: 136 | TGCACATTGCACTTCTCTCC SEQ ID NO: 161 |
| myc -36463/R-36283 | GGGAAAGCAGTTACCCCTTC SEQ ID NO: 137 | GAGACCCCATCTCGCTAAAA SEQ ID NO: 162 |
| myc -35164/R-34994 | AGTGGAGCGAACACAGACCT SEQ ID NO: 138 | TAATGACCCCACCTCCTCTG SEQ ID NO: 163 |
| myc -31919/R-31754 | AAGGGGAGGAGAAAGAGCTG SEQ ID NO: 139 | GCAATTGGAGGACAAATGCT SEQ ID NO: 164 |
| myc -30727/R-30573 | AGAGCGAGACCCTGTCTGTG SEQ ID NO: 140 | GGTTTTGCCTTATGGATGCT SEQ ID NO: 165 |
| myc -28827/R-28640 | GGGTCTCACTCCATTGCCTA SEQ ID NO: 141 | TGGAGGCGGAGTAAGACTGT SEQ ID NO: 166 |
| myc -26574/R-26417 | CGTGGGCTCACTGGTTACTT SEQ ID NO: 142 | TTTTTGCTTGCACTTTGTGG SEQ ID NO: 167 |

TABLE 3-continued

| Primer Set | Forward Primer 5' to 3' | Reverse Primer 5' to 3' |
|---|---|---|
| myc -24443/R-24275 | AGCAATTGCAGGATGCTTTC SEQ ID NO: 143 | AAATGTGGAGGTGGGAGGAT SEQ ID NO: 168 |
| myc-22224/R-22070 | ATAACCCACCCCAGCATGTA SEQ ID NO: 144 | TGCCCTTTTCATCACATCAG SEQ ID NO: 169 |
| myc -20035/R-19870 | AACCGGGAGAAGTGTGAAGA SEQ ID NO: 145 | TGGACAGAAAAACCCTTTGG SEQ ID NO: 170 |

PRIMERS USED TO DEFINE MYC-3'MAR: Primers sets are provided in Table 4.

TABLE 4

| Primer Set | Forward Primer 5' to 3' | Reverse Primer 5' to 3' |
|---|---|---|
| myc 37764/R37959 | AGGGGATGAAAGGCCACTTG SEQ ID NO: 171 | AGGGAATCCTCCCTCATTTT SEQ ID NO: 189 |
| myc 38345/R38530 | GCACCCAGCCTGTTTCTTTA SEQ ID NO: 172 | TCCCTCCCTGCTTTCCTTAT SEQ ID NO: 190 |
| myc 39352/R39534 | CTATTCTGTGCCTGGCGAAC SEQ ID NO: 173 | CAAATGGAGCTGTGGGTGAT SEQ ID NO: 191 |
| myc 39410/R39563 | GTTGTGATCACCCACAGCTC SEQ ID NO: 174 | CAAATGGAGCTGTGGGTCAT SEQ ID NO: 192 |
| +39 KB | GTGATCACCCACAGCTCCAT SEQ ID NO: 175 | TGTGCGAATTTCACAAAAGG SEQ ID NO: 193 |
| myc 40573/R40726 | TGTGGGTGAAAGTGTTCCTG SEQ ID NO: 176 | GGAAGAGAGGGAGCAAATCC SEQ ID NO: 194 |
| myc 42002/R42153 | GCCAGGATTGTCTCGATTTC SEQ ID NO: 177 | AGCTGGCACCAACCTACCTA SEQ ID NO: 195 |
| myc 43219/R43405 | CTTCTGAGCCACTCCGTCTC SEQ ID NO: 178 | TAGTGGTGAGGCTGGGAAAC SEQ ID NO: 196 |
| myc 44535/R44730 | GGCAGGAATGACTCTTGGAG SEQ ID NO: 179 | ATGCATGTCCCAAAACAAG SEQ ID NO: 197 |
| myc 45842/R46025 | GTGGTGCAATCACAGCTCAC SEQ ID NO: 180 | CACTTGAGCACAGGAGTTGG SEQ ID NO: 198 |
| myc 45871/R46053 | CACCTCCTGGGCTCAAATAA SEQ ID NO: 181 | GCACTTTGTGAGGCTGAAGA SEQ ID NO: 199 |
| myc 46635/R46806 | GCACACATGGAACAAGGCTA SEQ ID NO: 182 | GATTCCCCAAGGCAGTCATT SEQ ID NO: 200 |
| myc 48125/R48296 | GAATGCAGTCTTGTGCCTCA SEQ ID NO: 183 | AAGCCCTGAGATGGGAGTTT SEQ ID NO: 201 |
| myc 49237/R49395 | AGGATGGAGAAAATGGAGCA SEQ ID NO: 184 | GCCTCTAGCCTAAGCAAAACA SEQ ID NO: 202 |
| myc 50675/R50831 | CTGGCAAAAGGAATGTGGAT SEQ ID NO: 185 | ATCTTCAACGTGTGGCTTCC SEQ ID NO: 203 |
| myc 52529/R52680 | GCTCCCCAATAGCTTTCCTT SEQ ID NO: 186 | GCTCCCCAATAGCTTTCCTT SEQ ID NO: 204 |
| myc 54992/R55132 | GGAAGCGCTGATTCATTAGG SEQ ID NO: 187 | GGAAGCGCTGATTCATTAGG SEQ ID NO: 205 |
| myc 56426/R56576 | TTTTTATGGCTGGCTCCTTC SEQ ID NO: 188 | AGGCAGAGGTTGGAGAATCA SEQ ID NO: 206 |

It will be appreciated that, although specific embodiments of the invention have been described herein for purposes of illustration, various modifications may be made without departing from the spirit and scope of the invention. Accordingly, the invention is not limited except as by the appended claims.

We claim:

1. A method for providing stable, long-term expression of a transgene in chromatin, comprising:
   transfecting a vector into a host cell, said vector comprising:
   a DNA molecule consisting of an isolated mammalian c-myc insulator element (MINE) of a eukaryotic 5' constitutive DNA I-hyperacelylated domain located approximately 2.5 kb upstream of the c-myc transcription initiation site of the c-myc gene locus, wherein said isolated MINE is a 1.6-kb fragment from upstream of the c-myc exon 1;
   wherein said mammalian c-myc MINE comprises, in 5' to 3' order, a mammalian c-myc barrier element (BE), a mammalian c-myc silencing element 1 (S1), a mammalian c-myc CCCTC-binding factor (CTCF) element, and a mammalian c-myc silencing element 2 (S2),
   a promoter domain; and
   a transgene, wherein the promoter domain and transgene are operably linked, and wherein the DNA molecule flanks the promoter and transgene; and
   where upon transfection the vector is linearized;
   wherein, following the transfecting step, the linearized vector is integrated into a host chromosome, wherein c-myc MINE when flanking the gene inserted into said chromosome insulates the transcriptional expression of said gene from one or more cis-acting regulatory sequences in chromatin into which the gene has been inserted, thereby providing stable, long-term expression of the transgene.

2. The method of claim 1, wherein the MINE is the human MINE of SEQ ID NO: 1.

3. The method of claim 1, wherein the MINE is the murine MINE of SEQ ID NO: 9.

4. The method of claim 1, wherein the mammalian c-myc BE is the BE of SEQ ID NO: 3.

5. The method of claim 1, wherein the mammalian c-myc BE is the BE of SEQ ID NO: 10.

6. The method of claim 1, wherein the mammalian c-myc S1 is the S1 of SEQ ID NO: 4.

7. The method of claim 1, wherein the mammalian c-myc S1 is the S1 of SEQ ID NO: 207.

8. The method of claim 1, wherein the mammalian c-myc CTCF binding site is the CTCF binding site of SEQ ID NO: 15.

9. The method of claim 1, wherein the mammalian c-myc CTCF binding site is the CTCF binding site of SEQ ID NO: 16.

10. The method of claim 1, wherein the mammalian c-myc S2 is the S2 of SEQ ID NO: 5.

11. The method of claim 1, wherein the mammalian c-myc S2 is the S2 of SEQ ID NO: 208.

12. The method of claim 1, wherein the transgene gene encodes a protein selected from a structural protein, an antibody, a membrane receptor, a neurotransmitter, a regulatory protein, a cytokine, an antigen, a clotting factor, a peptide-hormone, an enzyme, and an antibiotic-resistance protein.

13. The method of claim 1, wherein providing a vector includes providing a vector having the DNA molecule positioned 5' to the promoter domain and the transgene gene.

14. The method of claim 1, wherein providing a vector includes providing a vector having the DNA molecule positioned 3' to the promoter domain and the transgene gene.

15. The method of claim 1, wherein the vector further comprises an additional mammalian c-myc MINE, and wherein the first MINE and the second MINE flank the promoter domain and the transgene gene at respective 5' and 3' ends.

* * * * *

```
                              SEQUENCE LISTING

<160> NUMBER OF SEQ ID NOS: 208

<210> SEQ ID NO 1
<211> LENGTH: 1893
<212> TYPE: DNA
<213> ORGANISM: human

<400> SEQUENCE: 1
actagttgta atctcagcca tttttcaacc cagcaaatgt ctattctagg tcaaatatgt      60
ctcaaaaatt actaaaagaa aatcagttat gtcctttaac ctggctgagg tctggctttg    120
ttttctctca tgtaaaaatg gagatggcac aaaacaactc caagctgtta cttgaaagta    180
acacctcagg tgatgtcacc agcctgaggg agagtgaggt taagttctga acccacaggc    240
attatatctg cctggggttc acatgcccta cactggactg cataaatttg agagtcagat    300
ccgaagatgt ggtatatccg ccatctttag caactttcaa aaactacccct atgaggtcaa    360 gctggaccta cttttggttt tgccattgtt gtttgtttgt tgttgagggt tttctttgag    420
gggcggggag tgcatgcccc tgtggagagc actcatttag cttcaattag agtaatgcca    480
aaagtgccag attcctggga aatcagccta caaggctcct gcgggaagga acctccactg    540
ccagaagtcc ttagggcatc taagtgatca gacaccgtca gggattcttt gccccgtaaa    600
aacctacttg accagggaca cgtgccaggt aaatttcctt cacatttact tcaaccttat    660
tgcatactca ttttagtatt aaaaccttta ataaaatgct cctattcctt cacactttt    720 ttctatgaga tctcaaatac cccttcttgc tattaaaaaa aatcacttat tattcaccag    780
cccaatattt taaaagtaaa aataataagc caaggccagg agcgatgact cgcacttgta    840
ttcccagcag tttcagaggc aaaggccgaa ggatcgcttt aaccgaggag tttgagacca    900
gcctgggcaa catgaccaga ctgcctctct acaaaaagtt taaaaaatta accgggtgtg    960
gtggtgcact gcactccag ctactgggct ggggtatcag gctgaggtag gaggtttgct   1020
ttgagcccgg ggggatcgag gctgcagtga gctttgattg tgccactgca ctccagcctg   1080
ggtgacagaa ggagacctgt ctcaaaaata ataagaataa taattaataa taataggcca   1140
aaccaaatac ccatcacctt ctgctgtgcc tcccctttcc ccaataaatc cagtgtcttg   1200 cttttcaaatt ttgtggttaa aaaagatgat gagtttctaa gacgtggggg ctaaagcttg   1260
tttggccgtt ttagggtttg ttggaatttt tttttcgtct atgtacttgt gaattatttc   1320
acgtttgcca ttaccggttc tccatagggt gatgttcatt agcagtggtg ataggttaat   1380
tttcaccatc tcttatgcgg ttgaatagtc acctctgaac cactttttcc tccagtaact   1440
cctctttctt cggaccttct gcagccaacc tgaaagaata acaaggaggt ggctggaaac   1500
ttgttttaag gaaccgcctg tccttccccc gctgaaaacc ttgcacctcg gacgctcctg   1560
ctcctgcccc cacctgaccc ccgccctcgt tgacatccag gcgcgatgat ctctgctgcc   1620
agtagagggc acacttactt tactttcgca aacctgaacg cgggtgctgc ccagagaggg   1680
ggcggaggga aagacgcttt gcagcaaaat ccagcatagc gattggttgc tccccgcgtt   1740
tgcggcaaag gcctggaggc aggagtaatt tgcaatcctt aaagctgaat tgtgcagtgc   1800
atcggatttg gaagctacta tattcactta acacttgaac gctgagctgc aaactcaacg   1860
ggtaataacc catcttgaac agcgtacatg cta                                1893
```

<210> SEQ ID NO 2
<211> LENGTH: 1545
<212> TYPE: DNA
<213> ORGANISM: human

<400> SEQUENCE: 2

| | | | | | |
|---|---|---|---|---|---|
| ctatgaggtc | aagctggacc | tacttttggt | tttgccattg | ttgtttgttt | gttgttgagg | 60 |
| gttttctttg | aggggcgggg | agtgcatgcc | cctgtggaga | gcactcattt | agcttcaatt | 120 |
| agagtaatgc | caaaagtgcc | agattcctgg | gaaatcagcc | tacaaggctc | ctgcgggaag | 180 |
| gaacctccac | tgccagaagt | ccttagggca | tctaagtgat | cagacaccgt | cagggattct | 240 |
| ttgccccgta | aaaacctact | tgaccaggga | cacgtgccag | gtaaatttcc | ttcacattta | 300 |
| cttcaacctt | attgcatact | cattttagta | ttaaaacctt | taataaaatg | ctcctattcc | 360 |
| ttcacacttt | ttttctatga | gatctcaaat | accccttctt | gctattaaaa | aaaatcactt | 420 |
| attattcacc | agcccaatat | tttaaaagta | aaaataataa | gccaaggcca | ggagcgatga | 480 |
| ctcgcacttg | tattcccagc | agtttcagag | gcaaaggccg | aaggatcgct | ttaaccgagg | 540 |
| agtttgagac | cagcctgggc | aacatgacca | gactgcctct | ctacaaaaag | tttaaaaaat | 600 |
| taaccgggtg | tggtggtgca | ctgcactccc | agctactggg | ctggggtatc | aggctgaggt | 660 |
| aggaggtttg | ctttgagccc | gggggatcg | aggctgcagt | gagctttgat | tgtgccactg | 720 |
| cactccagcc | tgggtgacag | aaggagacct | gtctcaaaaa | taataagaat | aataattaat | 780 |
| aataataggc | caaaccaaat | acccatcacc | ttctgctgtg | cctcccctt | ccccaataaa | 840 |
| tccagtgtct | tgcttcaaa | ttttgtggtt | aaaaagatg | atgagtttct | aagacgtggg | 900 |
| ggctaaagct | tgtttggccg | ttttagggtt | tgttggaatt | tttttttcgt | ctatgtactt | 960 |
| gtgaattatt | tcacgtttgc | cattaccggt | tctccatagg | gtgatgttca | ttagcagtgg | 1020 |
| tgataggtta | attttcacca | tctcttatgc | ggttgaatag | tcacctctga | accacttttt | 1080 |
| cctccagtaa | ctcctctttc | ttcggacctt | ctgcagccaa | cctgaaagaa | taacaaggag | 1140 |
| gtggctggaa | acttgttta | aggaaccgcc | tgtccttccc | ccgctggaaa | ccttgcacct | 1200 |
| cggacgctcc | tgctcctgcc | cccacctgac | ccccgccctc | gttgacatcc | aggcgcgatg | 1260 |
| atctctgctg | ccagtagagg | gcacacttac | tttactttcg | caaacctgaa | cgcgggtgct | 1320 |
| gcccagagag | ggggcggagg | gaaagacgct | ttgcagcaaa | atccagcata | gcgattggtt | 1380 |
| gctcccgcg | tttgcggcaa | aggcctggag | gcaggagtaa | tttgcaatcc | ttaaagctga | 1440 |
| attgtgcagt | gcatcggatt | tggaagctac | tatattcact | taacacttga | acgctgagct | 1500 |
| gcaaactcaa | cgggtaataa | cccatcttga | acagcgtaca | tgcta | | 1545 |

<210> SEQ ID NO 3
<211> LENGTH: 1256
<212> TYPE: DNA
<213> ORGANISM: human

<400> SEQUENCE: 3

| | | | | | |
|---|---|---|---|---|---|
| actagttgta | atctcagcca | tttttcaacc | cagcaaatgt | ctattctagg | tcaaatatgt | 60 |
| ctcaaaaatt | actaaaagaa | aatcagttat | gtcctttaac | ctggctgagg | tctggctttg | 120 |
| ttttctctca | tgtaaaaatg | gagatggcac | aaaacaactc | caagctgtta | cttgaaagta | 180 |
| acacctcagg | tgatgtcacc | agcctgaggg | agagtgaggt | taagttctga | acccacaggc | 240 |
| attatatctg | cctggggttc | acatgcccta | cactggactg | gcataatttg | agagtcagat | 300 |
| ccgaagatgt | ggtatatccg | ccatctttag | caactttcaa | aaactaccct | atgaggtcaa | 360 |

```
gctggaccta cttttggttt tgccattgtt gtttgtttgt tgttgagggt tttcttttgag     420 gggcggggag tgcatgcccc tgtggagagc actcatttag cttcaattag agtaatgcca     480
aaagtgccag attcctggga aatcagccta caaggctcct gcgggaagga acctccactg     540
ccagaagtcc ttagggcatc taagtgatca gacaccgtca gggattcttt gccccgtaaa     600
aacctacttg accagggaca cgtgccaggt aaatttcctt cacatttact tcaaccttat     660
tgcatactca ttttagtatt aaaaccttta ataaaatgct cctattcctt cacactttt      720 ttctatgaga tctcaaatac cccttcttgc tattaaaaaa aatcacttat tattcaccag     780
cccaatattt taaaagtaaa aataataagc caaggccagg agcgatgact cgcacttgta     840
ttcccagcag tttcagaggc aaaggccgaa ggatcgcttt aaccgaggag tttgagacca     900
gcctgggcaa catgaccaga ctgcctctct acaaaaagtt taaaaaatta accgggtgtg     960
gtggtgcact gcactcccag ctactgggct ggggtatcag gctgaggtag gaggtttgct    1020
ttgagcccgg ggggatcgag gctgcagtga gctttgattg tgccactgca ctccagcctg    1080
ggtgacagaa ggagacctgt ctcaaaaata ataagaataa taattaataa taataggcca    1140
aaccaaatac ccatcacctt ctgctgtgcc tcccctttcc ccaataaatc cagtgtcttg    1200
ctttcaaatt ttgtggttaa aaaagatgat gagtttctaa gacgtggggg ctaaag       1256

<210> SEQ ID NO 4
<211> LENGTH: 356
<212> TYPE: DNA
<213> ORGANISM: human

<400> SEQUENCE: 4
gcttgtttgg ccgttttagg gtttgttgga atttttttt cgtctatgta cttgtgaatt       60
atttcacgtt tgccattacc ggttctccat agggtgatgt tcattagcag tggtgatagg     120
ttaattttca ccatctctta tgcggttgaa tagtcacctc tgaaccactt tttcctccag     180
taactcctct ttcttcggac cttctgcagc caacctgaaa gaataacaag gaggtggctg     240
gaaacttgtt ttaaggaacc gcctgtcctt ccccgctgg aaaccttgca cctcggacgc      300
tcctgctcct gccccacct gaccccgcc ctcgttgaca tccaggcgcg atgatc          356

<210> SEQ ID NO 5
<211> LENGTH: 254
<212> TYPE: DNA
<213> ORGANISM: human

<400> SEQUENCE: 5
ttactttcgc aaacctgaac gcgggtgctg cccagagagg gggcggaggg aaagacgctt      60
tgcagcaaaa tccagcatag cgattggttg ctccccgcgt ttgcggcaaa ggcctggagg     120
caggagtaat ttgcaatcct taaagctgaa ttgtgcagtg catcggattt ggaagctact     180
atattcactt aacacttgaa cgctgagctg caaactcaac gggtaataac ccatcttgaa     240
cagcgtacat gcta                                                        254

<210> SEQ ID NO 6
<211> LENGTH: 3422
<212> TYPE: DNA
<213> ORGANISM: human

<400> SEQUENCE: 6
tctagatatt tacaaacaaa aaaaaaaact gaaaacaggg ccagacatgg tggctcatac       60
ctgtaatacc agcactttgg gaggcctagg caggtggatc acctgtcagg agtttgagac     120
```

```
caccgtggct aacatgatga aacccgtct ctactaaaaa tacaaaaatt agctgggcat    180
ggtggtgcac atcagtaatc tcagctactc aagaggctga gacaggaaag tcactgaaac    240
ccctggaggc ggaggttgca gtaagctgag atcatgccac tgcacttcag cctgggtgat    300
aagagcaaga ctccatctta aaaataaat aaataatttt tttaaaaaag gaaacatatg    360
tccatgcaaa gacttctacg tgaatgctta tagacacttt atttgtcata ttcaaaagct    420
aaaagcaacc acatgtctat ccctgggcga atgaataaat gtattgtggt atatccgtac    480
aatgaaatac caactcagaa ataagtaaaa gagccagaca aaaagagttc actctgtatg    540
cttccattta tataagattt tacaaaatgt aaactaacat atggtgggga aagggtgcaa    600
caacagaagt cactacaaag ggacacagga tgcttttggg ggtgatagat atgttcatta    660
tcttgattgt ggggatggat tgtggatgt atacatatgt aaaaacacca aatcgtatac    720
tttaaataca tcagcttact gtgtgtccat tatacctcag taaagttgat ttaaaaagaa    780
agatgcggcc gggcatggtg gctcaacact gtaatcccag cactttggga ggccgaggtg    840
ggcagatcac ctgaggtagg gagttcaaga ccagcctgac caacatggag aaaccccgtc    900
tctactaaaa atacaaaatt agctgagagt ggtggtgggt gcctgtaatc ccagctactc    960
gggaggctga ggcaggagaa ttgcttgaac ctgggaggtg gaggttgtgg tgagccgaga   1020
tcacgccatt gcactccagc ctgggcaaca agagtgaaac tctgtcttaa aaacatata   1080 tatatgaaga aagattcctg atatactgaa aaagtgtcaa gatgggggaa aaaaaacaaa   1140
agcaatgaga tacagaagaa gagatatagg ggagacttga atcccaagtg ctctaaaagc   1200
agacaaatgc tgctaatcac tttatcaccc aaaactggac ttcagtctac cagagttcag   1260
gcagatggaa agtagactga gaaaatgctg aaaacaaatt gatgtgctat aaactggaat   1320
aaaattcaaa gtatttgcac aaagctgttc tacacagaga gctgtatgat tctaaaaatt   1380
taattactta cttagaaaat aacacacaat acacacacac acacacacac acacacacac   1440
acacgagctt aaaaacagtg ccagtaactg gtatgacaag agatgaatac atttaaaacc   1500
aacccaatgt ctggctggaa gcagtcattc tgagcttctg acattgctaa tacatcagac   1560
agaggcagca ggaagagttc cactgaggaa gattcaaatg caatttgaga aaccaaacag   1620
gtaccagtga gttaagggat cagcccttga gaatgagggg agatgagacc cagcagaggg   1680
aaggcaggga agaaggcaaa gcaggtgtta atttcactac ctagcagcaa ggctgaaact   1740
cttgacagct acaattgcca ataggcaggc atcagcttct aatgtctgct cttagttgtt   1800
acagatcaac aggtctgaaa gggttcatct ggtgttcccc tcattttta aatttttatt   1860 tcaatagttt ttggggtata agtggtttgg gattacatga ataagttctt tagtggtgat   1920
ttctgagatt ttgatatgcc catcacccga gcagtgtaca ctatacccaa tgtgtagtct   1980
tttatccttc atcccccttc caacttccct tctactgagt ccccaaagtc cattatatca   2040
ttgtaatgcc tttgcattct catagcttag ctctcactta taagtgagaa catatgatac   2100
ttggttttcc attcctgagt tactcactta gaataagggc ctccagcttc atccaagttg   2160
ctgcaaaaga cattatttca ttcctttta tggctgagta gtattacaca gtgtagatat   2220
gccacatttt ctttatccac tcattggtta atgggcattt agattggtac catattttg   2280 caaatgcaaa ctatgctgct ataaacatgc atgtacatgt gtctttttaa tataatgact   2340
tcttttcctt tggatagata cgcagtagtg ggattgctgg atcaaatggt agttctactt   2400
ttagctcttt aaggagtctc catgctgttt accatagtgg ttgtactggt ttacatctcc   2460
acccgcagca taaaagtgtt cccttcttac cacatccgtg ccaatgtcta ttgtctaggt   2520
```

-continued

```
gtgacaaacg agttcactaa agtctcagga tataaaatca atgtacacaa ataagtagca    2580
cttctctaca tgaacaatga tcaagctgag aatcaaataa agaactcaat tcccttata     2640 ataggtacaa caaataaaat aaaatactta ggaatagagt taaccaagga ggtgaatgac    2700
tgctacaagg aaaactgcaa aacactgctg aaagaaatca tagacaacac aaatggaaac    2760
acatcccatg ttcatggacg ggtagaatca atattgtgaa gatgatcata ctgcccaaag    2820
caatctacaa attcaatgca attcccatca aaataacatc atcattcttc acagaaatag    2880
aaaaaaaatc ctaaaattca tatggcatct aaaaagtccc ccttgttttg aaaacaaaga    2940
aacttaaggt ttgagggtta aggtggtctt caaaaaaaaa aatctagctt ttcatgactg    3000
tgtaccacag caacaccctc tttgaaaaga ctctgagagt cagctcaggc gatgctagag    3060
ccagactccc tggtcttaca tcctgtgtct tgtgtttccc ctactcctga aagtgcaact    3120
ttgggcacgt tattaagcat ctcacttct ttaactgtaa aatgaggcaa ctaataatac     3180
cacctcatta gggttgttaa gtcagggttc tctggagaaa tagaacccat agggcatgtg    3240
tgtgtgtgtg tgtgcgtgca cacacgcg tgcacacatg cacacaaaga gaaagtttta     3300
agaaactgtc ccacacaatt gtggaggctg agaagtccaa aatctgtagg gtaggtgggc    3360
tggctgaaga cccagagaag aatcacagtt ccagtccaaa agctgtctga tggcagaatt    3420
cc                                                                   3422

<210> SEQ ID NO 7
<211> LENGTH: 10723
<212> TYPE: DNA
<213> ORGANISM: human

<400> SEQUENCE: 7
agcttgctaa aactctcagc aagccccaaa cagagctgca gtgtgtggag ttctggatca      60
aagcctgcct gctgaaagta gaaagtactg agtttctact aatgaggccc attcagcgtc     120
tagtcaaatc tttctctatt ctgtgcctgg cgaacacggc aatttgttat caacccacag     180
agtgagctgc agataaatgc tctctgatcc tatctttggt aaaacctgta atttacaggc     240
tatcttaggg gataactgta attggaactt ttacgttatg ttttacttc agttgtgatc      300 acccacagct ccatttgctt agatacatct aaagggcacc tgtacttggg tctagttttg     360
accttgtact tggtgtgagt gtgtgtgact gcatgtgagt gtgtgttcat acatacacac     420
ataccctttt gtgaaattcg cacatatata aatatgaaat gggtaactac tttatttgct     480
ttgtttctgt taagcctaga gaaagctggt aatcccagag acactggaaa taccatttcc     540
atatagagcc agtaatctca ttattaggtt tatacccaaa ggattataaa tcattctact     600
aaagacacat gcacgtatat gcttattaca gcactattta caatatcaaa gacttggaac     660
caacccaaat acccatcaat gatacactgg ataagaaaaa cgtggcacat atatgccatg     720
gaatactatg cagccataaa aaagactgag ttcatatctt ttgcagggac atggatgaag     780
ctggaagcca tcattttcag caaactaaca caggaacaga aaccaaaca ccacatgttc       840 tcactcataa gtaggagttg aacaatgaga acgcatggac aggggaggg aaaaatcaca       900 tactggggcc tgtcggggt ggggacaag gggagggagg gcattaggac aaatacctaa        960
tgcatgtggg gcttaaaacc tagatgatgg gttgacaggg ggagcaaacc accatggcac    1020
atgtatacct atgtaacaaa gctgcatgtt ctgcacatgt attccagaac ttaaaataaa    1080
attatatata tataatatat gtatatatta taatatgt gtatatatac atatattata      1140
atatatgtat atattatacg tatattataa tatatgtata tattatacgt atattataat    1200
```

-continued

```
atatgtatat attatatata atatatatat atgttagttt ataatggtct ccttcaggaa   1260
tggaaaagaa aagtaaagaa agtttcatct actaggcatt ttcttaccat gttaatctct   1320
ctcatatacg tgatctcatg aattcttcac aagaacctga gagatggcta ctatgacaat   1380
tcatttaatt tcatgtgtca acttgacagg gtcagggat ctccagagag ctggctaagc    1440
attgtttctg ggtgtgtggg tgaaagtgtt cctggaggtg atttgtatct gaattggtag   1500
actgggtaaa tatcaccctg tccagtgcag gtgagcatca cttagcctac tgaaggcctg   1560
aatagatcaa gaaggcagaa gacaattgga tttgctccct ctcttcctgg ctgctggagc   1620
tcaattgaac ttcccctgcc ctcagcacgc ctaattctca gaactcaggc tagcattgga   1680
atctatacca agactctcag actttccagc gacaccacca gctttcctag gtctccagct   1740
tgcagacagc agatcgtggg actttccagc tgccataacc atgtgagctc aatcctcata   1800
ataaatctct ttttagcaat aagaaagata gatagataga tagatagata gataagatag   1860
ataaatatca cctcagaatt gtagttgaga aatctgtaac tctaaaaccc atacaggccg   1920
ggcttgatgg ctcatgcctg taatcccaac actttgggag gctaaggtag gtagattgct   1980
tgagcctagg agttcaagac cagcctacgc agcatggcga aacccaatct ctacaaaaaa   2040
atattgaaat taatggggct tggtgacaca tgcttatagt cccagctact gggaggctg    2100 aggtgggatg atggcttgag cccaggaggt tgaggctaca gtgagccagg atcatgccac   2160
tgtacttaca gtctgggaga tagagagaga ccctgtctca aaaaaataaa ataataaata   2220
agtaaataaa acccatatga ttttcatgaa accacatttc ttcttgaaga gagtaaaaaa   2280
gggatgaaag aaaaatggag ttatattctt ttccttgagg ataaaaaaaa gtacactgaa   2340
aactatccca tggcttagga attagcctag actcaactgc ctattttgtt ggcagctaaa   2400
atctcatctt cttctacttg ttcaacctca gagaatcaat caacaatcag gcagccattg   2460
tattaatagc tgttataagc catagtaatg gaaaattcaa aagaataata gtttggactg   2520
tgtatggttt cagaaggtat ttttttactac ttttactgtt aggaatgact agaaaatcat   2580
tcccagcacc tccagcaaac tattgactcc acactagcct tcaattcttg agaaaagagt   2640
gtgaactaag gtcacttggg gctccacttt cttttctttt tctttttttt ttttgagacg   2700
gagtctggct cttgtccccc aggctggagt gcagtggcat gatctcggct cactgtaacc   2760
tccgcctccc ggattcaagt gattcttctg cctcagcttc ccaagtagct ggaactacag   2820
gcatgcgtca ccatgcccag ctaattttttg tattttttagt agagacaggg tttcaccatg   2880
ttggccagga ttgtctcgat ttcttgacct tgtgatccac ccaccttggc ctcccaaagt   2940
gttggggtta caagcatgag ccaccgcacc cagccagggg atccacttc atggtggtgg    3000 actcacatgg gtggtaggta ggttggtgcc agctgtcagc tgggagctgt gctgggactg   3060
tgtgctggga gcctgggttt tgccatagct ttattgggtt tccttgcggc atggtagctc   3120
gggttttttt gttttttgtt ttttgttttc atggggtctc tctctgtggc ccaggctgca   3180
gtacagtggt acgatgatgg ctcactgtag cctcaacctc ctgggttcag gtgatcctcc   3240
cacctcagcc tcctgagtag ctgggactac aggtgcatac cagcacacct ggccaatttt   3300
tgtactttct atcacaatgg ggtttcacaa tattgcccag gccaggttag ttcagttcta   3360
agaatgagtg gcccaagagc tccagagagg cactttgtta cgctttatga cccagcccca   3420
gaagtcatag tatcacttt tttgtagtca caagcccagc tagattcaga gggaacattg     3480
aatctacctg tcagtggaag gaaaaccaac ccacactgca aaaagagatg agagactttc   3540
ttaaggccat ttttgggaag tacagtttgc cacagagtgg tagtaacgag ttaaacattt   3600
```

```
tatgaataat atgtgtttag atgcctggta gagtacctgg catgtagcag agacccaatt    3660
tgtggtggct ggtttacaca cggatatgga accaaggcta gtcagaatct caggggaggc    3720
cttcaacagg tcaacaggta ttcagggtcc agtgattttc agatagccta ttttgcggtg    3780
atctggatca cccttgctct cacctcacaa tcataataaa gagtgtgacc gtcctgacat    3840
tttgctttct gtattgctct ccttttccgt cagttcataa cccacatatt tggtcgatca    3900
tgagaatgac cagagacagg caacactgtg gcattgttta gtcacatccc atttgtctca    3960
tggctgggtc tatccaaact gtcttgtata ggttggctcc aacacagttt gtctacagtg    4020
tgtgaaagtg gatgttagtg ataagacagg atgtgaactt gacctactgt cagtcaaata    4080
ggaggttttg gcatggagcg cttctgagcc actccgtctc agctgtagag atgccagtat    4140
agcaacagag cttctctgtt caactgattt ggagctggaa agaaccctcg aaaagggcca    4200
gagacagaac ggcacttgcc caaggtcata gagggattta atgtcagagt catgaattag    4260
agcagggttt cccagcctca ccactattca cattttattt atttatatgt ttttaaatat    4320
aaacaaaatg ggctcagagg gtaactattg atatttattt atttattatt ttaagatgga    4380
gtcttactct gttgcttatg ctggagtgca gtggcgcgat ctcagttcac tgcaacctcc    4440
acccaccggg tttaagtgat tctcctgcct cagcctctca gtagctggg attacaggca    4500 ggtgccacta cacccagcta attttgtat tttttttaa tttttattta tttattttt    4560 tgagacggag tcttgctctg tcgcccaggc tggagtgcag tggcacgata tcagctcact    4620
gcaagctccg cctcctgggt tcacgccatt ctcctgcctc agcctcccaa gtagctggga    4680
ctacaagcgc ccaccaccac gccctggcta atttttgta tttttagtag acggcgtt    4740 tcaccatgtt agccaggatg gtatcgatct cctgacctcg tgatccgcct gcctcggcct    4800
cccaaagtgc tgggattaca ggcgtgagcc actgcgccca acaattttg tattttagt    4860 agagatcagg tttcaccatt ttggccagga tggtcttgaa ctcctggcct caagtgatcc    4920
actggcctcg gcctcccaaa gtgttgggat tacaggcgtg agccaccgct cccagccact    4980
actgacattt agaccagaaa attctttgtt atgagagggc tgtcctgtgc attgcagaat    5040
agttagaagc atccctggcc tctatatatc aaatgctgtt agcatcattt tctccatttg    5100
taatggccaa aaatacccttt ggatactgcc aaatgtctcc tggggccagg ttgggggat    5160 tacctacaat agagaaccac tggactaaaa ttcaggtcct ctagttgctt gtaaatctat    5220
ccagctaaaa tattatttg ctaaaaattt ataaagacca aattcagatg ctgaattggt    5280
agggctttac tgtagaaaga aaacacacac acacgaaaag acaagttaaa atatagaatc    5340
gtctacgaga taacaggcct gatttctcca aaagtcaaa gtcatgaaaa aaaggaggca    5400
ggaatgactc ttggagatta aaagagactc atgaccttgt ccttgattgg acctggtttt    5460
agaaaaacat agctagaaaa gatatttgag agacagttgg aaaaatttga ttatgctatt    5520
attgtttaat ttttttaagt gtggatatct tgttgtggtt aagagaatgt ccttgttttg    5580
gggacatgca tgttgaaata tttagcgata atctgtaact tactctgaaa taaatatctc    5640
agccatgaaa agtaatcaaa tatgaggaaa tgttaataat taatgaatct acattgtaga    5700
tctgtaatat tctttttct gtatgtgtga aatgttttt aaaataatgt gaataatata    5760
aataaaataa aggtaaaatt agaagaaaaa aattgaagtt ttctgaagtt cacaaagatg    5820
ttcattgcag caatgtacat aatagaaaaa aaaatcagaa gcaaccctaa ctatttatcc    5880
ctaagcaact cctaagcacg gttaaataaa ttctggtatt ctagagaggt agaatacatg    5940
caacatttac aaagagaaag acacagacat cttttttttt tttttgagac agagtctttc    6000
```

```
tctgtcactc aggctggagt gcagtggagt gatctcagct cactgcaacc tccatatcct    6060
gggttcaagc aattctcatg cttcagcctc ccattggctg ggattacagg catgcaccac    6120
cacacttggc taattgaaag atacaaacct ctgttgacaa gcctgaatgt gcaaacagga    6180
gtgaaaatat tatgaatcaa taatgactgt caagagtttc cctcatcctg ggacatcagt    6240
tttcatgagg gcagccggag ttaccaactc taattctcag attggcaatc ggtagctgtg    6300
atgcagcagc tctgtggatg ctgagccatc caggatgaga ccatacgtga tggaaatgta    6360
aatctcagcc cagtgatgat ctatactgca agaaatacca ctttctttat tttctgaata    6420
ttgactttgc attaaacttc cattccattg ggatagtaaa attcccacct ctggaaatgt    6480
agcatttcct ttttctcagg atctgtctct ctggaggaga ttttgggtta aaccatctaa    6540
catggcatat atatatttaa ataataata atataatata taatttaatt aatatataat    6600
atattaattt atatataaca tataaatata tattttaaaa tatatattta aattatatat    6660 atatttttt ctttttttt ttttaagaaa gagtcttgct ttctcaccca ggcttaagtg    6720
cagtggtgca atcacagctc actgctgcct tcacctcctg ggctcaaata atccttgtgc    6780
ctcagcctcc agagtagctg ggactgcagg tgcaagccac catgcccggc taatttttat    6840
atttatagta gagacagggt tttgtcatgt tggccaggct ggcctccaac tcctgtgctc    6900
aagtgattca ccttcttcag cctcacaaag tgctaggatt acaggcatga gccaccacgc    6960
atgaaaaaat ggccagtatg tttaaccttc caaaattcca acttcataca gtttaatcta    7020
aaacatagga ccatgttcat ttgaatgggg atggggaagg gactgaggag agggaaaatg    7080
gaatagaact ggatgtccta atatggatgg cttttccaaga caaattcatt attgagaatg    7140
tgtacataca tatgcaaaca gataggctgc cgaccactga gtgaaaatag cttataataa    7200
tataagaagg ctgggcacag tggctcacac ctataatctc accccttggg gagactaagg    7260
tgggaggatt gcttgagccc aggagctcaa gaccaggttg gcaacgtgg caagaccccg    7320 tctctacaaa attaaagaaa agaaattagc cgagcatggt ggtgttcacc tgtagtccta    7380
gctacttggg aggctgaggc aggagaatca cttgagccca ggtgtttgag gctgtagaga    7440
gctatgctct tcagcttgaa tgatggagtt aggccctgcc tccaaaaaca aataataat    7500 aataatataa gaaaggcaca catggaacaa ggctatgtat tttcttgagt gtttgtgtat    7560
gtgtgtatat aaaaaatata tgtatagatg tgttatacat atacacgaac atgtatatat    7620
attttatatt taaaatggtg gaaaatataa aatccaaatg gaccacaatg actgccttgg    7680
ggaatcagag atttgtagtg agtgctgtaa tgtgctgttc aaattagtcc gtcatgacca    7740
agacagtgat tacctcagct ggcagcagtg ctgctcgctg ccttccagtc tgagctgact    7800
tctccaaggt tctgcccctt ctccaggggc agcctacctc caggagtgcc aaggcaaagt    7860 cccccttgccc caactatgaa cctctccaaa ggaccatctc agtggcagag ctccctgtgg    7920
ggttggctaa ggcctctgag acccatgtta atcccaaagg cactgtctaa taatcctcct    7980
gcatgcatat ctgcatcttg tttgtttggg tttttttttg tttttttttt tttttttttt    8040
tgagacgagt ctccctctgt cacccagggg ctggagtgca gtggagctat cccggctcac    8100
tacaagctcc gcctcccggg ttcacgccat tctcctgcct cagcctcccg agtagctggg    8160
actacaagtg ccgccaccac gcccggctaa ttttttttgta tttttagtag agacgtggtt    8220
tcaccgtgtt agctaggatg gtctcgatct cctgaccttg tgatccgccc gcctcagcct    8280
cccaaagtgc tgggactaca ggcatgagcc accgcacctg gccgggtttt ttttttttt    8340 ttttttagat atagtcttgc tctgtcatcc aggctggagt gcaatagcac gatctcggct    8400
```

```
cactgcaacc tccgcctccc aggttcaagc gattctcctg cctctgcctc ccaagtagct      8460
aggattatag gagtgcgcca ccatgcctgg ctaattttt gtattttaa tggagacagg        8520 gtttctccat gttggtcagg ctggtctcga actcccgacc tcaggtgatc tccccacatc     8580
agcctcccaa agtgctggga ttacaggcgt gagccaccgc acccagcctg atttagcttc     8640
taaaattgta ctgctgactg ggcgtggtgg ctctcatctg taatcccaac actttgggag    8700
gccaagttgg gaggatcacc tgaggtcgga agtccgagac cagcctgaca aacatggtga    8760
aaaaccatct ctactaaaaa gacaaaaaat tagcctggcg tggtggtgca cgctactcgg    8820
gaggctgaga caggagaatt gcttgaaccg gggaggcaga ggttttggtg agctgtgatc    8880
atgccattgc actccagcct gggcaacagg agtgaaactc catctcaaaa aaaaaaaaaa    8940 caaaaacag ctaaatcagc accattactg cttactcaca agcatttaat ggcttgtatc     9000
ttaccgaatg cagtcttgtg cctcacgcaa cattgtcctc cagcccctac acaatgtggt    9060
gctccattac tctgtgacct tagtgctgct tctctctcac taggtctttc tgtaccactc   9120
ctactggcat cattgctgcc cctccagcct gctaggcaaa ctcccatctc agggcttttg   9180
cacttactct tccttccacc tgaaagattc ttatgctaaa tattcacatg actcactccc   9240
tcacttcgcc tagactttaa ataatattac tatctctgta aagtcttcct caatctccct   9300
aattaaattt gtaaaggcca ggtgtggtgg cttgctcctg taatcccagc actttgggag   9360
gctaaggcta aaggatctct tgaggccagg agtttgagac cagcctgggc agcatagcta   9420
gatcctgtct ctacaaaaaa tttaaaaatt agctggttgt agtggcatat gcctgtagtg   9480
ctagcttctc aggatgctta ggtgggaggt tccctggagc ccaggaggtt gaggctgcaa   9540
tgaacagtga tcatgtcact gcactcagcc tgggtgacag agcaagatcc tatttaaaaa   9600 aaaaaaatg tagatcactg tgtgaagttc tcccatttca ctgatgagaa actgcgacct    9660
tgagaggcag gtgtctagtt taataacgca ggaggagcag aaaacagatg tcccttttct   9720
tggcacttct caccacagct tctgtcttta gtatatgtaa ttttttttag gagccaagaa   9780
attccatgat ggcaatttaa aaagcaatca gcttcttttgt gtttgaccaa tgacggatga   9840
gcacatggtt ttgtttgcta tagataaact gagttgatca agacatcaaa gacttcctgc   9900
tggatgggcc agtccaaccg gcttatggta tttagagttg atgtcaatgc attaaaaag    9960 gtaataaatt aaccccatta ttcttggcca tttataagaa actgctcctg cttgggagaa  10020
cctgtgcttc tggttctgga ctaagaattg ctcaacctgg acctcattaa tagggcaaga  10080
gctcagaaga gcatccatct ggcttggatt accttcaagg atggagaaaa tggagcatta  10140
ttctctagtt aatactgaaa acacccagta taatgcatgg taactagtaa gctctcaaaa  10200
aacatctgct gaatctaaat taaaaacagc aacaatgaca aaacctttct aaaatgtttt  10260
gcttaggcta gaggccgggg ctcatgcctt aatcccagca ctttgggagg ccgaggcagg  10320
tggaccacct gaggtcagga gttcaagacc aacctggcca acatggagaa accccatctc  10380
tactaaaaat acaaaagtca gctgttcatg gtggttcaca cctgtagtcc cagctactcg  10440
ggaggctgag gcaggagaat tgcttgaacc caggaggcag aggttgcagt gagccaagat  10500
cgcaccactg cactcctgcc tgggctatgg agcgagactc catctcaaaa tatatatgta  10560
tatatttgcc tcattttgt tataatatag tggtttataat tatgaactct ggaataagct  10620
gagtgatctt aaataaacca ctgaaacttt aggtacctca atttcctctt tgacaaaatg  10680
ggattaataa tagtgtttac ctcataggtt gttgtgagaa ttc                     10723
```

```
<210> SEQ ID NO 8
<211> LENGTH: 1167
<212> TYPE: DNA
<213> ORGANISM: human

<400> SEQUENCE: 8
accaccacac ttggctaatt gaaagataca aacctctgtt gacaagcctg aatgtgcaaa      60
caggagtgaa atattatga atcaataatg actgtcaaga gtttccctca tcctgggaca     120
tcagttttca tgagggcagc cggagttacc aactctaatt ctcagattgg caatcggtag     180
ctgtgatgca gcagctctgt ggatgctgag ccatccagga tgagaccata cgtgatggaa     240
atgtaaatct cagcccagtg atgatctata ctgcaagaaa taccactttc tttattttct     300
gaatattgac tttgcattaa acttccattc cattgggata gtaaaattcc cacctctgga     360
aatgtagcat ttccttttc tcaggatctg tctctctgga ggagattttg ggttaaacca     420
tctaacatgg catatatata tttaaatata ataaatata atatataatt taattaatat     480
ataatatatt aatttatata taacatataa atatatattt taaaatatat atttaaatta     540
tatatatatt ttttcttttt tttttttta agaaagagtc ttgctttctc acccaggctt     600
aagtgcagtg gtgcaatcac agctcactgc tgccttcacc tcctgggctc aaataatcct     660
tgtgcctcag cctccagagt agctgggact gcaggtgcaa gccaccatgc ccggctaatt     720
tttatattta tagtagagac aggggttttgt catgttggcc aggctggcct ccaactcctg     780
tgctcaagtg attcaccttc ttcagcctca caaagtgcta ggattacagg catgagccac     840
cacgcatgaa aaaatggcca gtatgtttaa ccttccaaaa ttccaacttc atacagttta     900
atctaaaaca taggaccatg ttcatttgaa tggggatggg aagggactg aggagaggga     960 aaatggaata gaactggatg tcctaatatg gatggctttc caagacaaat tcattattga    1020
gaatgtgtac atacatatgc aaacagatag gctgccgacc actgagtgaa aatagcttat    1080
aataatataa gaaggctggg cacagtggct cacacctata atctcacccc tttgggagac    1140
taaggtggga ggattgcttg agcccag                                        1167

<210> SEQ ID NO 9
<211> LENGTH: 1990
<212> TYPE: DNA
<213> ORGANISM: mouse

<400> SEQUENCE: 9
caaaaaggac cttttgaggg tcagctctac ccactgtcat atctgttggt gctgtcctgt      60
gtttagggag aggcagagag aaagcgggtg tgcgcaacct ctaagagagt aatagtaaag     120
agacaagcct aggaaatctt ccccaagagg ccttttgggg aaggctatcc cccctttccgt     180 ggatgttgaa taccttgcct gttgctcaga tgcagtcaag catctgatga tgcttgaggc     240
atgatgctga gaccactgtg taggttggta caaattccct ttctattata cccaccctta     300
tgcagttatt tgggtttaaa ttttcaacgt tttaaaaaaa aaaaaaaaaaa gtattgccgg     360 gcaatagtga cgcaggcctt taatcccagc actcgaaaga cagaggcagg cagatctctg     420
agtttgagac caacctggat ggtctaaggc cttgaactca agagatctat ccaccagctt     480
gtatcccatt taattgagtg atttgtttgc tctctctctc tcccgctccc cctctctccc     540
ccctctccct ccccttttt c agttcttat ttatatttga atattatctc tctctcagat     600
gtgtacttgg tgacggtctt ttctacaaag gattatctgt ttcatgacac gccatttatt     660
aatctgcttg tccctggagc ttctgtacag tagcgtgacc tgatcctcta gcttctccat     720
cccagatgat tgggattcaa ggcattcatc accacgccta cctaaaattc caaccttta     780
```

-continued

```
ataaaatggc tctctaaaat attttggcaa aggaatctca ctctttctct tcactaatat      840
agttcaacca cccaattcgt aagcagtcgg gctgagggtg agcatcctta agaacataaa      900
agcaaaattt ggaggctcaa gattcagttt agttgctaga gggctcacat agcatgccct      960
ccccacccgg gattccattc tcatttatcg aggcataagg ccaggtgtgg tgggatatgt     1020
gctgggatgc ataagatctt ttataaagaa gaggaagagg aaaaacagtt atacaaaact     1080
aataaaactg tgtgagtttc aggctagcaa agaatagtcg tgagaatctc tctcaaaaaa     1140
aaaaccccaa aataataata atgataataa tgataataat aataataata ataaaacaag     1200
gcaataataa gctaatgctc ctgccttgca ttctgactcc ttttgcccag taaaattcaa     1260
tgctctgctt tgacacgtcc agcttacaac acgacaaagg tgtgagacat gggtgctaaa     1320
acttgttcta ttgcctttcc gtttctgtta gatctccttc acttgtatac ctgtgactca     1380
ttcattttcc ccatccacaa ctagggctct gttttgggtg actgtcagaa agtagggatg     1440
ggttcatcta ctcccctct ttgcaactga atagccacct ctgaaccatt tttttctcta     1500
gtaatttctc ttcctttgcc tccttttgcag cctaaaagag tcatttaaag gatgaccgga     1560
agcttgtctt aggcaaggaa gcatcttccc agaacctgga aaccctgcag ccctgccccc     1620
atccgacctc cgccctcgtt ggcttcgcaa cgctgtggtc tctgtggcca gtagagggca     1680
cacttacttt actttcacaa atccgagagc cacaacccgg gtggtggggg gtgagggggc     1740
ggggaaagag tctctgcagc aaaacgcaga ctagggattg gtggctcttg gtgtttgagg     1800
caaaatccta gaggctgtag tcattttgca atccttaaag ctgaattgtg caatgagctc     1860
gatgaaggaa gatactatca ttcaacagct gaatcctaaa ttgcaaactc agtggctaat     1920
aacaactttg aacaatgagc accttataca cgctactgta ttttctttc tttctttttt      1980 tttttttttt                                                           1990
```

```
<210> SEQ ID NO 10
<211> LENGTH: 1565
<212> TYPE: DNA
<213> ORGANISM: mouse

<400> SEQUENCE: 10
```

```
caaaaaggac cttttgaggg tcagctctac ccactgtcat atctgttggt gctgtcctgt       60
gtttagggag aggcagagag aaagcgggtg tgcgcaacct ctaagagagt aatagtaaag      120
agacaagcct aggaaatctt ccccaagagg ccttttgggg aaggctatcc cccttccgt       180 ggatgttgaa taccttgcct gttgctcaga tgcagtcaag catctgatga tgcttgaggc      240
atgatgctga gaccactgtg taggttggta caaattccct ttctattata cccaccctta      300
tgcagttatt tgggtttaaa ttttcaacgt tttaaaaaaa aaaaaaaaa gtattgccgg       360 gcaatagtga cgcaggcctt taatcccagc actcgaaaga cagaggcagg cagatctctg      420
agtttgagac caacctggat ggtctaaggc cttgaactca agagatctat ccaccagctt      480
gtatcccatt taattgagtg atttgtttgc tctctctctc tcccgctccc cctctctccc      540
ccctctccct cccctttttc agttcttat ttatatttga atattatctc tctctcagat      600
gtgtacttgg tgacggtctt ttctacaaag gattatctgt ttcatgacac gccatttatt      660
aatctgcttt ccctggagc ttctgtacag tagcgtgacc tgatcctcta gcttctccat      720
cccagatgat tgggattcaa ggcattcatc accacgccta cctaaaattc caaccttta      780 ataaaatggc tctctaaaat attttggcaa aggaatctca ctctttctct tcactaatat      840
agttcaacca cccaattcgt aagcagtcgg gctgagggtg agcatcctta agaacataaa      900
```

```
agcaaaattt ggaggctcaa gattcagttt agttgctaga gggctcacat agcatgccct    960
ccccacccgg gattccattc tcatttatcg aggcataagg ccaggtgtgg tgggatatgt   1020
gctgggatgc ataagatctt ttataaagaa gaggaagagg aaaaacagtt atacaaaact   1080
aataaaactg tgtgagtttc aggctagcaa agaatagtcg tgagaatctc tctcaaaaaa   1140
aaaaccccaa aataataata atgataataa tgataataat aataaataa ataaaacaag    1200 gcaataataa gctaatgctc ctgccttgca ttctgactcc ttttgcccag taaaattcaa   1260
tgctctgctt tgacacgtcc agcttacaac acgacaaagg tgtgagacat gggtgctaaa   1320
acttgttcta ttgcctttcc gtttctgtta gatctccttc acttgtatac ctgtgactca   1380
ttcattttcc ccatccacaa ctagggctct gttttgggtg actgtcagaa agtagggatg   1440
ggttcatcta ctcccctct ttgcaactga atagccacct ctgaaccatt tttttctcta    1500
gtaatttctc ttcctttgcc tcctttgcag cctaaaagag tcatttaaag gatgaccgga   1560
agctt                                                              1565
```

<210> SEQ ID NO 11
<211> LENGTH: 2979
<212> TYPE: DNA
<213> ORGANISM: mouse

<400> SEQUENCE: 11

```
taaaggcttg tggtggcttc acaaagagaa aggatggcac ctagaatggt aagatgcaag     60
cacactgaaa actaacggag gaaggagctt agggcttgat gcctagtact gcaggggaat    120
gaatcaatag gggctgggga ggtggatcaa tcagttgaat gcttgccgtg caagcatgag    180
aacctgagtt cagataaaga gcccggtgca gtgtgacata ctggtaaaac cagttctgga    240
gaggtagaga cttaatggtt agccagtctt gccaaatcag tgagctccaa gttcaatgac    300
agaccctgtc tcacaaaata ataataataa taataataat aacaataata ataataataa    360
taataaagtg gagagtgatt gatgtggaca catgacacca acctctgtcc tctacatgta    420
cacacaaaag aaaatacaaa taataaatg aatgaataaa taataaaata atccaaaatg    480
catataaata aatgaataaa taaatcatct aaattgcaaa taaatgaatt cacgaataaa    540
taaataattg aataaataaa tactctaagt gccagactgg atatgcccat ccttcttctc    600
tgatagagct accatgtctg aaatgaggat ggacagctct gctggagaag acaagaatgt    660
gagttgagag atcgaaatgg gcacgattgg agcttgaaga tgagaatgag aagggagagc    720
tatgcccttt tgcatgacga tctgacctga ggcccagtgg atagtggata gctgttagaa    780
tggccagtgg cagcatgagc tgctagggcc tggttctagt gtgtgtgggt tgaataaggc    840
tggcaggggc ccataacctt caacttggaa ataaagaagc taggttccta acagaggtgg    900
ttttccattc tgcactgctc atcctaggat gcagggaat gctatgggtg gatatcctga    960
tctgatagtc tgtctgccat ttttcctaga agcatgaact cggccctatt atgaagcctt   1020
ttactttcct cacttgtatg agaaactaag aaaaactacc ttgctgaaat catttcattg   1080
ggctttcaaa tgcataggaa agagaggaag acttgctgag atttttaaaga cttattgagg   1140 ttggtgaatc caaactctac tccacagaag acatctgcag gctggaaagc aagaaagcac   1200
aaagccatct gttggcagaa ttccttcctt ctcctatcg tctgctcttt ctctattaag    1260
acttttttct ggtttaataa aaagctacct acataatgga tggtaatggt ctttattcag   1320
tctacttctg tcaatgttca cttcatttag aaatttcctt tccagaaaca tgtagaaata   1380
atgcatgatc aaaggtctga ttatcgtagc tcaaacaagt taatatcaaa aattaactac   1440
```

```
ctctggatgc tatgagaaaa gcacttgtag gggttttatc catgcaaatt tcatgacaat    1500
catgcactaa cttcaattat gtccaaggga cctcattctc ttccttctcc ctcttcttta    1560
cgcttctctt cccactttac aaagctctcc cgaggctgag tggaggtgcc attgacatcc    1620
tcagctaccc tgctctggca agatgactca gcaggtggaa gctccttgcc agcaagcctg    1680
atgacctgag tttgatcctc agaaccaaga tggtgaaagg acagaatttc aggttgccct    1740
atgaccacaa gtgctccatg gtacatgcac acataacaaa caaacaaaga aacaaagaaa    1800
aatgtttagt gggcagaaaa tccctcccaa agaataaggc actttacttg ctcttcatcc    1860
ttatctgttt cagatcccaa cagagttccc caaacagctc tggtctccct acctcgtctc    1920
tattgagtgg cagtcagcat tggttctcta agtccttgat cattctggtt tctagtatgc    1980
agctacaatc ttttcacatc ccattccttt gaagtatact cctgcagatg gtgttcaact    2040
atctcaactg cttccaccta gtgatgggtg acatttttcaa tttcatgggt ttcctctgaa   2100
accttacctt aagaaacaca tggagcagga cacagaaggt gaggctgcca gacgagtgtg    2160
gggatgcatt gttcagaaca ccatttctct aatattgcat ctcatggaag gccatttgtt    2220
catagaatca accttgctca cgtcagagct tctggaagaa tacttagggt atcaagaata    2280
gcaaggaata gtagcatacg aacacgctcc accaaccaga tcattcaaac ttagagttta    2340
gtgagacatt caaatcttga cttcctgcca agaaccatca tgaatgggta tcttacagta    2400
gctgatgctg tgctcctcaa ttctctttat ccctgttccc tattgttctg agaagtggat    2460
gtctttactg tcacagtata gctcagaagc aggaagtgat gagaccgtga caaccagaac    2520
taagaaaacc agaatgaaac cagcaaagca tttctgcttt cattgtcctg gggagccctg    2580
aaacattctc gtggcacctc tgtttgctca gcaagcccgc catacttctt ccaccatttc    2640
actgagccca cacttcactg ataaggaacc aaagtactga aaggttttga aattgctgac    2700
ctaggccaca aacctggtta ctcacagacc caggactcat ctctctaaca cctcatgtca    2760
gttcttccat actttcatcc atataggggt ctctgtttct actcactgca tcttaaaagc    2820
tggagtgctg tcttctatca tttggctaat gtataattag ttgactctgt ctacagattc    2880
cacatcagaa aattggaaca agcatagatg aaaactatta gggaatgatg taatcatatt    2940
ataattttaa aagaaaaat tttattaaga aaaagctt                             2979
```

<210> SEQ ID NO 12
<211> LENGTH: 320
<212> TYPE: DNA
<213> ORGANISM: mouse

<400> SEQUENCE: 12

```
ttgagcaatt cttggttcca aaccggaagc acaggttctc ccaaacagga tcatttcctt     60
ataaatagct aagattgatg gcctcggttc attgccttca gaacgcatgc ccatcaaccc    120
tgagtatcat aagctggttg gactagccca tcaagtatga agcctttgat gtcttgatca    180
actcagttta tctagagcaa acagccatgt gcccatctgt cactggtcaa acacaaagaa    240
cctgattact tttaaattgt cactgcagac ttttctggcc ccagagaaaa tgacatatac    300
tgaagtcagc agttgtaggt                                                320
```

<210> SEQ ID NO 13
<211> LENGTH: 1216
<212> TYPE: DNA
<213> ORGANISM: chicken

<400> SEQUENCE: 13

-continued

```
tctagaggga cagccccccc ccaaagcccc cagggatgta attacgtccc tcccccgcta    60
gggggcagca gcgagccgcc cggggctccg ctccggtccg gcgctccccc cgcatccccg    120
agccggcagc gtgcgggac agcccgggca cggggaaggt ggcacgggat cgctttcctc     180
tgaacgcttc tcgctgctct ttgagcctgc agacacctgg ggggatacgg ggaaaaagct   240
ttaggctgaa agagagattt agaatgacag aatcatagaa cggcctgggt tgcaaaggag   300
cacagtgctc atccagatcc aaccccctgc tatgtgcagg gtcatcaacc agcagcccag   360
gctgcccaga gccacatcca gcctggcctt gaatgcctgc agggatgggg catccacagc   420
ctccttgggc aacctgttca gtgcgtcacc accctctggg ggaaaaactg cctcctcata   480
tccaacccaa acctcccctg tctcagtgta aagccattcc cccttgtcct atcaagggg    540
agtttgctgt gacattgttg gtctggggtg acacatgttt gccaattcag tgcatcacgg   600
agaggcagat cttggggata aggaagtgca ggacagcatg gacgtgggac atgcaggtgt   660
tgagggctct gggacactct ccaagtcaca gcgttcagaa cagccttaag gataagaaga   720
taggatagaa ggacaaagag caagttaaaa cccagcatgg agaggagcac aaaaaggcca   780
cagacactgc tggtccctgt gtctgagcct gcatgtttga tggtgtctgg atgcaagcag   840
aaggggtgga agagcttgcc tggagagata cagctgggtc agtaggactg ggacaggcag   900
ctggagaatt gccatgtaga tgttcataca atcgtcaaat catgaaggct ggaaaagccc   960
tccaagatcc ccaagaccaa ccccaaccca ccaccgtgc ccactggcca tgtccctcag   1020
tgccacatcc ccacagttct tcatcacctc caggacggt gaccccccca cctccgtggg  1080
cagctgtgcc actgcagcac cgctctttgg agaaggtaaa tcttgctaaa tccagcccga  1140
ccctcccctg gcacaacgta aggccattat ctctcatcca actccaggac ggagtcagtg   1200
aggatggggc tctaga                                                   1216
```

<210> SEQ ID NO 14
<211> LENGTH: 36
<212> TYPE: DNA
<213> ORGANISM: human

<400> SEQUENCE: 14

```
tactaaaagc caggagggga agggacaaca ctaagc                             36
```

<210> SEQ ID NO 15
<211> LENGTH: 35
<212> TYPE: DNA
<213> ORGANISM: human

<400> SEQUENCE: 15

```
tctctgctgc cagtagaggg cacacttact ttact                              35
```

<210> SEQ ID NO 16
<211> LENGTH: 35
<212> TYPE: DNA
<213> ORGANISM: mouse

<400> SEQUENCE: 16

```
tctctgtggc cagtagaggg cacacttact ttact                              35
```

<210> SEQ ID NO 17
<211> LENGTH: 28
<212> TYPE: DNA
<213> ORGANISM: human

<400> SEQUENCE: 17

```
tttgggaacc cgggaggggc gcttatgg                                          28

<210> SEQ ID NO 18
<211> LENGTH: 10
<212> TYPE: DNA
<213> ORGANISM: human
<220> FEATURE:
<221> NAME/KEY: misc_feature
<222> LOCATION: (4)..(5)
<223> OTHER INFORMATION: n is a, c, g, or t

<400> SEQUENCE: 18 ccrnnagrgg                                                              10

<210> SEQ ID NO 19
<211> LENGTH: 36
<212> TYPE: DNA
<213> ORGANISM: human

<400> SEQUENCE: 19
gagctgtgct gctcgcggcc gccaccgccg ggcccc                                 36

<210> SEQ ID NO 20
<211> LENGTH: 36
<212> TYPE: DNA
<213> ORGANISM: human

<400> SEQUENCE: 20
attccagcga gaggcagagg gagcgagcgg gcggcc                                 36

<210> SEQ ID NO 21
<211> LENGTH: 36
<212> TYPE: DNA
<213> ORGANISM: mouse

<400> SEQUENCE: 21
attccagcga gagacagagg gagtgagcgg acggtt                                 36

<210> SEQ ID NO 22
<211> LENGTH: 35
<212> TYPE: DNA
<213> ORGANISM: human

<400> SEQUENCE: 22
tctctgctgc caatatatgg aacacttact ttact                                  35

<210> SEQ ID NO 23
<211> LENGTH: 20
<212> TYPE: DNA
<213> ORGANISM: human

<400> SEQUENCE: 23
gagcctggca agttcaagac                                                   20

<210> SEQ ID NO 24
<211> LENGTH: 20
<212> TYPE: DNA
<213> ORGANISM: human

<400> SEQUENCE: 24
cagaggtgag ggaggtcttg                                                   20

<210> SEQ ID NO 25
<211> LENGTH: 20
```

```
<212> TYPE: DNA
<213> ORGANISM: human

<400> SEQUENCE: 25
caacagggct gtgagaaaga                                              20

<210> SEQ ID NO 26
<211> LENGTH: 20
<212> TYPE: DNA
<213> ORGANISM: human

<400> SEQUENCE: 26
gggcaagatg gtgaaacact                                              20

<210> SEQ ID NO 27
<211> LENGTH: 20
<212> TYPE: DNA
<213> ORGANISM: human

<400> SEQUENCE: 27
agctcaggat tccaagacca                                              20

<210> SEQ ID NO 28
<211> LENGTH: 20
<212> TYPE: DNA
<213> ORGANISM: human

<400> SEQUENCE: 28
aacctgtcat ccaagccaac                                              20

<210> SEQ ID NO 29
<211> LENGTH: 20
<212> TYPE: DNA
<213> ORGANISM: human

<400> SEQUENCE: 29
atcgtccaag tgcagacaca                                              20

<210> SEQ ID NO 30
<211> LENGTH: 20
<212> TYPE: DNA
<213> ORGANISM: human

<400> SEQUENCE: 30
ctaaaagcca ggaggggaag                                              20

<210> SEQ ID NO 31
<211> LENGTH: 20
<212> TYPE: DNA
<213> ORGANISM: human

<400> SEQUENCE: 31
ttaacctggc tgaggtctgg                                              20

<210> SEQ ID NO 32
<211> LENGTH: 20
<212> TYPE: DNA
<213> ORGANISM: human

<400> SEQUENCE: 32
gccattaccg gttctccata                                              20

<210> SEQ ID NO 33
<211> LENGTH: 20
```

```
<212> TYPE: DNA
<213> ORGANISM: human

<400> SEQUENCE: 33
gtccggggag gaaagagtta                                              20

<210> SEQ ID NO 34
<211> LENGTH: 20
<212> TYPE: DNA
<213> ORGANISM: human

<400> SEQUENCE: 34
tagtaattcc agcgagaggc                                              20

<210> SEQ ID NO 35
<211> LENGTH: 20
<212> TYPE: DNA
<213> ORGANISM: human

<400> SEQUENCE: 35
gaggctattc tgcccatttg                                              20

<210> SEQ ID NO 36
<211> LENGTH: 20
<212> TYPE: DNA
<213> ORGANISM: human

<400> SEQUENCE: 36
gcagttgcat ctccgtattg                                              20

<210> SEQ ID NO 37
<211> LENGTH: 20
<212> TYPE: DNA
<213> ORGANISM: human

<400> SEQUENCE: 37
tttattcccc caccaagacc                                              20

<210> SEQ ID NO 38
<211> LENGTH: 19
<212> TYPE: DNA
<213> ORGANISM: human

<400> SEQUENCE: 38
aaggccccca aggtagtta                                               19

<210> SEQ ID NO 39
<211> LENGTH: 20
<212> TYPE: DNA
<213> ORGANISM: human

<400> SEQUENCE: 39
cagtaggatg ggagcaagga                                              20

<210> SEQ ID NO 40
<211> LENGTH: 20
<212> TYPE: DNA
<213> ORGANISM: human

<400> SEQUENCE: 40
ggataaggtc ctggtgctga                                              20

<210> SEQ ID NO 41
<211> LENGTH: 20
```

```
<212> TYPE: DNA
<213> ORGANISM: human

<400> SEQUENCE: 41
ttgggcaatt gtgttgctaa                                       20

<210> SEQ ID NO 42
<211> LENGTH: 20
<212> TYPE: DNA
<213> ORGANISM: human

<400> SEQUENCE: 42
tgcccagagg agtttgtacc                                       20

<210> SEQ ID NO 43
<211> LENGTH: 18
<212> TYPE: DNA
<213> ORGANISM: human

<400> SEQUENCE: 43
gcggacagaa accacatc                                         18

<210> SEQ ID NO 44
<211> LENGTH: 20
<212> TYPE: DNA
<213> ORGANISM: human

<400> SEQUENCE: 44
gggaaagggg cagttgtaaa                                       20

<210> SEQ ID NO 45
<211> LENGTH: 20
<212> TYPE: DNA
<213> ORGANISM: human

<400> SEQUENCE: 45
ctcctcccct gcatgtatgt                                       20

<210> SEQ ID NO 46
<211> LENGTH: 20
<212> TYPE: DNA
<213> ORGANISM: mouse

<400> SEQUENCE: 46 caaccccccac cacctataac                                      20

<210> SEQ ID NO 47
<211> LENGTH: 20
<212> TYPE: DNA
<213> ORGANISM: mouse

<400> SEQUENCE: 47
tcctgcttct ctcccgagta                                       20

<210> SEQ ID NO 48
<211> LENGTH: 18
<212> TYPE: DNA
<213> ORGANISM: mouse

<400> SEQUENCE: 48
ccttcccata acagccct                                         18

<210> SEQ ID NO 49
<211> LENGTH: 20
```

<212> TYPE: DNA
<213> ORGANISM: mouse

<400> SEQUENCE: 49
tgttggtgct gtcctgtgtt                                               20

<210> SEQ ID NO 50
<211> LENGTH: 20
<212> TYPE: DNA
<213> ORGANISM: mouse

<400> SEQUENCE: 50
caaggaagca tcttcccaga                                               20

<210> SEQ ID NO 51
<211> LENGTH: 20
<212> TYPE: DNA
<213> ORGANISM: mouse

<400> SEQUENCE: 51
cgaggagtcc ggaataagaa                                               20

<210> SEQ ID NO 52
<211> LENGTH: 20
<212> TYPE: DNA
<213> ORGANISM: mouse

<400> SEQUENCE: 52
caattcactc ctcccccttt                                               20

<210> SEQ ID NO 53
<211> LENGTH: 20
<212> TYPE: DNA
<213> ORGANISM: mouse

<400> SEQUENCE: 53
acatggcgta ttgtgtggag                                               20

<210> SEQ ID NO 54
<211> LENGTH: 19
<212> TYPE: DNA
<213> ORGANISM: mouse

<400> SEQUENCE: 54
agggatcctg agtcgcagt                                                19

<210> SEQ ID NO 55
<211> LENGTH: 20
<212> TYPE: DNA
<213> ORGANISM: mouse

<400> SEQUENCE: 55
gcacatggac ttgatgttgg                                               20

<210> SEQ ID NO 56
<211> LENGTH: 20
<212> TYPE: DNA
<213> ORGANISM: mouse

<400> SEQUENCE: 56
ctagtccgac gagcgtcact                                               20

<210> SEQ ID NO 57
<211> LENGTH: 20

```
<212> TYPE: DNA
<213> ORGANISM: mouse

<400> SEQUENCE: 57
agaagctggc ctcctaccag                                              20

<210> SEQ ID NO 58
<211> LENGTH: 20
<212> TYPE: DNA
<213> ORGANISM: mouse

<400> SEQUENCE: 58
caacgtcttg gaacgtcaga                                              20

<210> SEQ ID NO 59
<211> LENGTH: 20
<212> TYPE: DNA
<213> ORGANISM: mouse

<400> SEQUENCE: 59
ttgctcccag gtgatagtcc                                              20

<210> SEQ ID NO 60
<211> LENGTH: 20
<212> TYPE: DNA
<213> ORGANISM: mouse

<400> SEQUENCE: 60
cagtcttcac ccgaccatct                                              20

<210> SEQ ID NO 61
<211> LENGTH: 20
<212> TYPE: DNA
<213> ORGANISM: mouse

<400> SEQUENCE: 61
ctgaagccat tctccactcc                                              20

<210> SEQ ID NO 62
<211> LENGTH: 20
<212> TYPE: DNA
<213> ORGANISM: mouse

<400> SEQUENCE: 62
tggaccggta ggtagctttg                                              20

<210> SEQ ID NO 63
<211> LENGTH: 20
<212> TYPE: DNA
<213> ORGANISM: mouse

<400> SEQUENCE: 63
gcccagctaa acctcttcct                                              20

<210> SEQ ID NO 64
<211> LENGTH: 20
<212> TYPE: DNA
<213> ORGANISM: mouse

<400> SEQUENCE: 64
gaggcctagg gaatggactc                                              20

<210> SEQ ID NO 65
<211> LENGTH: 20
```

```
<212> TYPE: DNA
<213> ORGANISM: mouse

<400> SEQUENCE: 65
gcgctgggga tatgattaag                                    20

<210> SEQ ID NO 66
<211> LENGTH: 20
<212> TYPE: DNA
<213> ORGANISM: mouse

<400> SEQUENCE: 66
caatatcttg aggcgctgct                                    20

<210> SEQ ID NO 67
<211> LENGTH: 20
<212> TYPE: DNA
<213> ORGANISM: mouse

<400> SEQUENCE: 67
ctgaggacat gctgcaaaac                                    20

<210> SEQ ID NO 68
<211> LENGTH: 20
<212> TYPE: DNA
<213> ORGANISM: mouse

<400> SEQUENCE: 68
agaatggcca caaagtccac                                    20

<210> SEQ ID NO 69
<211> LENGTH: 20
<212> TYPE: DNA
<213> ORGANISM: mouse

<400> SEQUENCE: 69
cctggtgcag aagacacaga                                    20

<210> SEQ ID NO 70
<211> LENGTH: 21
<212> TYPE: DNA
<213> ORGANISM: mouse

<400> SEQUENCE: 70
tacaggcatg aaccaaccac a                                  21

<210> SEQ ID NO 71
<211> LENGTH: 20
<212> TYPE: DNA
<213> ORGANISM: mouse

<400> SEQUENCE: 71
tcactgcagc cttgaacttg                                    20

<210> SEQ ID NO 72
<211> LENGTH: 19
<212> TYPE: DNA
<213> ORGANISM: mouse

<400> SEQUENCE: 72
agcagtcctc ccacctcag                                     19

<210> SEQ ID NO 73
<211> LENGTH: 20
```

```
<212> TYPE: DNA
<213> ORGANISM: mouse

<400> SEQUENCE: 73
ggggtaaagt gggtttaggc                                            20

<210> SEQ ID NO 74
<211> LENGTH: 20
<212> TYPE: DNA
<213> ORGANISM: mouse

<400> SEQUENCE: 74
gggctggcac agaaaatatc                                            20

<210> SEQ ID NO 75
<211> LENGTH: 20
<212> TYPE: DNA
<213> ORGANISM: mouse

<400> SEQUENCE: 75
cacaggaaag ctcttcagca                                            20

<210> SEQ ID NO 76
<211> LENGTH: 20
<212> TYPE: DNA
<213> ORGANISM: mouse

<400> SEQUENCE: 76
tgcctgtggg ttcagaactt                                            20

<210> SEQ ID NO 77
<211> LENGTH: 20
<212> TYPE: DNA
<213> ORGANISM: mouse

<400> SEQUENCE: 77
caggcggttc cttaaaacaa                                            20

<210> SEQ ID NO 78
<211> LENGTH: 20
<212> TYPE: DNA
<213> ORGANISM: mouse

<400> SEQUENCE: 78
caaaggtgct agacgggaga                                            20

<210> SEQ ID NO 79
<211> LENGTH: 18
<212> TYPE: DNA
<213> ORGANISM: mouse

<400> SEQUENCE: 79
agcgcagctc tgctcgcc                                              18

<210> SEQ ID NO 80
<211> LENGTH: 20
<212> TYPE: DNA
<213> ORGANISM: mouse

<400> SEQUENCE: 80
gcattcgact catctcagca                                            20

<210> SEQ ID NO 81
<211> LENGTH: 19
```

<212> TYPE: DNA
<213> ORGANISM: mouse

<400> SEQUENCE: 81
cccgtccaac actcctttt                                                19

<210> SEQ ID NO 82
<211> LENGTH: 20
<212> TYPE: DNA
<213> ORGANISM: mouse

<400> SEQUENCE: 82
cgggaggcag tcttgagtta                                               20

<210> SEQ ID NO 83
<211> LENGTH: 20
<212> TYPE: DNA
<213> ORGANISM: mouse

<400> SEQUENCE: 83
acgcacaaga gttccgtagc                                               20

<210> SEQ ID NO 84
<211> LENGTH: 20
<212> TYPE: DNA
<213> ORGANISM: mouse

<400> SEQUENCE: 84
aaaacaccca gaaatgctgg                                               20

<210> SEQ ID NO 85
<211> LENGTH: 20
<212> TYPE: DNA
<213> ORGANISM: mouse

<400> SEQUENCE: 85
caggattact gggaggctga                                               20

<210> SEQ ID NO 86
<211> LENGTH: 21
<212> TYPE: DNA
<213> ORGANISM: mouse

<400> SEQUENCE: 86
tcctaggcgt cactctctga a                                             21

<210> SEQ ID NO 87
<211> LENGTH: 20
<212> TYPE: DNA
<213> ORGANISM: mouse

<400> SEQUENCE: 87
cagccaaaag ccagtagagg                                               20

<210> SEQ ID NO 88
<211> LENGTH: 20
<212> TYPE: DNA
<213> ORGANISM: mouse

<400> SEQUENCE: 88
ggaatgacag cctggtttgt                                               20

<210> SEQ ID NO 89
<211> LENGTH: 20

```
<212> TYPE: DNA
<213> ORGANISM: mouse

<400> SEQUENCE: 89
gcaccactga gtcatttcca                                               20

<210> SEQ ID NO 90
<211> LENGTH: 20
<212> TYPE: DNA
<213> ORGANISM: mouse

<400> SEQUENCE: 90
cacgtgagaa tttcgcttga                                               20

<210> SEQ ID NO 91
<211> LENGTH: 20
<212> TYPE: DNA
<213> ORGANISM: mouse

<400> SEQUENCE: 91
tgggaaagct tctggaaatg                                               20

<210> SEQ ID NO 92
<211> LENGTH: 20
<212> TYPE: DNA
<213> ORGANISM: mouse

<400> SEQUENCE: 92
tcccccaatg ttcttgaatc                                               20

<210> SEQ ID NO 93
<211> LENGTH: 20
<212> TYPE: DNA
<213> ORGANISM: mouse

<400> SEQUENCE: 93
cccgatggca gagagtacat                                               20

<210> SEQ ID NO 94
<211> LENGTH: 20
<212> TYPE: DNA
<213> ORGANISM: mouse

<400> SEQUENCE: 94
atctgagcaa caggcaaggt                                               20

<210> SEQ ID NO 95
<211> LENGTH: 20
<212> TYPE: DNA
<213> ORGANISM: mouse

<400> SEQUENCE: 95
gttgtggctc tcggatttgt                                               20

<210> SEQ ID NO 96
<211> LENGTH: 20
<212> TYPE: DNA
<213> ORGANISM: mouse

<400> SEQUENCE: 96
tcttttgctc tgtgcattgg                                               20

<210> SEQ ID NO 97
<211> LENGTH: 19
```

```
<212> TYPE: DNA
<213> ORGANISM: mouse

<400> SEQUENCE: 97
aatcctcttt gccctgtg                                              19

<210> SEQ ID NO 98
<211> LENGTH: 20
<212> TYPE: DNA
<213> ORGANISM: mouse

<400> SEQUENCE: 98
ccgaccattt tctcttgctc                                            20

<210> SEQ ID NO 99
<211> LENGTH: 20
<212> TYPE: DNA
<213> ORGANISM: mouse

<400> SEQUENCE: 99
tccagagctg ccttcttagg                                            20

<210> SEQ ID NO 100
<211> LENGTH: 20
<212> TYPE: DNA
<213> ORGANISM: mouse

<400> SEQUENCE: 100
ctcaccgcag tcttcctagc                                            20

<210> SEQ ID NO 101
<211> LENGTH: 20
<212> TYPE: DNA
<213> ORGANISM: mouse

<400> SEQUENCE: 101
ctgaaccact cccctttcag                                            20

<210> SEQ ID NO 102
<211> LENGTH: 20
<212> TYPE: DNA
<213> ORGANISM: mouse

<400> SEQUENCE: 102
actgaggggt caatgcactc                                            20

<210> SEQ ID NO 103
<211> LENGTH: 20
<212> TYPE: DNA
<213> ORGANISM: mouse

<400> SEQUENCE: 103
tcgtctgctt gaatggacag                                            20

<210> SEQ ID NO 104
<211> LENGTH: 20
<212> TYPE: DNA
<213> ORGANISM: mouse

<400> SEQUENCE: 104
aagctctgca accctctgaa                                            20

<210> SEQ ID NO 105
<211> LENGTH: 20
```

```
<212> TYPE: DNA
<213> ORGANISM: mouse

<400> SEQUENCE: 105
tccagctgag ttgtttgtgg                                          20

<210> SEQ ID NO 106
<211> LENGTH: 20
<212> TYPE: DNA
<213> ORGANISM: mouse

<400> SEQUENCE: 106
ttccattctt caagggttg                                           20

<210> SEQ ID NO 107
<211> LENGTH: 20
<212> TYPE: DNA
<213> ORGANISM: mouse

<400> SEQUENCE: 107
agaacagctt ggccagtgac                                          20

<210> SEQ ID NO 108
<211> LENGTH: 18
<212> TYPE: DNA
<213> ORGANISM: mouse

<400> SEQUENCE: 108
cacagggttc caactttt                                            18

<210> SEQ ID NO 109
<211> LENGTH: 20
<212> TYPE: DNA
<213> ORGANISM: mouse

<400> SEQUENCE: 109
cccagttctc tggacctttg                                          20

<210> SEQ ID NO 110
<211> LENGTH: 20
<212> TYPE: DNA
<213> ORGANISM: mouse

<400> SEQUENCE: 110
ccaggaaagc aagagaagga                                          20

<210> SEQ ID NO 111
<211> LENGTH: 20
<212> TYPE: DNA
<213> ORGANISM: mouse

<400> SEQUENCE: 111
gtcaccgggt attggatcac                                          20

<210> SEQ ID NO 112
<211> LENGTH: 20
<212> TYPE: DNA
<213> ORGANISM: mouse

<400> SEQUENCE: 112
tgagagagca gcagcttcaa                                          20

<210> SEQ ID NO 113
<211> LENGTH: 20
```

```
<212> TYPE: DNA
<213> ORGANISM: human

<400> SEQUENCE: 113
ctatgagatc gatgtggacc                                              20

<210> SEQ ID NO 114
<211> LENGTH: 22
<212> TYPE: DNA
<213> ORGANISM: human

<400> SEQUENCE: 114
gctaatgaaa gtcgaactat gg                                           22

<210> SEQ ID NO 115
<211> LENGTH: 20
<212> TYPE: DNA
<213> ORGANISM: human

<400> SEQUENCE: 115
gagtttcatc gatgtggggg                                              20

<210> SEQ ID NO 116
<211> LENGTH: 20
<212> TYPE: DNA
<213> ORGANISM: human

<400> SEQUENCE: 116
ggggtgcgtc gacagcatgt                                              20

<210> SEQ ID NO 117
<211> LENGTH: 20
<212> TYPE: DNA
<213> ORGANISM: human

<400> SEQUENCE: 117
gggtgaatga atgccctatg                                              20

<210> SEQ ID NO 118
<211> LENGTH: 20
<212> TYPE: DNA
<213> ORGANISM: human

<400> SEQUENCE: 118
tactccatgc gaggtccact                                              20

<210> SEQ ID NO 119
<211> LENGTH: 20
<212> TYPE: DNA
<213> ORGANISM: human

<400> SEQUENCE: 119
gggtgaatga atgccctatg                                              20

<210> SEQ ID NO 120
<211> LENGTH: 20
<212> TYPE: DNA
<213> ORGANISM: human

<400> SEQUENCE: 120
tactccatgc gaggtccact                                              20

<210> SEQ ID NO 121
<211> LENGTH: 20
```

```
<212> TYPE: DNA
<213> ORGANISM: human

<400> SEQUENCE: 121
aggtagcagg atctcctgag                                              20

<210> SEQ ID NO 122
<211> LENGTH: 20
<212> TYPE: DNA
<213> ORGANISM: human

<400> SEQUENCE: 122
aaaaccaacc caatgtctgg                                              20

<210> SEQ ID NO 123
<211> LENGTH: 20
<212> TYPE: DNA
<213> ORGANISM: human

<400> SEQUENCE: 123
ctgtgccctt ttccttcaaa                                              20

<210> SEQ ID NO 124
<211> LENGTH: 20
<212> TYPE: DNA
<213> ORGANISM: human

<400> SEQUENCE: 124
tccaaaacgt cctgacacac                                              20

<210> SEQ ID NO 125
<211> LENGTH: 20
<212> TYPE: DNA
<213> ORGANISM: human

<400> SEQUENCE: 125
cccacaacac tgaaagcaga                                              20

<210> SEQ ID NO 126
<211> LENGTH: 20
<212> TYPE: DNA
<213> ORGANISM: human

<400> SEQUENCE: 126
aacacaccag cctgataggg                                              20

<210> SEQ ID NO 127
<211> LENGTH: 20
<212> TYPE: DNA
<213> ORGANISM: human

<400> SEQUENCE: 127
gaggcaaatt aacgctggtg                                              20

<210> SEQ ID NO 128
<211> LENGTH: 20
<212> TYPE: DNA
<213> ORGANISM: human

<400> SEQUENCE: 128
atatcccagc acttgccatc                                              20

<210> SEQ ID NO 129
<211> LENGTH: 20
```

<212> TYPE: DNA
<213> ORGANISM: human

<400> SEQUENCE: 129
gcccaatatg ctgttccaat                                               20

<210> SEQ ID NO 130
<211> LENGTH: 20
<212> TYPE: DNA
<213> ORGANISM: human

<400> SEQUENCE: 130
aaccttggca gggaggtagt                                               20

<210> SEQ ID NO 131
<211> LENGTH: 20
<212> TYPE: DNA
<213> ORGANISM: human

<400> SEQUENCE: 131
aagctgcagt gagccgtaat                                               20

<210> SEQ ID NO 132
<211> LENGTH: 20
<212> TYPE: DNA
<213> ORGANISM: human

<400> SEQUENCE: 132
atcaagtcca gggcaaacag                                               20

<210> SEQ ID NO 133
<211> LENGTH: 20
<212> TYPE: DNA
<213> ORGANISM: human

<400> SEQUENCE: 133
gtggcatgga catcatcaag                                               20

<210> SEQ ID NO 134
<211> LENGTH: 20
<212> TYPE: DNA
<213> ORGANISM: human

<400> SEQUENCE: 134
ttacagaagg gaccggtttg                                               20

<210> SEQ ID NO 135
<211> LENGTH: 20
<212> TYPE: DNA
<213> ORGANISM: human

<400> SEQUENCE: 135
gacagaaggt tctgggatg                                                20

<210> SEQ ID NO 136
<211> LENGTH: 20
<212> TYPE: DNA
<213> ORGANISM: human

<400> SEQUENCE: 136
atggaaggca gtgagaagga                                               20

<210> SEQ ID NO 137
<211> LENGTH: 20

```
<212> TYPE: DNA
<213> ORGANISM: human

<400> SEQUENCE: 137
gggaaagcag ttacccttc                                                20

<210> SEQ ID NO 138
<211> LENGTH: 20
<212> TYPE: DNA
<213> ORGANISM: human

<400> SEQUENCE: 138
agtggagcga acacagacct                                               20

<210> SEQ ID NO 139
<211> LENGTH: 20
<212> TYPE: DNA
<213> ORGANISM: human

<400> SEQUENCE: 139
aaggggagga gaaagagctg                                               20

<210> SEQ ID NO 140
<211> LENGTH: 20
<212> TYPE: DNA
<213> ORGANISM: human

<400> SEQUENCE: 140
agagcgagac cctgtctgtg                                               20

<210> SEQ ID NO 141
<211> LENGTH: 20
<212> TYPE: DNA
<213> ORGANISM: human

<400> SEQUENCE: 141
gggtctcact ccattgccta                                               20

<210> SEQ ID NO 142
<211> LENGTH: 20
<212> TYPE: DNA
<213> ORGANISM: human

<400> SEQUENCE: 142
cgtgggctca ctggttactt                                               20

<210> SEQ ID NO 143
<211> LENGTH: 20
<212> TYPE: DNA
<213> ORGANISM: human

<400> SEQUENCE: 143
agcaattgca ggatgctttc                                               20

<210> SEQ ID NO 144
<211> LENGTH: 20
<212> TYPE: DNA
<213> ORGANISM: human

<400> SEQUENCE: 144
ataacccacc ccagcatgta                                               20

<210> SEQ ID NO 145
<211> LENGTH: 20
```

```
<212> TYPE: DNA
<213> ORGANISM: human

<400> SEQUENCE: 145
aaccgggaga agtgtgaaga                                               20

<210> SEQ ID NO 146
<211> LENGTH: 20
<212> TYPE: DNA
<213> ORGANISM: human

<400> SEQUENCE: 146
gtgtagcggc atctcactgt                                               20

<210> SEQ ID NO 147
<211> LENGTH: 20
<212> TYPE: DNA
<213> ORGANISM: human

<400> SEQUENCE: 147
ctctgctggg tctcatctcc                                               20

<210> SEQ ID NO 148
<211> LENGTH: 20
<212> TYPE: DNA
<213> ORGANISM: human

<400> SEQUENCE: 148
ccactggtct gtctgggatt                                               20

<210> SEQ ID NO 149
<211> LENGTH: 20
<212> TYPE: DNA
<213> ORGANISM: human

<400> SEQUENCE: 149
gttgaggcat gagtcctggt                                               20

<210> SEQ ID NO 150
<211> LENGTH: 20
<212> TYPE: DNA
<213> ORGANISM: human

<400> SEQUENCE: 150
ggatgtcccc tagcaaggat                                               20

<210> SEQ ID NO 151
<211> LENGTH: 20
<212> TYPE: DNA
<213> ORGANISM: human

<400> SEQUENCE: 151
agccagcctt tctgttttga                                               20

<210> SEQ ID NO 152
<211> LENGTH: 20
<212> TYPE: DNA
<213> ORGANISM: human

<400> SEQUENCE: 152
gggctcatag ctgaatctgg                                               20

<210> SEQ ID NO 153
<211> LENGTH: 20
```

```
<212> TYPE: DNA
<213> ORGANISM: human

<400> SEQUENCE: 153
agaatccaca aggcaacctg                                                20

<210> SEQ ID NO 154
<211> LENGTH: 20
<212> TYPE: DNA
<213> ORGANISM: human

<400> SEQUENCE: 154
tgcattcaca agcatcacaa                                                20

<210> SEQ ID NO 155
<211> LENGTH: 20
<212> TYPE: DNA
<213> ORGANISM: human

<400> SEQUENCE: 155
gatggctaga aggctgttgc                                                20

<210> SEQ ID NO 156
<211> LENGTH: 20
<212> TYPE: DNA
<213> ORGANISM: human

<400> SEQUENCE: 156
ccctcctggt gttcacactt                                                20

<210> SEQ ID NO 157
<211> LENGTH: 20
<212> TYPE: DNA
<213> ORGANISM: human

<400> SEQUENCE: 157
gcgattgtaa gcaactgcaa                                                20

<210> SEQ ID NO 158
<211> LENGTH: 20
<212> TYPE: DNA
<213> ORGANISM: human

<400> SEQUENCE: 158
ttgaatcctg gttcctttgc                                                20

<210> SEQ ID NO 159
<211> LENGTH: 20
<212> TYPE: DNA
<213> ORGANISM: human

<400> SEQUENCE: 159
ggcacagagc ctcttgtagg                                                20

<210> SEQ ID NO 160
<211> LENGTH: 20
<212> TYPE: DNA
<213> ORGANISM: human

<400> SEQUENCE: 160
atgttctgga agtggcaggt                                                20

<210> SEQ ID NO 161
<211> LENGTH: 20
```

```
<212> TYPE: DNA
<213> ORGANISM: human

<400> SEQUENCE: 161
tgcacattgc acttctctcc                                           20

<210> SEQ ID NO 162
<211> LENGTH: 20
<212> TYPE: DNA
<213> ORGANISM: human

<400> SEQUENCE: 162
gagaccccat ctcgctaaaa                                           20

<210> SEQ ID NO 163
<211> LENGTH: 20
<212> TYPE: DNA
<213> ORGANISM: human

<400> SEQUENCE: 163
taatgacccc acctcctctg                                           20

<210> SEQ ID NO 164
<211> LENGTH: 20
<212> TYPE: DNA
<213> ORGANISM: human

<400> SEQUENCE: 164
gcaattggag gacaaatgct                                           20

<210> SEQ ID NO 165
<211> LENGTH: 20
<212> TYPE: DNA
<213> ORGANISM: human

<400> SEQUENCE: 165
ggttttgcct tatggatgct                                           20

<210> SEQ ID NO 166
<211> LENGTH: 20
<212> TYPE: DNA
<213> ORGANISM: human

<400> SEQUENCE: 166
tggaggcgga gtaagactgt                                           20

<210> SEQ ID NO 167
<211> LENGTH: 20
<212> TYPE: DNA
<213> ORGANISM: human

<400> SEQUENCE: 167
tttttgcttg cactttgtgg                                           20

<210> SEQ ID NO 168
<211> LENGTH: 20
<212> TYPE: DNA
<213> ORGANISM: human

<400> SEQUENCE: 168
aaatgtggag gtgggaggat                                           20

<210> SEQ ID NO 169
<211> LENGTH: 20
```

```
<212> TYPE: DNA
<213> ORGANISM: human

<400> SEQUENCE: 169 tgccctttc atcacatcag                                           20

<210> SEQ ID NO 170
<211> LENGTH: 20
<212> TYPE: DNA
<213> ORGANISM: human

<400> SEQUENCE: 170
tggacagaaa aaccctttgg                                          20

<210> SEQ ID NO 171
<211> LENGTH: 20
<212> TYPE: DNA
<213> ORGANISM: human

<400> SEQUENCE: 171
aggggatgaa aggccacttg                                          20

<210> SEQ ID NO 172
<211> LENGTH: 20
<212> TYPE: DNA
<213> ORGANISM: human

<400> SEQUENCE: 172
gcacccagcc tgtttcttta                                          20

<210> SEQ ID NO 173
<211> LENGTH: 20
<212> TYPE: DNA
<213> ORGANISM: human

<400> SEQUENCE: 173
ctattctgtg cctggcgaac                                          20

<210> SEQ ID NO 174
<211> LENGTH: 20
<212> TYPE: DNA
<213> ORGANISM: human

<400> SEQUENCE: 174
gttgtgatca cccacagctc                                          20

<210> SEQ ID NO 175
<211> LENGTH: 20
<212> TYPE: DNA
<213> ORGANISM: human

<400> SEQUENCE: 175
gtgatcaccc acagctccat                                          20

<210> SEQ ID NO 176
<211> LENGTH: 20
<212> TYPE: DNA
<213> ORGANISM: human

<400> SEQUENCE: 176
tgtgggtgaa agtgttcctg                                          20

<210> SEQ ID NO 177
<211> LENGTH: 20
```

```
<212> TYPE: DNA
<213> ORGANISM: human

<400> SEQUENCE: 177
gccaggattg tctcgatttc                                           20

<210> SEQ ID NO 178
<211> LENGTH: 20
<212> TYPE: DNA
<213> ORGANISM: human

<400> SEQUENCE: 178
cttctgagcc actccgtctc                                           20

<210> SEQ ID NO 179
<211> LENGTH: 20
<212> TYPE: DNA
<213> ORGANISM: human

<400> SEQUENCE: 179
ggcaggaatg actcttggag                                           20

<210> SEQ ID NO 180
<211> LENGTH: 20
<212> TYPE: DNA
<213> ORGANISM: human

<400> SEQUENCE: 180
gtggtgcaat cacagctcac                                           20

<210> SEQ ID NO 181
<211> LENGTH: 20
<212> TYPE: DNA
<213> ORGANISM: human

<400> SEQUENCE: 181
cacctcctgg gctcaaataa                                           20

<210> SEQ ID NO 182
<211> LENGTH: 20
<212> TYPE: DNA
<213> ORGANISM: human

<400> SEQUENCE: 182
gcacacatgg aacaaggcta                                           20

<210> SEQ ID NO 183
<211> LENGTH: 20
<212> TYPE: DNA
<213> ORGANISM: human

<400> SEQUENCE: 183
gaatgcagtc ttgtgcctca                                           20

<210> SEQ ID NO 184
<211> LENGTH: 20
<212> TYPE: DNA
<213> ORGANISM: human

<400> SEQUENCE: 184
aggatggaga aaatggagca                                           20

<210> SEQ ID NO 185
<211> LENGTH: 20
```

```
<212> TYPE: DNA
<213> ORGANISM: human

<400> SEQUENCE: 185
ctggcaaaag gaatgtggat                                               20

<210> SEQ ID NO 186
<211> LENGTH: 20
<212> TYPE: DNA
<213> ORGANISM: human

<400> SEQUENCE: 186
gctccccaat agctttcctt                                               20

<210> SEQ ID NO 187
<211> LENGTH: 20
<212> TYPE: DNA
<213> ORGANISM: human

<400> SEQUENCE: 187
ggaagcgctg attcattagg                                               20

<210> SEQ ID NO 188
<211> LENGTH: 20
<212> TYPE: DNA
<213> ORGANISM: human

<400> SEQUENCE: 188
tttttatggc tggctccttc                                               20

<210> SEQ ID NO 189
<211> LENGTH: 20
<212> TYPE: DNA
<213> ORGANISM: human

<400> SEQUENCE: 189
agggaatcct ccctcatttt                                               20

<210> SEQ ID NO 190
<211> LENGTH: 20
<212> TYPE: DNA
<213> ORGANISM: human

<400> SEQUENCE: 190
tccctccctg ctttccttat                                               20

<210> SEQ ID NO 191
<211> LENGTH: 20
<212> TYPE: DNA
<213> ORGANISM: human

<400> SEQUENCE: 191
caaatggagc tgtgggtgat                                               20

<210> SEQ ID NO 192
<211> LENGTH: 20
<212> TYPE: DNA
<213> ORGANISM: human

<400> SEQUENCE: 192
caaatggagc tgtgggtcat                                               20

<210> SEQ ID NO 193
<211> LENGTH: 20
```

<212> TYPE: DNA
<213> ORGANISM: human

<400> SEQUENCE: 193
tgtgcgaatt tcacaaaagg                                              20

<210> SEQ ID NO 194
<211> LENGTH: 20
<212> TYPE: DNA
<213> ORGANISM: human

<400> SEQUENCE: 194
ggaagagagg gagcaaatcc                                              20

<210> SEQ ID NO 195
<211> LENGTH: 20
<212> TYPE: DNA
<213> ORGANISM: human

<400> SEQUENCE: 195
agctggcacc aacctaccta                                              20

<210> SEQ ID NO 196
<211> LENGTH: 20
<212> TYPE: DNA
<213> ORGANISM: human

<400> SEQUENCE: 196
tagtggtgag gctgggaaac                                              20

<210> SEQ ID NO 197
<211> LENGTH: 19
<212> TYPE: DNA
<213> ORGANISM: human

<400> SEQUENCE: 197
atgcatgtcc caaaacaag                                               19

<210> SEQ ID NO 198
<211> LENGTH: 20
<212> TYPE: DNA
<213> ORGANISM: human

<400> SEQUENCE: 198
cacttgagca caggagttgg                                              20

<210> SEQ ID NO 199
<211> LENGTH: 20
<212> TYPE: DNA
<213> ORGANISM: human

<400> SEQUENCE: 199
gcactttgtg aggctgaaga                                              20

<210> SEQ ID NO 200
<211> LENGTH: 20
<212> TYPE: DNA
<213> ORGANISM: human

<400> SEQUENCE: 200
gattccccaa ggcagtcatt                                              20

<210> SEQ ID NO 201
<211> LENGTH: 20

```
<212> TYPE: DNA
<213> ORGANISM: human

<400> SEQUENCE: 201
aagccctgag atgggagttt                                              20

<210> SEQ ID NO 202
<211> LENGTH: 21
<212> TYPE: DNA
<213> ORGANISM: human

<400> SEQUENCE: 202
gcctctagcc taagcaaaac a                                            21

<210> SEQ ID NO 203
<211> LENGTH: 20
<212> TYPE: DNA
<213> ORGANISM: human

<400> SEQUENCE: 203
atcttcaacg tgtggcttcc                                              20

<210> SEQ ID NO 204
<211> LENGTH: 20
<212> TYPE: DNA
<213> ORGANISM: human

<400> SEQUENCE: 204
gctccccaat agctttcctt                                              20

<210> SEQ ID NO 205
<211> LENGTH: 20
<212> TYPE: DNA
<213> ORGANISM: human

<400> SEQUENCE: 205
ggaagcgctg attcattagg                                              20

<210> SEQ ID NO 206
<211> LENGTH: 20
<212> TYPE: DNA
<213> ORGANISM: human

<400> SEQUENCE: 206
aggcagaggt tggagaatca                                              20

<210> SEQ ID NO 207
<211> LENGTH: 93
<212> TYPE: DNA
<213> ORGANISM: mouse

<400> SEQUENCE: 207
gtcttaggca aggaagcatc ttcccagaac ctggaaaccc tgcagccctg cccccatccg  60
acctccgccc tcgttggctt cgcaacgctg tgg                               93

<210> SEQ ID NO 208
<211> LENGTH: 245
<212> TYPE: DNA
<213> ORGANISM: mouse

<400> SEQUENCE: 208
tttcacaaat ccgagagcca caacccgggt ggtgggggt gagggggcgg ggaaagagtc   60
tctgcagcaa aacgcagact agggattggt ggctcttggt gtttgaggca aaatcctaga 120
```

```
ggctgtagtc attttgcaat ccttaaagct gaattgtgca atgagctcga tgaaggaaga      180
tactatcatt caacagctga atcctaaatt gcaaactcag tggctaataa caactttgaa      240
caatg                                                                  245
```